(12) United States Patent
Kuchroo et al.

(10) Patent No.: US 11,884,717 B2
(45) Date of Patent: Jan. 30, 2024

(54) METHOD OF TREATING AUTOIMMUNE DISEASE WITH LYMPHOCYTE ANTIGEN CD5-LIKE (CD5L) PROTEIN

(71) Applicants: The Brigham and Women's Hospital, Inc., Boston, MA (US); The Broad Institute, Inc., Cambridge, MA (US); Massachusetts Institute of Technology, Cambridge, MA (US)

(72) Inventors: Vijay K. Kuchroo, Boston, MA (US); Chao Wang, Boston, MA (US); Aviv Regev, Cambridge, MA (US); Karthik Shekhar, Cambridge, MA (US)

(73) Assignees: The Brigham and Women's Hospital, Inc., Boston, MA (US); The Broad Institute, Inc., Cambridge, MA (US); Massachusetts Institute of Technology, Cambridge, MA (US)

( * ) Notice: Subject to any disclaimer, the term of this patent is extended or adjusted under 35 U.S.C. 154(b) by 329 days.

(21) Appl. No.: 17/226,506

(22) Filed: Apr. 9, 2021

(65) Prior Publication Data
US 2021/0317186 A1 Oct. 14, 2021

Related U.S. Application Data

(63) Continuation of application No. 15/777,054, filed as application No. PCT/US2016/062592 on Nov. 17, 2016, now Pat. No. 11,001,622.

(60) Provisional application No. 62/257,589, filed on Nov. 19, 2015.

(51) Int. Cl.
| | |
|---|---|
| *A61K 38/20* | (2006.01) |
| *A61K 38/17* | (2006.01) |
| *C07K 14/705* | (2006.01) |
| *A61P 37/00* | (2006.01) |
| *A61P 1/00* | (2006.01) |
| *A61P 35/00* | (2006.01) |
| *A61K 39/395* | (2006.01) |
| *A61K 45/06* | (2006.01) |
| *C07K 14/54* | (2006.01) |
| *C07K 16/24* | (2006.01) |
| *C07K 16/28* | (2006.01) |
| *C12N 15/113* | (2010.01) |
| *A61K 39/00* | (2006.01) |

(52) U.S. Cl.
CPC ...... *C07K 14/70596* (2013.01); *A61K 38/177* (2013.01); *A61K 38/1709* (2013.01); *A61K 38/208* (2013.01); *A61K 39/3955* (2013.01); *A61K 45/06* (2013.01); *A61P 1/00* (2018.01); *A61P 35/00* (2018.01); *A61P 37/00* (2018.01); *C07K 14/5434* (2013.01); *C07K 16/244* (2013.01); *C07K 16/2896* (2013.01); *C12N 15/1136* (2013.01); *C12N 15/1138* (2013.01); *A61K 2039/575* (2013.01); *C12N 2310/11* (2013.01); *C12N 2310/14* (2013.01); *C12N 2310/20* (2017.05)

(58) Field of Classification Search
CPC . A61K 38/208; A61K 38/177; A61K 38/1709
See application file for complete search history.

(56) References Cited

U.S. PATENT DOCUMENTS

| | | | |
|---|---|---|---|
| 3,687,808 A | 8/1972 | Merigan et al. |
| 4,458,066 A | 7/1984 | Caruthers et al. |
| 4,469,863 A | 9/1984 | Ts'o et al. |
| 4,476,301 A | 10/1984 | Imbach et al. |
| 4,522,811 A | 6/1985 | Eppstein et al. |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |

(Continued)

FOREIGN PATENT DOCUMENTS

| | | |
|---|---|---|
| EP | 0 043 075 A2 | 1/1982 |
| EP | 0791359 A1 | 8/1997 |

(Continued)

OTHER PUBLICATIONS

The Brigham and Women's Hospital, Inc., "International Preliminary Report on Patentability issued in International Application No. PCT/US2016/062592", dated May 31, 2018, 9 pages.

(Continued)

*Primary Examiner* — Prema M Mertz
(74) *Attorney, Agent, or Firm* — F. Brent Nix, Esq.; Johnson, Marcou, Isaacs & Nix, LLC; Michael B. Scher, Esq.

(57) ABSTRACT

Described herein are methods for suppressing an immune response in a subject, e.g., a subject with an autoimmune disease, by administering to the subject a therapeutically effective amount of recombinant CD5L, CD5L homodimers and/or CD5L:p40 heterodimers, or nucleic acids encoding any of these. Also described are methods for enhancing an immune response in a subject, e.g., a subject with cancer, infection, or an immune deficiency, by administering to the subject a therapeutically effective amount of an antibody or antigen-binding fragment thereof that binds specifically to CD5L, D5L homodimers and/or CD5L:p40 heterodimers, and inhibits their binding to the IL-23 receptor, or inhibits formation of the CD5L homodimer and/or CD5L:p40 heterodimer, or inhibitory nucleic acids that target CD5L and/or p40.

2 Claims, 50 Drawing Sheets
Specification includes a Sequence Listing.

(56) References Cited

U.S. PATENT DOCUMENTS

| | | |
|---|---|---|
| 4,835,263 A | 5/1989 | Nguyen et al. |
| 4,845,205 A | 7/1989 | Huynh Dinh et al. |
| 4,868,116 A | 9/1989 | Morgan et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger |
| 4,980,286 A | 12/1990 | Morgan et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,109,124 A | 4/1992 | Ramachandran et al. |
| 5,112,963 A | 5/1992 | Pieles et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,235,033 A | 8/1993 | Summerton et al. |
| 5,245,022 A | 9/1993 | Weis et al. |
| 5,254,469 A | 10/1993 | Warre et al. |
| 5,256,775 A | 10/1993 | Froehler |
| 5,258,506 A | 11/1993 | Urdea et al. |
| 5,262,536 A | 11/1993 | Hobbs, Jr. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,321,131 A | 6/1994 | Agrawal et al. |
| 5,328,470 A | 7/1994 | Nabel et al. |
| 5,366,878 A | 11/1994 | Pederson et al. |
| 5,367,066 A | 11/1994 | Urdea et al. |
| 5,371,241 A | 12/1994 | Brush |
| 5,391,723 A | 2/1995 | Priest |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,203 A | 5/1995 | Letsinger |
| 5,432,272 A | 7/1995 | Benner |
| 5,434,257 A | 7/1995 | Matteucci et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,510,475 A | 4/1996 | Agrawal et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,525,465 A | 6/1996 | Haralambidis et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,545,730 A | 8/1996 | Urdea et al. |
| 5,550,111 A | 8/1996 | Suhadolnik et al. |
| 5,552,538 A | 9/1996 | Urdea et al. |
| 5,552,540 A | 9/1996 | Haralambidis |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,567,810 A | 10/1996 | Weis et al. |
| 5,571,799 A | 11/1996 | Tkachuk et al. |
| 5,574,142 A | 11/1996 | Meyer, Jr. et al. |
| 5,578,717 A | 11/1996 | Urdea et al. |
| 5,578,718 A | 11/1996 | Cook et al. |
| 5,580,731 A | 12/1996 | Chang et al. |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,595,726 A | 1/1997 | Magda et al. |
| 5,596,086 A | 1/1997 | Matteucci et al. |
| 5,596,091 A | 1/1997 | Switzer |
| 5,597,696 A | 1/1997 | Linn et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,652,355 A | 7/1997 | Metelev et al. |
| 5,652,356 A | 7/1997 | Agrawal |
| 5,663,312 A | 9/1997 | Chaturvedula |
| 5,677,437 A | 10/1997 | Teng et al. |
| 5,677,439 A | 10/1997 | Weis et al. |
| 5,681,941 A | 10/1997 | Cook et al. |
| 5,686,281 A | 11/1997 | Roberts |
| 5,688,941 A | 11/1997 | Cook et al. |
| 5,700,922 A | 12/1997 | Cook |
| 5,714,331 A | 2/1998 | Buchard et al. |
| 5,719,262 A | 2/1998 | Buchard et al. |
| 5,750,692 A | 5/1998 | Cook et al. |
| 5,843,728 A | 12/1998 | Seed et al. |
| 5,851,828 A | 12/1998 | Seed et al. |
| 5,858,358 A | 1/1999 | June et al. |
| 5,883,223 A | 3/1999 | Gray |
| 5,906,936 A | 5/1999 | Eshhar et al. |
| 5,912,170 A | 6/1999 | Seed et al. |
| 5,912,172 A | 6/1999 | Eshhar et al. |
| 6,004,811 A | 12/1999 | Seed et al. |
| 6,040,177 A | 3/2000 | Riddell et al. |
| 6,168,587 B1 | 1/2001 | Bellhouse et al. |
| 6,194,389 B1 | 2/2001 | Johnston et al. |
| 6,284,240 B1 | 9/2001 | Seed et al. |
| 6,287,860 B1 | 9/2001 | Monia et al. |
| 6,352,694 B1 | 3/2002 | June et al. |
| 6,392,013 B1 | 5/2002 | Seed et al. |
| 6,410,014 B1 | 6/2002 | Seed et al. |
| 6,468,798 B1 | 10/2002 | Debs et al. |
| 6,471,996 B1 | 10/2002 | Sokoll et al. |
| 6,472,375 B1 | 10/2002 | Hoon et al. |
| 6,479,626 B1 | 11/2002 | Kim et al. |
| 6,489,458 B2 | 12/2002 | Hackett et al. |
| 6,534,055 B1 | 3/2003 | June et al. |
| 6,534,261 B1 | 3/2003 | Co et al. |
| 6,607,882 B1 | 8/2003 | Co et al. |
| 6,746,838 B1 | 6/2004 | Choo et al. |
| 6,753,162 B1 | 6/2004 | Seed et al. |

(56) References Cited

U.S. PATENT DOCUMENTS

| | | |
|---|---|---|
| 6,794,136 B1 | 9/2004 | Eisenberg et al. |
| 6,797,514 B2 | 9/2004 | Berenson et al. |
| 6,824,978 B1 | 11/2004 | Co et al. |
| 6,866,997 B1 | 3/2005 | Choo et al. |
| 6,867,041 B2 | 3/2005 | Berenson et al. |
| 6,887,466 B2 | 5/2005 | June et al. |
| 6,903,185 B2 | 6/2005 | Kim et al. |
| 6,905,680 B2 | 6/2005 | June et al. |
| 6,905,681 B1 | 6/2005 | June et al. |
| 6,905,874 B2 | 6/2005 | Berenson et al. |
| 6,933,113 B2 | 8/2005 | Case et al. |
| 6,979,539 B2 | 12/2005 | Co et al. |
| 7,013,219 B2 | 3/2006 | Case et al. |
| 7,030,215 B2 | 4/2006 | Liu et al. |
| 7,144,575 B2 | 12/2006 | June et al. |
| 7,148,203 B2 | 12/2006 | Hackett et al. |
| 7,160,682 B2 | 1/2007 | Hackett et al. |
| 7,175,843 B2 | 2/2007 | June et al. |
| 7,220,719 B2 | 5/2007 | Case et al. |
| 7,232,566 B2 | 6/2007 | June et al. |
| 7,241,573 B2 | 7/2007 | Choo et al. |
| 7,241,574 B2 | 7/2007 | Choo et al. |
| 7,572,631 B2 | 8/2009 | Berenson et al. |
| 7,585,849 B2 | 9/2009 | Liu et al. |
| 7,595,376 B2 | 9/2009 | Kim et al. |
| 7,741,465 B1 | 6/2010 | Eshhar et al. |
| 7,985,739 B2 | 7/2011 | Kay et al. |
| 8,021,867 B2 | 9/2011 | Smith et al. |
| 8,034,334 B2 | 10/2011 | Dudley et al. |
| 8,088,379 B2 | 1/2012 | Robbins et al. |
| 8,119,361 B2 | 2/2012 | Smith et al. |
| 8,119,381 B2 | 2/2012 | Smith et al. |
| 8,124,369 B2 | 2/2012 | Smith et al. |
| 8,129,134 B2 | 3/2012 | Smith et al. |
| 8,133,697 B2 | 3/2012 | Smith et al. |
| 8,163,514 B2 | 4/2012 | Smith et al. |
| 8,211,422 B2 | 7/2012 | Eshhar et al. |
| 8,227,432 B2 | 7/2012 | Hackett et al. |
| 8,399,645 B2 | 3/2013 | Campana et al. |
| 8,440,431 B2 | 5/2013 | Voytas et al. |
| 8,440,432 B2 | 5/2013 | Voytas et al. |
| 8,440,810 B2 | 5/2013 | Breaker et al. |
| 8,450,471 B2 | 5/2013 | Voytas et al. |
| 8,507,272 B2 | 8/2013 | Zhang et al. |
| 8,604,192 B2 | 12/2013 | Seth et al. |
| 8,637,307 B2 | 1/2014 | June et al. |
| 8,697,359 B1 | 4/2014 | Zhang |
| 8,697,663 B2 | 4/2014 | Bennett et al. |
| 8,697,854 B2 | 4/2014 | Schendel et al. |
| 8,703,728 B2 | 4/2014 | Swayze et al. |
| 8,771,945 B1 | 7/2014 | Zhang |
| 8,795,965 B2 | 8/2014 | Zhang |
| 8,796,437 B2 | 8/2014 | Swayze et al. |
| 8,865,406 B2 | 10/2014 | Zhang |
| 8,865,677 B2 | 10/2014 | Manoharan et al. |
| 8,871,445 B2 | 10/2014 | Cong et al. |
| 8,877,917 B2 | 11/2014 | Forst et al. |
| 8,883,752 B2 | 11/2014 | Swayze et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,906,682 B2 | 12/2014 | June et al. |
| 8,911,993 B2 | 12/2014 | June et al. |
| 8,916,381 B1 | 12/2014 | June et al. |
| 8,927,513 B2 | 1/2015 | Manoharan et al. |
| 8,932,814 B2 | 1/2015 | Cong et al. |
| 8,945,839 B2 | 2/2015 | Zhang |
| 8,975,071 B1 | 3/2015 | June et al. |
| 8,993,233 B2 | 3/2015 | Zhang et al. |
| 8,999,641 B2 | 4/2015 | Zhang et al. |
| 9,101,584 B2 | 8/2015 | June et al. |
| 9,102,760 B2 | 8/2015 | June et al. |
| 9,102,761 B2 | 8/2015 | June et al. |
| 9,181,527 B2 | 11/2015 | Sentman |
| 9,233,125 B2 | 1/2016 | Davila et al. |
| 2004/0224402 A1 | 11/2004 | Bonyhadi et al. |
| 2007/0191294 A1 | 8/2007 | Elmen et al. |
| 2008/0249039 A1 | 10/2008 | Elmen et al. |
| 2009/0143326 A1 | 6/2009 | Obad et al. |
| 2009/0181914 A1 | 7/2009 | Rosenbohm et al. |
| 2009/0298916 A1 | 12/2009 | Kauppinen et al. |
| 2010/0004320 A1 | 1/2010 | Elmen et al. |
| 2010/0234451 A1 | 9/2010 | Worm |
| 2010/0249052 A1 | 9/2010 | Benson et al. |
| 2010/0317718 A1 | 12/2010 | Marcusson et al. |
| 2012/0244133 A1 | 9/2012 | Rosenberg et al. |
| 2013/0071414 A1 | 3/2013 | Dotti et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2014/0342456 A1 | 11/2014 | Mali et al. |
| 2014/0356959 A1 | 12/2014 | Church et al. |
| 2015/0031132 A1 | 1/2015 | Church et al. |
| 2015/0184139 A1 | 7/2015 | Zhang et al. |
| 2015/0368342 A1 | 12/2015 | Wu et al. |
| 2015/0368360 A1 | 12/2015 | Liang et al. |
| 2016/0129109 A1 | 5/2016 | Davila et al. |
| 2016/0166613 A1 | 6/2016 | Spencer et al. |
| 2016/0175359 A1 | 6/2016 | Spencer et al. |

FOREIGN PATENT DOCUMENTS

| | | |
|---|---|---|
| EP | 2 764 103 A2 | 8/2014 |
| EP | 2 771 468 A1 | 9/2014 |
| EP | 2 784 162 A1 | 10/2014 |
| EP | 3 377 086 A1 | 9/2018 |
| WO | 89/02468 A1 | 3/1989 |
| WO | 89/05345 A1 | 6/1989 |
| WO | 89/07136 A3 | 8/1989 |
| WO | 91/06309 A1 | 5/1991 |
| WO | 92/07573 A1 | 5/1992 |
| WO | 92/15322 A1 | 9/1992 |
| WO | 93/07883 A1 | 4/1993 |
| WO | 03/020763 A2 | 3/2003 |
| WO | 03/057171 A2 | 7/2003 |
| WO | 2004/033685 A1 | 4/2004 |
| WO | 2004/044004 A2 | 5/2004 |
| WO | 2004/074322 A1 | 9/2004 |
| WO | 2005/113595 A2 | 12/2005 |
| WO | 2005/114215 A2 | 12/2005 |
| WO | 2006/000830 A2 | 1/2006 |
| WO | 2006/125962 A2 | 11/2006 |
| WO | 2008/038002 A2 | 4/2008 |
| WO | 2008/039818 A2 | 4/2008 |
| WO | 2009/114547 A2 | 9/2009 |
| WO | 2010/040112 A2 | 4/2010 |
| WO | 2010/129746 A2 | 11/2010 |
| WO | 2011/146862 A1 | 11/2011 |
| WO | 2012/079000 A1 | 6/2012 |
| WO | 2013/039889 A1 | 3/2013 |
| WO | 2013/040371 A2 | 3/2013 |
| WO | 2013/044225 A1 | 3/2013 |
| WO | 2013/166321 A1 | 11/2013 |
| WO | 2013/176915 A1 | 11/2013 |
| WO | 2014/011987 A1 | 1/2014 |
| WO | 2014/018423 A2 | 1/2014 |
| WO | 2014/018863 A1 | 1/2014 |

(56) References Cited

FOREIGN PATENT DOCUMENTS

| | | |
|---|---|---|
| WO | 2014059173 A2 | 4/2014 |
| WO | 2014/083173 A1 | 6/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/133567 A1 | 9/2014 |
| WO | 2014/133568 A1 | 9/2014 |
| WO | 2014134165 A1 | 9/2014 |
| WO | 2014172606 A1 | 10/2014 |
| WO | 2014184744 A1 | 11/2014 |
| WO | 2014191128 A1 | 12/2014 |
| WO | 2014204723 A1 | 12/2014 |
| WO | 2014204724 A1 | 12/2014 |
| WO | 2014204725 A1 | 12/2014 |
| WO | 2014204726 A1 | 12/2014 |
| WO | 2014204727 A1 | 12/2014 |
| WO | 2014204728 A1 | 12/2014 |
| WO | 2014204729 A1 | 12/2014 |
| WO | 2015057834 A1 | 4/2015 |
| WO | 2015057852 A1 | 4/2015 |
| WO | 2015058052 A1 | 4/2015 |
| WO | 2015070083 A1 | 5/2015 |
| WO | 2015089351 A1 | 6/2015 |
| WO | 2015089354 A1 | 6/2015 |
| WO | 2015089364 A1 | 6/2015 |
| WO | 2015089419 A2 | 6/2015 |
| WO | 2015089427 A1 | 6/2015 |
| WO | 2015089462 A1 | 6/2015 |
| WO | 2015089465 A1 | 6/2015 |
| WO | 2015089473 A1 | 6/2015 |
| WO | 2015089486 A2 | 6/2015 |
| WO | 2015130968 A2 | 9/2015 |
| WO | 2016000304 A1 | 1/2016 |
| WO | 2016011210 A2 | 1/2016 |
| WO | 2016049258 A2 | 3/2016 |
| WO | 2016070061 A1 | 5/2016 |
| WO | 2016094867 A1 | 6/2016 |
| WO | 2016094874 A1 | 6/2016 |
| WO | 2016106244 A1 | 6/2016 |
| WO | 2016094872 A9 | 8/2016 |
| WO | 2017087708 A1 | 5/2017 |

OTHER PUBLICATIONS

Burkett, et al., "Pouring Fuel on The Fire: Th17 Cells, The Environment, and Autoimmunity", Journal of Clinical Investigation, vol. 125, No. 6, Jun. 2015, 2211-2219.
Cho, et al., "Heterogeneity of Autoimmune Diseases: Pathophysiologic Insights from Genetics and Implications for New Therapies", Nature Medicine, vol. 21, No. 7, Jul. 2015, 730-738.
Didonna, et al., "Genetic Determinants of Risk and Progression in Multiple Sclerosis", Clinica Chimica Acta, vol. 449, Sep. 20, 2015, 16-22.
Dong, et al., "Targeting Th17 Cells in Immune Diseases", Cell Research, vol. 24, Jul. 15, 2014, 901-903.
Floss, et al., "Insights into IL-23 Biology: From Structure to Function", Cytokine & Growth Factor Reviews, vol. 26, No. 5, Oct. 2015, 569-578.
Gaublomme, et al., "Single-Cell Genomics Unveils Critical Regulators of Th17 Cell Pathogenicity", Cell, vol. 163, No. 6, Dec. 3, 2015, 1400-1412.
Korn, et al., "IL-17 and Th17 Cells", Annual Review of Immunology, vol. 27, Jan. 1, 2009, 485-517.
Kurokawa, et al., "Macrophage-derived AIM is Endocytosed into Adipocytes and Decreases Lipid Droplets via Inhibition of Fatty Acid Synthase Activity", Cell Metabolism, vol. 11, No. 6, Jun. 9, 2010, 479-492.
Langrish, et al., "IL-23 Drives s Pathogenic T Cell Population that Induces Autoimmune Inflammation", The Journal of Experimental Medicine, vol. 201, No. 2, 2005, 233-240.
Lee, et al., "Induction and Molecular Signature of Pathogenic Th17 Cells", Nature Immunology, vol. 13, No. 10, Oct. 2012, 991-999.
Lock, et al., "Gene-Microarray Analysis of Multiple Sclerosis Lesions Yields New Targets Validated in Autoimmune Encephalomyelitis", Nature Medicine, vol. 8, No. 5, May 2002, 500-508.
Miyazaki, et al., "Increased Susceptibility of Thymocytes to Apoptosis in Mice Lacking AIM, a Novel Murine Macrophage-derived Soluble Factor Belonging to the Scavenger Receptor Cysteine-rich Domain Superfamily", The Journal of Experimental Medicine, vol. 189, No. 2, Jan. 18, 1999, 413-422.
Stumhofer, et al., "Interleukins 27 and 6 Induce Stat3-Mediated T Cell Production of Interleukin 10", Nature Immunology, vol. 8, No. 12, 2007, 1363-1371.
Teng, et al., "IL-12 and IL-23 Cytokines: From Discovery to Targeted Therapies for Immune-Mediated Inflammatory Diseases", Nature Medicine, vol. 21, No. 7, Jul. 2015, 719-729.
Waite, et al., "Th17 Response and Inflammatory Autoimmune Diseases", International Journal of Inflammation, vol. 2012, Article ID 819467, 2012, 10 pages.
Wang, et al., "CD5L/AIM Regulates Lipid Biosynthesis and Restrains Th17 Cell Pathogenicity", Cell, vol. 163, No. 6, 2015, 1413-1427.
Wang, et al., "The I-23 To IL-17 Cascade Inflammation-Related Cancers", Clinical and Experimental Rheumatology, vol. 33, Jul.-Aug. 2015, S87-S90.
Ye, et al., "The Role and Regulation of Human Th17 Cells In Tumor Immunity", The American Journal of Pathology, vol. 182, No. 1, Jan. 2013, 10-20.
Yosef, et al., "Dynamic Regulatory Network Controlling Th17 Cell Differentiation", Nature, vol. 496, No. 7446, Apr. 25, 2013, 461-468.
Zambrano-Zaragoza, et al., "Th17 Cells in Autoimmune and Infectious Diseases", International Journal of Inflammation, vol. 2014, Article. 651503, Aug. 3, 2014, 12 pages.
Han, et al., "Th17 Cells in Autoimmune Diseases", Frontiers of Medicine, vol. 9, Issue 1, Mar. 10-19, 2015,—Abstract only.
The Brigham and Women's Hospital, Inc., "Office Action for Canadian Patent Application No. 3,005,878", dated Apr. 22, 2020, 4 pages.
Massachusetts Institute of Technology, et al., "Examination Report No. 1 for Standard Patent Application for AU 2016355178", dated Feb. 25, 2019, 3 pages.
The Brigham and Women's Hospital, Inc., et al., "First Office Action for CA 3,005,878", dated Mar. 12, 2019, 4 pages.
The Brigham and Women's Hospital, Inc., "Communication pursuant to Article 94(3) EPC for EP 16816778.1", dated Nov. 19, 2020, 4 pages.
Abdi et al., "Free IL-12p40 monomer is a polyfunctional adaptor for generating novel IL-12-like heterodimers extracellularly", The Journal of Immunology, 2014, vol. 192, pp. 6038-6036.
Martinez et al., "The conserved scavenger receptor cysteine-rich superfamily in therapy and diagnosis", Pharmacological Reviews, American Society for Pharmacology and Experimental Therapeutics, 2011, vol. 63, No. 4, pp. 967-1000.
Sanjurjo et al., "AIM/CD5L: a key protein in the control of immune homeostasis and inflammatory disease", Journal of Leukocyte Biology, 2015, vol. 98, pp. 173-184.
Sanjurjo et al., "The human CD5L/AIM-CD36 axis: a novel autophagy inducer in macrophages that modulates inflammatory responses", Autophagy, Mar. 2015, vol. 11, No. 3, pp. 487-502.
Yusa et al., "AIM, a murine apoptosis inhibitory factor, induces strong and sustained growth inhibition of B lymphocytes in combination with TGF-beta1", European Journal of Immunology, Apr. 1999, vol. 29, No. 4, pp. 1086-1093.
International Search Report issued in International Patent Application No. PCT/US2016/062592, dated Apr. 4, 2017.

Unique to CD5Lm/p40 mixture

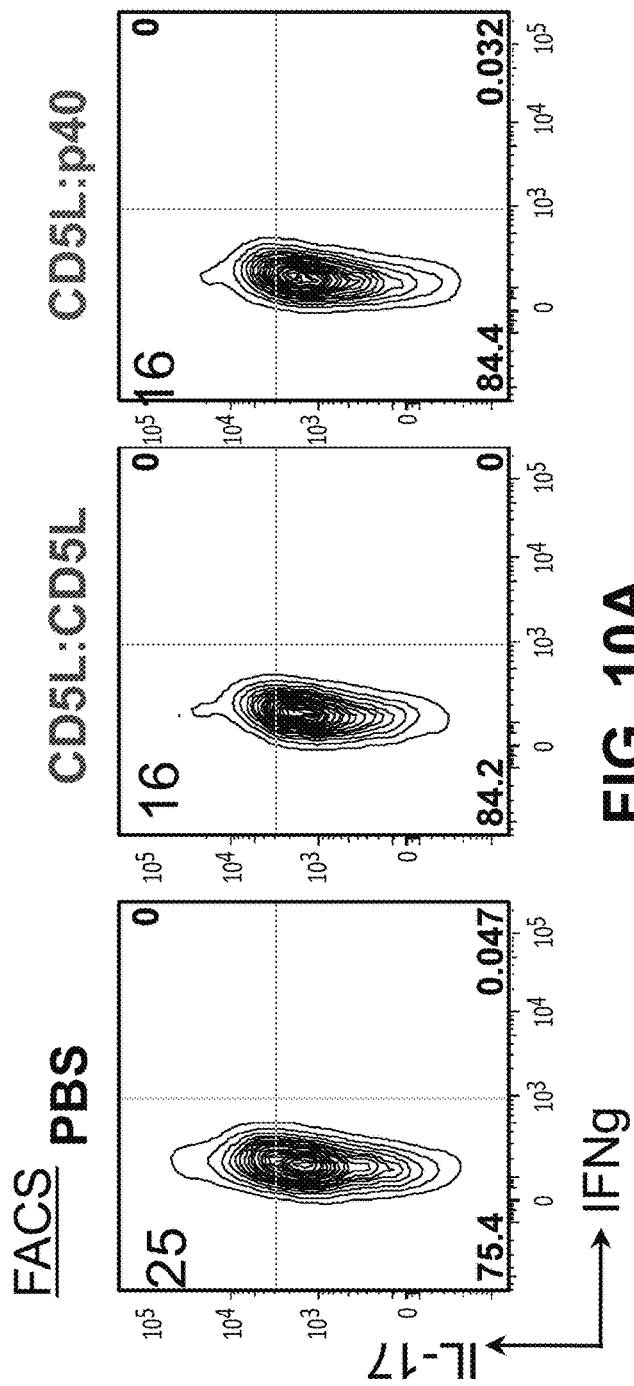
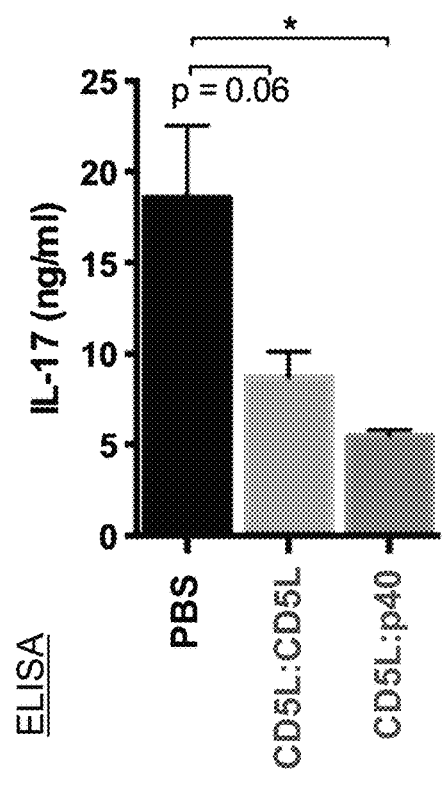
FIG. 10A
FIG. 10B

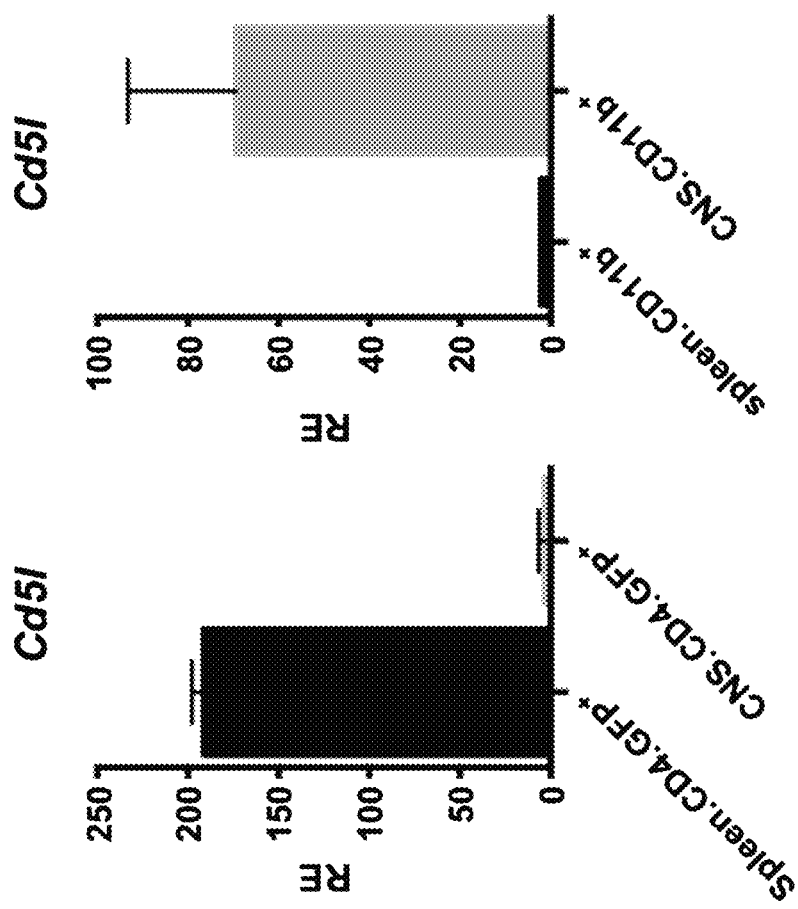
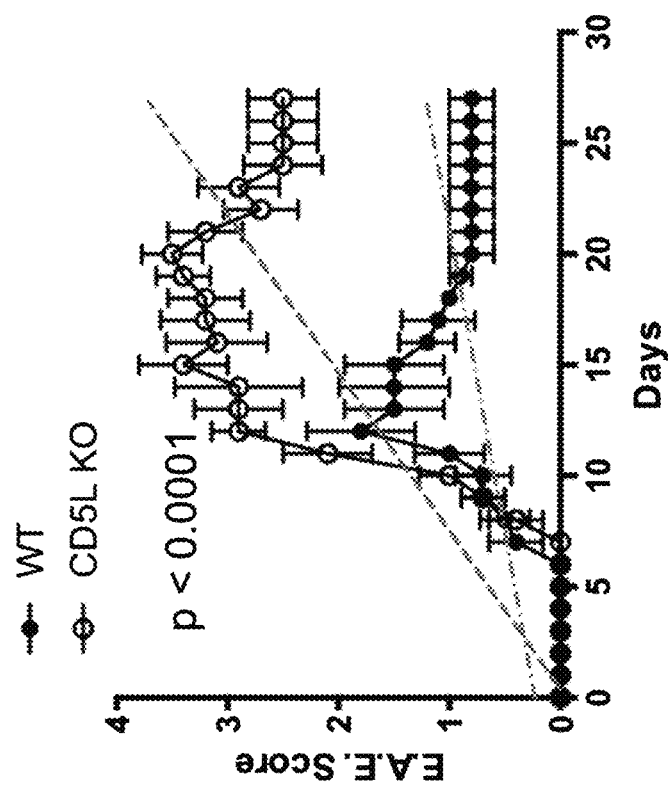
FIG. 13A
FIG. 13B

| | | | |
|---|---|---|---|
| Mouse | 1 | MLDCRAVIMLWLLPWVTQGLAVPRSSSPDWAQCQQLSRNLCMLAWNAHAPAGHMNLLREEDEETKNVPRIQCEDGCDP | 80 |
| Human | 1 | MLGSRAVMLLLLLPWTAQGRAVPGGSSPAWTQCQQLSQKLCTLAWSAHPLVCHMDLREEGDEETTNDVPHIQCGDGCDP | 79 |
| Mouse | 81 | QGLKDNSQFCLQRIRQGLAFYKHLLDSDIFKGEPALLPDSPMEQLHTSLLGLSQLLQPEDHPRETQQMPSLSSSQWQRP | 160 |
| Human | 80 | QGLRDNSQFCLQRIHQGLIFYEKLLGSDIFTGEPSLLPDSPVGQLHASLLGLSQLLQPEGHHWETQQIPSLSPSQPWQRL | 159 |
| Mouse | 161 | LLRSKILRSLQAFLAIAARVPAHGAAELTEPLVPPA | 196 |
| Human | 160 | LLRFKILRSLQAFVAVAARVPAHGAAPLS-P----- | 189 |

| | | |
|---|---|---|
| Mouse | 1 | MCPQKLTISWFAIVLLVSPLMAMWELEKDVYVVEVDWTPDAPGETVNLTCDTPEEDDITWTSDQRHGVIQSGKTLTITVK | 80 |
| Human | 1 | MCHQQLVISWFSLVFLASPLVAIWELKKDVYVVELDWYPDAPGEMVVLTCDTPEEDGITWTLDQSSEVLGSGKTLTIQVK | 80 |
| Mouse | 81 | EFLDAGQYTCHKGGETLSHSHLLLHKKENGIWSTEILKNF----KNKTFLKCEAPNYSGRFTCSWLVQRNMDLKFNIKSSS | 157 |
| Human | 81 | EFGDAGQYTCHKGGEVLSHSLLLLHKKEDGIWSTDILKDQKEPKNKTFLRCEAKNYSGRFTCWWLTTISTDLTFSVKSSR | 160 |
| Mouse | 158 | SSPDSRAVTCGMASLSAEKVTLDQRDYEKYSVSCQEDVTCPTAEETLPIELALEARQQNKYENYSTSFFIRDIIKPDPPK | 237 |
| Human | 161 | GSSDPQGVTCGAATLSAERVRGDNKEYE-YSVECQEDSACPAAEESLPIEVMVDAVHKLKYENYTSSFFIRDIIKPDPPK | 239 |
| Mouse | 238 | NLQMKPLKNSQVEVSWEYPDSWSTPHSYFSLKFFVRIQRKKEKMKETEEGCNQKGAFLVEKTSTEVQC--KGGNVCVQAQ | 315 |
| Human | 240 | NLQLKPLKNSRQVEVSWEYPDTWSTPHSYFSLTFCVQVQGKSKREK---------KDRVFTDKTSATVICRKNASISVRAQ | 311 |
| Mouse | 316 | DRYYNSSCSKWACVPCRVRS | 335 |
| Human | 312 | DRYYSSSWSEWASVPC---S | 328 |

```
Mouse   1                                     ------MCQSRYLLFLATLALLNHLSRARVIPVSGP------AKCLNQSQMLLK    42
Human   1   MWPPGSASQPPPSPAAATGLHPAARPVSLQCRLSMCPARSLLLVATLVLLDHLSLARNLPVATPDPGMFPCLHHSQNLLR    80

Mouse  43   TTDDMVRTAREKLKHYSCTAEDIDHEDITRDQTSTLRTCLPLELHKNESCLATRETSSTTRGSCLPPQKTSLMMTLCLGS   122
Human  81   AVSNMLQKARQTLEFYPCTSEEIDHEDITKDKTSTVEACLPLELTKNESCLNSRETSFITNGSCLASRKTSFMMALCLSS   160

Mouse 123   IYEDLKMYQTEFQAINAALQSHNHQQIIILDKMAIDELMRSLHSGETLRQKAPMGEADPYRVMKLCILLHAFSTRV     202
Human 161   IYEDLKMYQVEFKTMNAKLLMDPKRQIFLDQNMLAVIDELMQALNFNSETVPQKSSLEEPDFYKTKIKLCILLHAFRIRA   240

Mouse 203   VTINRVMSYLNAS                                                                    215
Human 241   VTIDRVMSYLNAS                                                                    253
```

METHOD OF TREATING AUTOIMMUNE DISEASE WITH LYMPHOCYTE ANTIGEN CD5-LIKE (CD5L) PROTEIN

RELATED APPLICATIONS AND INCORPORATION BY REFERENCE

This application is a continuation of U.S. patent application Ser. No. 15/777,054, filed May 17, 2018, which is a national stage entry of International Application Number PCT/2016/062592, filed on Nov. 17, 2016, which claims priority to U.S. Provisional Patent Application 62/257,589, filed Nov. 19, 2015, all of which are hereby incorporated herein by reference.

FEDERALLY SPONSORED RESEARCH OR DEVELOPMENT

This invention was made with Government support under Grant Nos. P01 AI056299, P01 AI039671, P01 AI073748, and 5P01 AI045757 awarded by the National Institutes of Health. The Government has certain rights in the invention.

TECHNICAL FIELD

Described herein are methods for suppressing or enhancing an immune response in a subject.

BACKGROUND

The cytokine environment influences immune cell differentiation, function and plasticity. IL-23 has been identified as key player in inflammatory diseases, contributing largely to mucosal inflammation. It was discovered as a susceptibility gene in GWAS and is widely implicated in autoimmune diseases and cancer such as melanoma and colorectal carcinoma (Burkett et al., 2015; Cho and Feldman, 2015; Teng et al., 2015; Wang and Karin, 2015).

SUMMARY

The present invention is based, at least in part, on the discovery that CD5L and p40 form heterodimers in vivo, and that these heterodimers modulate the immune response. CD5L exists as a monomer, and is also able to form dimers; both forms may also serve as immunomodulators. Some embodiments comprise methods for modulating an immune response or suppressing an immune response (e.g., an inflammatory immune response) in a subject, the method comprising administering to the subject a therapeutically effective amount of recombinant soluble CD5L, a CD5L:CD5L homodimer, a CD5L:p40 heterodimer, or one or more nucleic acids encoding the same. In some embodiments, the subject has an autoimmune disease, e.g., Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, or diabetes. In some embodiments, the subject has an inflammation-related cancer, e.g., colorectal cancer, carcinogen-induced skin papilloma, fibrosarcoma, or mammary carcinomas.

Some embodiments comprise methods of suppressing an immune response in a subject, the method comprising administering to the subject a therapeutically effective amount of one or more of: a recombinant soluble CD5L and/or a nucleic acid encoding CD5L; a recombinant soluble CD5L:CD5L homodimer and/or a nucleic acid encoding a CD5L homodimer; and a recombinant soluble CD5L:p40 heterodimer and/or nucleic acids encoding CD5L and p40. In some embodiments the subject has an autoimmune disease, such as Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, or diabetes. In some embodiments, subject has an inflammation-related cancer, such as colorectal cancer, carcinogen-induced skin papilloma, fibrosarcoma, or mammary carcinomas.

Some embodiments comprise administering the CD4L:p40 heterodimer. Some embodiments comprise administering the CD5L:CD5L homodimer.

Some embodiments relate to methods of enhancing an immune response in a subject, the method comprising administering to the subject a therapeutically effective amount of an agent that: (a) inhibits CD5L, a CD5L:CD5L homodimer, and/or a CD5L:p40 heterodimer from binding to an IL-23 receptor; and/or (b) inhibits formation of the CD5L:CD5L homodimer and/or the CD5L:p40 heterodimer. In some embodiments, the agent comprises an antibody, or an antigen binding fragment thereof, that binds to one or more of the CD5L, the CD5L homodimer, or the CD5L:p40 heterodimer. In some embodiments, the agent comprises inhibitory nucleic acids that target the CD5L and/or the p40.

In some embodiments, the subject has cancer that is not inflammation related. Some embodiments comprise administering an anti-cancer immunotherapy to the subject, such as checkpoint inhibitors, PD-1/PDL-1, anti-cancer vaccines, adoptive T cell therapy, and/or combination of two or more thereof.

In embodiments that comprise administering inhibitory nucleic acids, the nucleic acids can include small interfering RNAs (e.g., shRNA), antisense oligonucleotides (e.g. antisense RNAs), and/or CRISPR-Cas.

In some embodiments, the subject has an immune deficiency, e.g., a primary or secondary immune deficiency. In some embodiments, the subject has an infection with a pathogen, e.g., viral, bacterial, or fungal pathogen.

Some embodiments comprised methods of modulating $CD8^+$ T cell exhaustion in a subject in need thereof, the method comprising administering to the subject a therapeutically effective amount of an agent that: (a) inhibits CD5L, a CD5L:CD5L homodimer, and/or a CD5L:p40 heterodimer from binding to an IL-23 receptor; and/or (b) inhibits formation of the CD5L:CD5L homodimer and/or the CD5L:p40 heterodimer. In some embodiments, said administering reduces $CD8^+$ T cell exhaustion. In some embodiments the subject has cancer, such as a non-inflammatory cancer.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

The patent or application file contains at least one drawing executed in color. Copies of this patent or patent application publication with color drawing(s) will be provided by the Office upon request and payment of the necessary fee.

FIG. 4A-4D. Naïve 6-month old mice that are either wildtype or CD5L$^{−/−}$ were sacrificed and cells from tissues as indicated are analyzed by flow cytometry or quantitative real time PCR. (A) IL-23R.GFP$^{+/−}$ reporter mice that are otherwise wildtype or CD5L$^{−/−}$ were used and cells were stained directly ex vivo; (FIG. 4B-FIG. 4C) Cells were incubated with IL-7 or IL-7/CD5L overnight and restimulated with PMA/ionomycin in the presence of brefeldin A for four hours. Cells were subsequently stained and analyzed by flow cytometry; (FIG. 4D) Cells were analyzed directly ex vivo by flow cytometry or sorted, RNA-extracted and analyzed by real time qPCR; (FIG. 4E-4G) 6-8 wk old WT or CD5L$^{−/−}$ IL-17$^{Cre}$Rosa26$^{Td-tomato}$ mice were treated with 2.5% DSS in drinking water for 6 days followed by 5 days of regular water. Mice were then sacrificed and cells isolated from respective tissues for PMA/ionomycin restimulation and flow cytometry analysis.

FIG. 7A) Th0, Th1 (IL-12) and Th17p (IL-1b, IL-6, IL-23) are differentiated from naïve CD4 T cells in vitro for 4 days and cells were harvested for staining with recombinant CD5L followed by anti-His APC antibodies and flow cytometry analysis. FIG. 7B) Wildtype (WT) mice were immunized with MOG/CFA followed by PT injection to induce EAE. Mice at peak of disease (score=3) were injected with either PBS (solid circles) or recombinant CD5L (empty circles, CD5Lm) intraperitoneally daily for five consecutive days and mice were followed for disease progression. FIG. 7C) WT mice were induced with colitis with 2.5% DSS in drinking water for a consecutive of 6 days followed by normal water for 8 days. Mice were given either control (PBS) or recombinant CD5L (CD5Lm) intraperitoneally on day 4, 6 and 8. Colon length and colitis score are recorded on day 14.

(FIG. 8A) Recombinant CD5L and CD5L: p40 (genetically linked) were custom ordered from Biolegend. CD5L monomer formed a homodimer and CD5L: CD5L homodimer, which was further purified and was used in subsequent experiments to test its function separately; (FIG. 8B) Serum was collected kinetically from WT and Cd5l$^{−/−}$ mice with DSS-induced colitis (2% DSS in drinking water for 6 days followed by 7 days of normal water) and the level of CD5L:p40 was measured using an ELISA developed in house using anti-p40 antibody for capturing, biotinylated anti-CD5L antibody for detection and recombinant CD5L:p40 as a positive control.

FIG. 9A sets forth results of a screening assay showing that TLR ligands can induce secretion of CD5L:p40. FIG. 9B sets forth flow cytometry experiments showing that IL-27 induces expression of CD5L.

FIGS. 10A-D. FIG. 10A sets forth results of FACS experiments showing that CD5L homodimers and CD5L: p40 heterodimers inhibit IL-17 expression in pathogenic Th17 cells; FIG. 10B shows results of an serum ELISA measurements showing that both forms of CD5L inhibit IL-17 expression; FIG. 10C and FIG. 10D show cell signatures for pathogenic Th17 cells treated with CD5L homodimers and CD5L:p40 heterodimers, respectively.

FIG. 11A shows inhibited IL-27 expression in pathogenic Th17 cells treated with CD5L homodimers and CD5L:p40 heterodimers, as measured by ELISA and qPCR; FIG. 11B shows that IFNg expression in Th1 cells is inhibited by CD5L:CD5L homodimer and CD5L:p40 heterodimer, as measured by flow cytometry analysis.

FIG. 12A and FIG. 12B show heat maps and GSEA analysis for Th17 cells and Th1 cells, respectively, following treatment with CD5L homodimers and CD5L:p40 heterodimers.

FIGS. 13A-B. FIG. 13A compares EAE disease severity measurements in wildtype mice and CD5L knockout mice; FIG. 13B compares CD5L expression levels in Th17 and macrophage cells in the spleen and CNS.

FIG. 14A shows a construct used to generate CD5L conditional knockout mice; FIG. 14B shows that mice CD5L deletion mice were produced in myeloid lineage cells, T cells, and IL-17 producing cells.

FIG. 15A sets forth a plot demonstrating tumor growth in CD5L$^{flox/flox}$Lymx$^{Cre+}$ mice injected with colon carcinoma; FIG. 15B sets forth pictures showing tumor size in CD5L$^{flox/flox}$ mice and CD5L knockout mice 19 days after tumor injection.

FIG. 18A and FIG. 18B sets forth plots showing suppression of tumor progression in CD5L$^{−/−}$ mice injected with MC38 (FIG. 19A) and MC38-OVA (FIG. 19B) colon carcinoma; FIG. 18C and FIG. 18D set forth flow cytometry diagrams assessing tumor infiltrating lymphocytes and cytokines, respectively, in CD5L$^{−/−}$ mice and control mice.

FIG. 19 sets forth graphs showing CD5L: CD5L homodimer expression (FIG. 19A) and CD5L:p40 heterodimer expression (FIG. 19B) in serum during tumor progression, as measured using ELISA assays.

FIGS. 21A-FIG. 21B set forth data showing the impact of CD5L:p40 and CD5L:CD5L on Tregs in vivo in DSS-induced colitis; FIG. 21A shows frequency of Foxp3+CD4 T cells in cells from mesenteric lymph node (mLN), peyer's patches (pp), Lamina propria of colon (LP), and intraepithelial lymphocytes (IEL); FIG. 21B sets forth data showing that CD5L:p40 decreased ILC3 in Lamina propria cells.

FIG. 22A sets forth data showing serum concentrations of CD5L:p40 and CD5L:CD5L in mice immunized with CD5L:p40 and CD5L:CD5L, respectively; FIG. 22B sets forth data showing pools of antibodies specific to either CD5L:p40 or CD5L:CD5L, and which were obtained from mice immunized with CD5L:p40 and CD5L:CD5L, respectively.

FIGS. 23A-D. FIG. 23 demonstrates homology between mice and human protein sequences for CD5L (FIG. 23A), p19 (FIG. 23B), p40 (FIG. 23C), and p35 (FIG. 23D).

DETAILED DESCRIPTION

Figure 1:
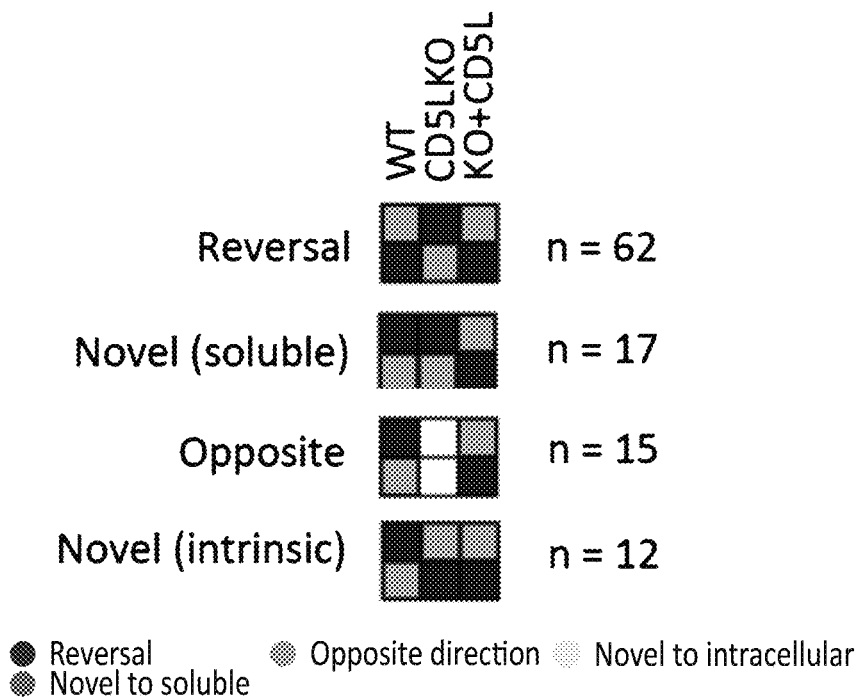
FIG. 1. Soluble CD5L can regulate T cell function, largely reversing CD5L deficiency-induced gene expression pattern in T cells. WT or CD5L−/− naïve T cells were sorted and activated under Th0 condition and treated with either PBS or soluble CD5L (50 nM). RNA was extracted at 96 h and analyzed using nanostring platform using Th17 codesets of 312 genes (only those showing a difference between any of the tested conditions were included in further analysis).
Figure 1:
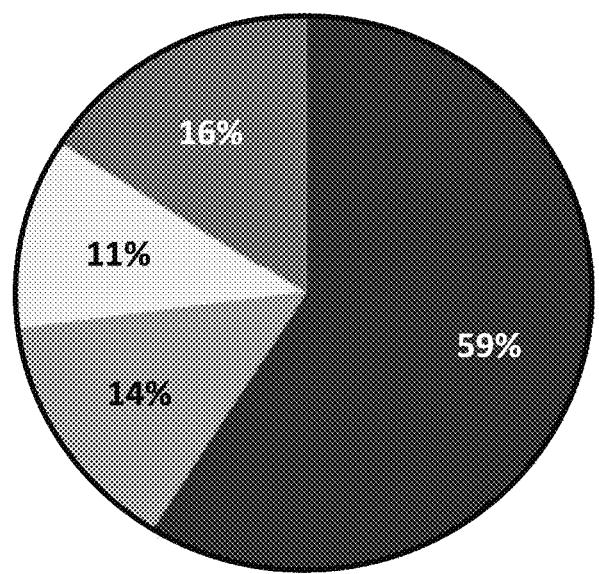
Figure 1:
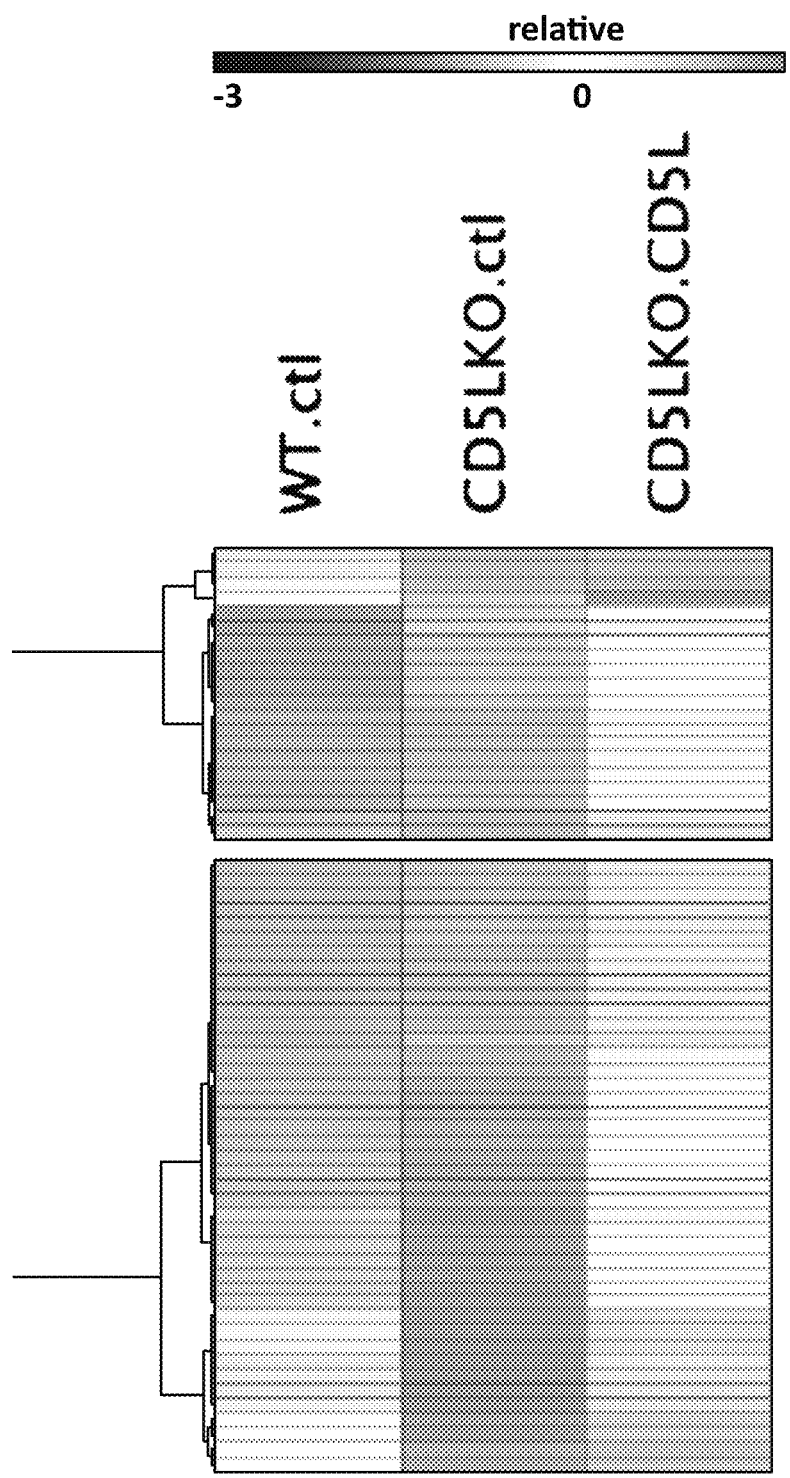

Interleukin 23 (IL-23) is formed of a heterodimer by p19 and p40. p40, also known as interleukin 12B, can form heterodimers with two other cytokines: p35 to make IL-12 and potentially CD5 Antigen Like protein (CD5L) (also known as apoptosis inhibitor of macrophage (AIM), SP-a, and Api6) to make CD5L:p40. It has not previously been demonstrated that the CD5L:p40 dimer has any function. Th17-cell intrinsic CD5L can regulate Th17 cell pathogenicity and regulate IL-23R expression (see WO2015130968). CD5L is a secreted protein and it may form a heterodimer with p40 (Abdi et al., 2014). Applicants tested the hypothesis that soluble CD5L, as a monomer, homodimer, or heterodimer with p40, can function as a cytokine regulating T cell function. Surprisingly, Applicants found that soluble CD5L, CD5L:CD5L homodimer, and CD5L:p40 heterodimer share a distinct ability to regulate T cell function. Not to be bound by theory, CD5L, either as a monomer, homodimer, or a heterodimer, is suspected to interfere with the pathogenic and non-pathogenic program of Th17 cells. Such findings have therapeutic implications with respect to neuroinflammation, autoimmune disorders, inflammatory cancers, and non-inflammatory cancers and disorders, inter alia.

CD5L function is largely dependent not on CD36, the known receptor for CD5L, but IL-23R expression on T cells. Further, CD5L:p40 appears to be less dependent on IL-23R and may require a different receptor for signaling. Moreover, CD5L can regulate not only T cells, but also other IL-23R expressing cells such as innate lymphoid cells and dendritic cells. CD5L plays a critical role in protecting host from acute inflammation and potentially tumor progression.

CD5L Proteins and CD5L:p40 Heterodimers

In some embodiments, the methods described herein can include the administration of soluble CD5L, CD5L:CD5L homodimers, or CD5L:p40 heterodimers. The homodimers include CD5L complexed to another CD5L, preferably complexed together in a homodimeric form. The heterodimers include p40 protein and CD5L protein, preferably complexed together in a heterodimeric form. The protein sequences will preferably be chosen based on the species of the recipient; thus, for example, human p40 and/or human CD5L can be used to treat a human subject. The sequences of human p40 and CD5L are as follows:

```
Human p40 (interleukin-12 subunit beta) precursor
                                                          (SEQ ID NO: 1)
  1    mchqqlvisw  fslvflaspl  vaiwelkkdv  yvveldwypd  apgemvvltc  dtpeedgitw
 61    tldqssevlg  sgktltiqvk  efgdaggytc  hkggevlshs  llllhkkedg  iwstdilkdq
121    kepknktflr  ceaknysgrf  tcwwlttist  dltfsvkssr  gssdpqgvtc  gaatlsaerv
181    rgdnkeyeys  vecqedsacp  aaeeslpiev  mvdavhklky  enytssffir  diikpdppkn
241    lqlkplknsr  qvevsweypd  twstphsyfs  ltfcvqvqgk  skrekkdrvf  tdktsatvic
301    rknasisvra  qdryysssws  ewasvpcs
```

In some embodiments, amino acids 23-328 of SEQ ID NO:1 (leaving off the signal sequence) are used. An exemplary mRNA sequence encoding p40 is accessible in GenBank at No. NM_002187.2.

```
CD5 molecule-like (CD5L)
                                                          (SEQ ID NO: 2)
  1    mallfslila  ictrpgflas  psgvrlvggl  hrcegrveve  qkgqwgtvcd  dgwdikdvav
 61    lcrelgcgaa  sgtpsgilye  ppaekeqkvl  igsvsctgte  dtlagcegee  vydcshdeda
121    gascenpess  fspvpegvrl  adgpghckgr  vevkhqnqwy  tvcqtgwslr  aakvvcrqlg
181    cgravltqkr  cnkhaygrkp  iwlsqmscsg  reatlqdcps  gpwgkntcnh  dedtwveced
241    pfdlrlvggd  nlcsgrlevl  hkgvwgsvcd  dnwgekedqv  vckqlgcgks  lspsfrdrkc
301    ygpgvgriwl  dnvrcsgeeq  sleqcqhrfw  gfhdcthqed  vavicsg
```

In some embodiments, amino acids 20-347 of SEQ ID NO:2 (leaving off the signal sequence) are used. An exemplary mRNA sequence encoding CD5L is accessible in GenBank at No. NM_005894.2.

Methods for making recombinant proteins are well known in the art, including in vitro translation and expression in a suitable host cell from nucleic acid encoding the variant protein. A number of methods are known in the art for producing proteins. For example, the proteins can be produced in and purified from yeast, *E. coli*, insect cell lines, plants, transgenic animals, or cultured mammalian cells; see, e.g., Palomares et al., "Production of Recombinant Proteins: Challenges and Solutions," Methods Mol Biol. 2004; 267: 15-52. In some embodiments, recombinant p40 and CD5L proteins are obtained and mixed in roughly equimolar amounts of p40 with CD5L and incubated, e.g., at 37° C. Immunoprecipitation and purification can be used to confirm formation of heterodimers, as can size exclusion chromatography or other purification methods, to obtain a substantially pure population of heterodimers. In some embodiments, p40 and CD5L are simply mixed together under conditions sufficient for heterodimerization, and optionally purified to obtain a substantially pure composition of heterodimers; alternatively, the heterodimers can be cross-linked and then purified. In some embodiments, an agent such as TLR9 can be used to increase heterodimer formation, e.g., in vitro or in vivo.

In some embodiments, the methods include administering nucleic acids encoding a p40 and/or CD5L polypeptides or active fragment thereof. In some embodiments, the nucleic acids are incorporated into a gene construct to be used as a part of a gene therapy or cell therapy protocol. In some embodiments, the methods include targeted expression vectors for transfection and expression of polynucleotides that encode p40 and/or CD5L polypeptides as described herein, in particular cell types, especially in T cells. Expression constructs of such components can be administered in any effective carrier, e.g., any formulation or composition capable of effectively delivering the component gene to cells in vivo. Approaches include insertion of the gene in viral vectors, including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered naked or with the help of, for example, cationic liposomes (lipofectamine) or derivatized conjugates (e.g., antibody conjugated), polylysine conjugates, gramicidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g., a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells that have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, Blood 76:271 (1990)). A replication defective retrovirus can be packaged into virions, which can be used to infect a target cell through the use of a helper virus by standard techniques. Protocols for producing recombinant retroviruses and for infecting cells in vitro or in vivo with such viruses can be found in Ausubel, et al., eds., Current Protocols in Molecular Biology, Greene Publishing Associates, (1989), Sections 9.10-9.14, and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include ΨCrip, ΨCre, Ψ2 and ΨAm. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. Nos. 4,868,116; 4,980,286; PCT Application WO 89/07136; PCT Application WO 89/02468; PCT Application WO 89/05345; and PCT Application WO 92/07573).

Another viral gene delivery system useful in the present methods utilizes adenovirus-derived vectors. The genome of an adenovirus can be manipulated, such that it encodes and expresses a gene product of interest but is inactivated in terms of its ability to replicate in a normal lytic viral life cycle. See, for example, Berkner et al., BioTechniques 6:616 (1988); Rosenfeld et al., Science 252:431-434 (1991); and Rosenfeld et al., Cell 68:143-155 (1992). Suitable adenoviral vectors derived from the adenovirus strain Ad type 5 d1324 or other strains of adenovirus (e.g., Ad2, Ad3, or Ad7 etc.) are known to those skilled in the art. Recombinant adenoviruses can be advantageous in certain circumstances, in that they are not capable of infecting non-dividing cells and can be used to infect a wide variety of cell types, including epithelial cells (Rosenfeld et al., (1992) supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ, where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al., supra; Haj-Ahmand and Graham, J. Virol. 57:267 (1986)).

Yet another viral vector system useful for delivery of nucleic acids is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al., Curr. Topics in Micro. and Immunol. 158:97-129 (1992)). It is also one of the few viruses that may integrate its DNA into non-dividing cells, and exhibits a high frequency of stable integration (see for example Flotte et al., Am. J. Respir. Cell. Mol. Biol. 7:349-356 (1992); Samulski et al., J. Virol. 63:3822-3828 (1989); and McLaughlin et al., J. Virol. 62:1963-1973 (1989)). Vectors containing as little as 300 base pairs of AAV can be packaged and can integrate. Space for exogenous DNA is limited to about 4.5 kb. An AAV vector such as that described in Tratschin et al., Mol. Cell. Biol. 5:3251-3260 (1985) can be used to introduce DNA into cells. A variety of nucleic acids have been introduced into different cell types using AAV vectors (see for example Hermonat et al., Proc. Natl. Acad. Sci. USA 81:6466-6470 (1984); Tratschin et al., Mol. Cell. Biol. 4:2072-2081 (1985); Wondisford et al., Mol. Endocrinol. 2:32-39 (1988); Tratschin et al., J. Virol. 51:611-619 (1984); and Flotte et al., J. Biol. Chem. 268:3781-3790 (1993)).

In addition to viral transfer methods, such as those illustrated above, non-viral methods can also be employed to cause expression of a nucleic acid compound described herein (e.g., nucleic acids encoding p40 and/or CD5L polypeptides) in the tissue of a subject. Typically non-viral methods of gene transfer rely on the normal mechanisms used by mammalian cells for the uptake and intracellular transport of macromolecules. In some embodiments, non-viral gene delivery systems can rely on endocytic pathways for the uptake of the subject gene by the targeted cell. Exemplary gene delivery systems of this type include liposomal derived systems, poly-lysine conjugates, and artificial viral envelopes. Other embodiments include plasmid injection systems such as are described in Meuli et al., J. Invest. Dermatol. 116(1):131-135 (2001); Cohen et al., Gene Ther. 7(22):1896-905 (2000); or Tam et al., Gene Ther. 7(21): 1867-74 (2000).

In some embodiments, genes encoding p40 and/or CD5L polypeptides are entrapped in liposomes bearing positive charges on their surface (e.g., lipofectins), which can be tagged with antibodies against cell surface antigens of the target tissue (see, e.g., Mizuno et al., No Shinkei Geka 20:547-551 (1992); PCT publication WO91/06309; Japanese patent application 1047381; and European patent publication EP-A-43075)).

In clinical settings, the gene delivery systems for the therapeutic gene can be introduced into a subject by any of a number of methods, each of which is familiar in the art. For instance, a pharmaceutical preparation of the gene delivery system can be introduced systemically, e.g., by intravenous injection, and specific transduction of the protein in the target cells will occur predominantly from specificity of transfection, provided by the gene delivery vehicle, cell-type or tissue-type expression due to the transcriptional regulatory sequences controlling expression of the receptor gene, or a combination thereof. In other embodiments, initial delivery of the recombinant gene is more limited, with introduction into the subject being quite localized. For example, the gene delivery vehicle can be introduced by catheter (see U.S. Pat. No. 5,328,470) or by stereotactic injection (e.g., Chen et al., PNAS USA 91: 3054-3057 (1994)).

The pharmaceutical preparation of the gene therapy construct can consist essentially of the gene delivery system in an acceptable diluent, or can comprise a slow release matrix in which the gene delivery vehicle is embedded. Alternatively, where the complete gene delivery system can be produced intact from recombinant cells, e.g., retroviral vectors, the pharmaceutical preparation can comprise one or more cells, which produce the gene delivery system.

Pharmaceutical Compositions

The methods described herein include the manufacture and use of pharmaceutical compositions, which include an agent described herein as active ingredient(s). Also included are the pharmaceutical compositions themselves.

Pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, and combinations of two or more thereof, compatible with pharmaceutical administration. Supplementary active compounds can also be incorporated into the compositions.

Pharmaceutical compositions are typically formulated to be compatible with the intended route of administration. Examples of routes of administration that are especially useful in the present methods include parenteral (e.g., intravenous), intrathecal, oral, and nasal or intranasal (e.g., by administration as drops or inhalation) administration. In some embodiments, such as for compounds that don't cross the blood brain barrier, delivery directly into the CNS or CSF can be used, e.g., using implanted intrathecal pumps (see, e.g., Borrini et al., Archives of Physical Medicine and Rehabilitation 2014; 95:1032-8; Penn et al., N. Eng. J. Med. 320:1517-21 (1989); and Rezai et al., Pain Physician 2013; 16:415-417) or nanoparticles, e.g., gold nanoparticles (e.g., glucose-coated gold nanoparticles, see, e.g., Gromnicova et al. (2013) PLoS ONE 8(12): e81043). Methods of formulating and delivering suitable pharmaceutical compositions are known in the art, see, e.g., the books in the series Drugs and the Pharmaceutical Sciences: a Series of Textbooks and Monographs (Dekker, NY); and Allen et al., Ansel's Pharmaceutical Dosage Forms and Drug Delivery Systems, Lippincott Williams & Wilkins; 8th edition (2004).

Pharmaceutical compositions suitable for injectable use can include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, NJ) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

For oral administration, the compositions can be formulated with an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Therapeutic compounds that are or include nucleic acids can be administered by any method suitable for administration of nucleic acid agents, such as a DNA vaccine. These methods include gene guns, bio injectors, and skin patches as well as needle-free methods such as the micro-particle DNA vaccine technology disclosed in U.S. Pat. No. 6,194,389, and the mammalian transdermal needle-free vaccination with powder-form vaccine as disclosed in U.S. Pat. No. 6,168,587. Additionally, intranasal delivery is possible, as described in, inter alia, Hamajima et al., Clin. Immunol. Immunopathol., 88(2), 205-10 (1998).

Liposomes (e.g., as described in U.S. Pat. No. 6,472,375) and microencapsulation can also be used to deliver a compound described herein. Biodegradable microparticle delivery systems can also be used (e.g., as described in U.S. Pat. No. 6,471,996).

In one embodiment, the therapeutic compounds are prepared with carriers that will protect the therapeutic compounds against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Such formulations can be prepared using standard techniques, or obtained commercially, e.g., from Alza Corporation and Nova Pharmaceuticals, Inc. Liposomal suspensions (including liposomes targeted to selected cells with monoclonal antibodies to cellular antigens) can also be used as pharmaceutically acceptable carriers. These can be prepared according to methods known to those skilled in the art, for example, as described in U.S. Pat. No. 4,522,811.

The pharmaceutical compositions can be included in a container, pack, or dispenser, e.g., single-dose dispenser together with instructions for administration. The container, pack, or dispenser can also be included as part of a kit that can include, for example, sufficient single-dose dispensers for one day, one week, or one month of treatment.

Dosage

Dosage, toxicity and therapeutic efficacy of the compounds can be determined, e.g., by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered one from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

Methods of Treatment—Decreasing Immune Responses

Without being bound by theory, CD5L monomers, homodimers and heterodimers with p40 are believed to regulate T cells and alter immune function, and can promote suppression of pathogenic Th17 and Th1 phenotypes. Agonists of CD5L, CD5L:CD5L homodimers, and/or CD5L:p40 heterodimers (e.g., CD5L:p40 heterodimer polypeptides), can be administered to treat conditions associated with overactive inflammation or immunity, e.g., autoimmune diseases, e.g., in which pathogenic T cells are present at increased levels and/or have increased activity, such as multiple sclerosis (MS). Autoimmune conditions that may benefit from treatment using the compositions and methods described herein include, but are not limited to, for example, MS, Addison's Disease, alopecia, ankylosing spondylitis, antiphospholipid syndrome, autoimmune hemolytic anemia, autoimmune hepatitis, autoimmune oophoritis, Bechet's disease, bullous pemphigoid, celiac disease, chronic fatigue immune dysfunction syndrome (CFIDS), chronic inflammatory demyelinating polyneuropathy, Churg-Strauss syndrome, cicatricial pemphigoid, cold agglutinin disease, CREST Syndrome, Crohn's disease, diabetes (e.g., type I), dysautonomia, endometriosis, eosinophilia-myalgia syndrome, essential mixed cryoglobulinemia, fibromyalgia, syndrome/fibromyositis, Graves' disease, Guillain Barre syndrome, Hashimoto's thyroiditis, idiopathic pulmonary fibrosis, idiopathic thrombocytopenia purpura (ITP), inflammatory bowel disease (IBD), lichen planus, lupus, Meniere's disease, mixed connective tissue disease (MCTD), multiple sclerosis, myasthenia gravis, pemphigus, pernicious anemia, polyarteritis nodosa, polychondritis, polymyalgia rheumatica, polymyositis and dermatomyositis, primary agammaglobulinemia, primary biliary cirrhosis, psoriasis, Raynaud's phenomenon, Reiter's syndrome, rheumatic fever, rheumatoid arthritis, sarcoidosis, scleroderma, Sjögren's syndrome, spondyloarthropathy (spondyloarthritides), stiff-man syndrome, Takayasu arteritis, temporal arteritis/giant cell arteritis, autoimmune thyroid disease, ulcerative colitis, autoimmune uveitis, autoimmune vasculitis, vitiligo, and Wegener's granulomatosis. In some embodiments, the autoimmune disease is MS, IBD, Crohn's disease, spondyloarthritides, Systemic Lupus Erythematosus, Vitiligo, rheumatoid arthritis, psoriasis, Sjögren's syndrome, or diabetes, e.g., Type I diabetes, all of which have been linked to Th17 cell dysfunction (see, e.g., Korn et al., Annu Rev Immunol. 2009; 27:485-517 Dong, Cell Research (2014) 24:901-903; Zambrano-Zaragoza et al., Int J Inflam. 2014; 2014: 651503; Waite and Skokos, International Journal of Inflammation; Volume 2012 (2012), Article ID 819467, 10 pages, dx.doi.org/10.1155/2012/819467; Han et al., Frontiers of Medicine 9(1):10-19 (2015).

Some embodiments include treatment of autoimmune diseases, such as multiple sclerosis (MS) or IBD, using CD5L monomers, CD5L homodimers and/or CD5L:p40 heterodimers. In some embodiments, once it has been determined that a person has an autoimmune disease, e.g., MS or IBD, then a treatment comprising administration of a therapeutically effective amount of CD5L monomers, CD5L homodimers and/or CD5L:p40 heterodimers can be administered.

Generally, the methods include administering a therapeutically effective amount of CD5L monomers, CD5L homodimers and/or CD5L:p40 heterodimers as described herein, to a subject who is in need of, or who has been determined to be in need of, such treatment. As used in this context, to "treat" means to ameliorate or reduce the severity of at least one symptom of a disease or condition. For instance, a treatment can result in a reduction in one or more symptoms of an autoimmune disease, e.g., for MS, e.g., depression and fatigue, bladder dysfunction, spasticity, pain, ataxia, and intention tremor. A therapeutically effective amount can be an amount sufficient to prevent the onset of an acute episode or to shorten the duration of an acute episode, or to decrease the severity of one or more symptoms, e.g., heat sensitivity, internuclear ophthalmoplegia, optic neuritis, and Lhermitte symptom. In some embodiments, a therapeutically effective amount is an amount sufficient to prevent the appearance of, delay or prevent the growth (i.e., increase in size) of, or promote the healing of a demyelinated lesion in one or more of the brain, optic nerves, and spinal cord of the subject, e.g., as demonstrated on MRI.

Alternatively or in addition, the methods can be used to treat other conditions associated with hyperimmune responses, e.g., cancers associated with inflammation such as colorectal cancers. In certain inflammation-related cancers the IL-23 pathway has been shown to promote tumorigenesis (e.g., in colorectal cancer, carcinogen-induced skin papilloma, fibrosarcomas, mammary carcinomas and certain cancer metastasis; these studies have suggested that IL-23 and Th17 cells play a role in some cancers, such as, by way of non-limiting example, colorectal cancers. See e.g., Ye J, Livergood R S, Peng G. "The role and regulation of human Th17 cells in tumor immunity." Am J Pathol 2013 January; 182(1): 10-20. doi: 10.1016/j.ajpath.2012.08.041. Epub 2012 Nov. 14). In such cancer types, CD5L and CD5L:p40 and agents that promote their function can have anti-tumor effects. (Teng et al., 2015 Nat Med 21; Wang and Karin, Clin Exp Rheumatol 2015; 33). Thus CD5L monomers, CD5L homodimers and/or CD5L:p40 heterodimers, or nucleic acids encoding CD5L monomers, CD5L homodimers and/or CD5L:p40 heterodimers, can be used to treat or reduce risk of developing these cancers.

Standard Treatments for Autoimmune Disease

In some embodiments, a treatment, e.g., comprising CD5L, CD5L:CD5L homodimers, or CD5L:p40 heterodimers, is administered in combination with a standard treatment for an autoimmune disease. For example, in the case of MS, treatment can include administration of corticosteroid therapy, interferon beta-1b, Glatiramer acetate, mitoxantrone, Fingolimod, teriflunomide, dimethyl fumarate, natalizumab, cannabis, or a combination thereof. In some embodiments, the treatment described herein is administered in combination with a treatment for one or more symptoms of MS, e.g., depression and/or fatigue, bladder dysfunction, spasticity, pain, ataxia, and intention tremor. Such treatments can include pharmacological agents, exercise, and/or appropriate orthotics. Additional information on the diagnosis and treatment of MS can be found at the National MS Society website, on the world wide web at nationalmssociety.org.

Methods of Treatment—Enhancing Immune Responses

As shown herein and noted above, CD5L, CD5L:CD5L, and/or CD5L:p40 can regulate T cells and alter immune function. Methods that decrease the levels or activity of this CD5L, the CD5L homodimer, and/or the CD5L:p40 heterodimer can also be used to increase immune responses, e.g., to treat: subjects who have cancers that would benefit from immunotherapy (e.g., cancers that are not inflammation related); subjects who have a primary or secondary immune deficiency; or subjects who have an infection with a pathogen, e.g., viral, bacterial, or fungal pathogen.

Some embodiments comprised methods of modulating $CD8^+$ T cell exhaustion, e.g., by administering a therapeutically effective amount of an agent that: (a) inhibits CD5L, a CD5L:CD5L homodimer, and/or a CD5L:p40 heterodimer from binding to an IL-23 receptor; and/or (b) inhibits formation of the CD5L:CD5L homodimer and/or the CD5L: p40 heterodimer. Some embodiments comprise reducing $CD8^+$ T cell exhaustion or dysfunction. Some embodiments comprise increasing $CD8^+$ T cell activity.

In some embodiments, the methods include administering an agent that specifically inhibits binding of the CD5L monomer, CD5L homodimer, and/or CD5L:p40 heterodimer to a cognate receptor (e.g., the IL-23 receptor or the IL-12 receptor, beta 1 subunit), or that specifically inhibits formation of the CD5L homodimer or CD5L:p40 heterodimer. In some embodiments, the agent is an antibody, or an antigen binding fragment thereof, that binds to and inhibits the activity of the CD5L monomer, CD5L homodimer, and/or CD5L:p40 heterodimer. In some embodiments, the agent is an antagonist of CD5L, CD5L:CD5L homodimer, or CD5L: p40 heterodimer. In some embodiments, the methods include inhibiting expression of CD5L and/or p40, for example using CRISPR or by administering inhibitory nucleic acids that inhibit expression of CD5L and/or p40.

As used in this context, to "treat" means to ameliorate or reduce the severity of at least one clinical parameter of the cancer. In some embodiments, the parameter is tumor size, tumor growth rate, recurrence, or metastasis, and an improvement would be a reduction in tumor size or no change in a normally fast growing tumor; a reduction or cessation of tumor growth; a reduction in, delayed, or no recurrence, or a reduction in, delayed, or no metastasis. Administration of a therapeutically effective amount of a compound described herein for the treatment of a cancer would result in one or more of a reduction in tumor size or no change in a normally fast growing tumor; a reduction or cessation of tumor growth; or a reduction in, delayed, or no metastasis. In some embodiments, e.g., a treatment designed to prevent recurrence of cancer, the treatment would be given after a localized tumor has been removed, e.g., surgically, or treated with radiation therapy or with targeted therapy with or without other therapies such as standard chemotherapy. Without wishing to be bound by theory, such a treatment may work by keeping micrometastases dormant, e.g., by preventing them from being released from dormancy.

As used herein, the term "hyperproliferative" refer to cells having the capacity for autonomous growth, i.e., an abnormal state or condition characterized by rapidly proliferating cell growth. Hyperproliferative disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. A "tumor" is an abnormal growth of hyperproliferative cells. "Cancer" refers to pathologic disease states, e.g., characterized by malignant tumor growth. The methods described herein can be used to treat cancer, e.g., solid tumors of epithelial origin, e.g., as defined by the ICD-O (International Classification of Diseases—Oncology) code (revision 3), section (8010-8790), e.g., early stage cancer, is associated with the presence of a massive levels of satellite due to increase in transcription and processing of satellite repeats in epithelial cancer cells. Thus the methods can include the interference of satellite repeats in a sample comprising cells known or suspected of being tumor cells, e.g., cells from solid tumors of epithelial origin, e.g., pancreatic, lung, breast, prostate, renal, ovarian or colon/colorectal cancer cells.

Cancers of epithelial origin can include pancreatic cancer (e.g., pancreatic adenocarcinoma), lung cancer (e.g., non-small cell lung carcinoma or small cell lung carcinoma), prostate cancer, breast cancer, renal cancer, ovarian cancer, melanoma or colon cancer. Leukemia may include AML, CIVIL or CLL and in some embodiments comprises cancerous MDSC. The methods can also be used to treat early preneoplastic cancers as a means to prevent the development of invasive cancer.

In some embodiments, CD5L, CD5L homodimer, and/or CD5L:p40 heterodimer may be used as a biomarker for cancer progression. For example, serum CD5L, CD5L homodimer, and/or CD5L:p40 concentration can be measured and compared against a control concentration. In some embodiments, serum CD5L, CD5L homodimer, and/or CD5L:p40 concentration in a subject is measured at multiple time points, and the change in concentration is used to indicate progression of the cancer.

Standard Treatments for Cancer

In some embodiments, the methods include administering a standard anti-cancer therapy to a subject. Cancer treatments include those known in the art, e.g., surgical resection with cold instruments or lasers, radiotherapy, phototherapy, biologic therapy (e.g., with tyrosine kinase inhibitors), radiofrequency ablation (RFA), radioembolisation (e.g., with $90^Y$ spheres), chemotherapy, and immunotherapy. Immunotherapies can also include administering one or more of: adoptive cell transfer (ACT) involving transfer of ex vivo expanded autologous or allogeneic tumor-reactive lymphocytes, e.g., dendritic cells or peptides with adjuvant; chimeric antigen receptors (CARs); cancer vaccines such as DNA-based vaccines, cytokines (e.g., IL-2), cyclophosphamide, anti-interleukin-2R immunotoxins, Prostaglandin E2 Inhibitors (e.g., using SC-50) and/or checkpoint inhibitors including antibodies such as anti-CD137 (BMS-663513), anti-PD1 (e.g., Nivolumab, pembrolizumab/MK-3475, Pidilizumab (CT-011)), anti-PDL1 (e.g., BMS-936559, MPDL3280A), or anti-CTLA-4 (e.g., ipilimumab; see, e.g., Kruger et al., "Immune based therapies in cancer," Histol Histopathol. 2007 June; 22(6):687-96; Eggermont et al., "Anti-CTLA-4 antibody adjuvant therapy in melanoma," Semin Oncol. 2010 October; 37(5):455-9; Klinke D J 2nd, "A multiscale systems perspective on cancer, immunotherapy, and Interleukin-12," Mol Cancer. 2010 Sep. 15; 9:242; Alexandrescu et al., "Immunotherapy for melanoma: current status and perspectives," J Immunother. 2010 July-August; 33(6):570-90; Moschella et al., "Combination strategies for enhancing the efficacy of immunotherapy in cancer patients," Ann N Y Acad Sci. 2010 April; 1194:169-78; Ganesan and Bakhshi, "Systemic therapy for melanoma," Natl Med J India. 2010 January-February; 23(1):21-7; Golovina and Vonderheide, "Regulatory T cells: overcoming suppression of T-cell immunity," Cancer J. 2010 July-August; 16(4):342-7. In some embodiments, the methods include administering a composition comprising tumor-pulsed dendritic cells, e.g., as described in WO2009/114547 and references cited therein. See also Shiao et al., Genes & Dev. 2011, 25: 2559-2572.

As mentioned above, adoptive cell transfer (ACT) can be used as an anti-cancer therapy. ATC can refer to the transfer of cells, most commonly immune-derived cells, back into the same patient or into a new recipient host with the goal of transferring the immunologic functionality and characteristics into the new host. If possible, use of autologous cells helps the recipient by minimizing graft versus host disease (GVHD) issues. The adoptive transfer of autologous tumor infiltrating lymphocytes (TIL) (Besser et al., (2010) Clin. Cancer Res 16 (9) 2646-55; Dudley et al., (2002) Science 298 (5594): 850-4; and Dudley et al., (2005) Journal of Clinical Oncology 23 (10): 2346-57) or genetically re-directed peripheral blood mononuclear cells (Johnson et al., (2009) Blood 114 (3): 535-46; and Morgan et al., (2006) Science 314(5796) 126-9) has been used to successfully treat patients with advanced solid tumors, including melanoma and colorectal carcinoma, as well as patients with CD19-expressing hematologic malignancies (Kalos et al., (2011) Science Translational Medicine 3 (95): 95ra73).

Aspects of the invention involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; Restifo et al., 2015, Adoptive immunotherapy for cancer: harnessing the T cell response. Nat. Rev.

Immunol. 12(4): 269-281; and Jenson and Riddell, 2014, Design and implementation of adoptive therapy with chimeric antigen receptor-modified T cells. Immunol Rev. 257(1): 127-144). Various strategies may, for example, be employed to genetically modify T cells by altering the specificity of the T cell receptor (TCR), for example, by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322).

In general, CARs are comprised of an extracellular domain, a transmembrane domain, and an intracellular domain, wherein the extracellular domain comprises an antigen-binding domain that is specific for a predetermined target. While the antigen-binding domain of a CAR is often an antibody or antibody fragment (e.g., a single chain variable fragment, scFv), the binding domain is not particularly limited so long as it results in specific recognition of a target. For example, in some embodiments, the antigen-binding domain may comprise a receptor, such that the CAR is capable of binding to the ligand of the receptor. Alternatively, the antigen-binding domain may comprise a ligand, such that the CAR is capable of binding the endogenous receptor of that ligand.

The antigen-binding domain of a CAR is generally separated from the transmembrane domain by a hinge or spacer. The spacer is also not particularly limited, and it is designed to provide the CAR with flexibility. For example, a spacer domain may comprise a portion of a human Fc domain, including a portion of the CH3 domain, or the hinge region of any immunoglobulin, such as IgA, IgD, IgE, IgG, or IgM, or variants thereof. Furthermore, the hinge region may be modified so as to prevent off-target binding by FcRs or other potential interfering objects. For example, the hinge may comprise an IgG4 Fc domain with or without a S228P, L235E, and/or N297Q mutation (according to Kabat numbering) in order to decrease binding to FcRs. Additional spacers/hinges include, but are not limited to, CD4, CD8, and CD28 hinge regions.

The transmembrane domain of a CAR may be derived either from a natural or from a synthetic source. Where the source is natural, the domain may be derived from any membrane-bound or transmembrane protein. Transmembrane regions of particular use in this disclosure may be derived from CD8, CD28, CD3, CD45, CD4, CD5, CDS, CD9, CD 16, CD22, CD33, CD37, CD64, CD80, CD86, CD 134, CD137, CD 154, TCR. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

Alternative CAR constructs may be characterized as belonging to successive generations. First-generation CARs typically consist of a single-chain variable fragment of an antibody specific for an antigen, for example comprising a $V_L$ linked to a $V_H$ of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARs include a combination of costimulatory endodomains, such a CD3ζ-chain, CD97, GDI la-CD18, CD2, ICOS, CD27, CD2, CD7, LIGHT, LFA-1, NKG2C, B7-H3, CD30, CD40, PD-1, CD154, CDS, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARs in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternatively, T-cells expressing CARs may be further modified to reduce or eliminate expression of endogenous TCRs in order to reduce off-target effects. Reduction or elimination of endogenous TCRs can reduce off-target effects and increase the effectiveness of the T cells (U.S. Pat. No. 9,181,527). T cells stably lacking expression of a functional TCR may be produced using a variety of approaches. T cells internalize, sort, and degrade the entire T cell receptor as a complex, with a half-life of about 10 hours in resting T cells and 3 hours in stimulated T cells (von Essen, M. et al. 2004. J. Immunol. 173:384-393). Proper functioning of the TCR complex requires the proper stoichiometric ratio of the proteins that compose the TCR complex. TCR function also requires two functioning TCR zeta proteins with ITAM motifs. The activation of the TCR upon engagement of its MHC-peptide ligand requires the engagement of several TCRs on the same T cell, which all must signal properly. Thus, if a TCR complex is destabilized with proteins that do not associate properly or cannot signal optimally, the T cell will not become activated sufficiently to begin a cellular response.

Accordingly, in some embodiments, TCR expression may be eliminated using RNA interference (e.g., shRNA, siRNA, miRNA, etc.), CRISPR, or other methods that target the nucleic acids encoding specific TCRs (e.g., TCR-α and TCR-β) and/or CD3 chains in primary T cells. By blocking expression of one or more of these proteins, the T cell will no longer produce one or more of the key components of the TCR complex, thereby destabilizing the TCR complex and preventing cell surface expression of a functional TCR.

In some instances, CAR may also comprise a switch mechanism for controlling expression and/or activation of the CAR. For example, a CAR may comprise an extracellular, transmembrane, and intracellular domain, in which the extracellular domain comprises a target-specific binding element that comprises a label, binding domain, or tag that is specific for a molecule other than the target antigen that is expressed on or by a target cell. In such embodiments, the specificity of the CAR is provided by a second construct that comprises a target antigen binding domain (e.g., an scFv or a bispecific antibody that is specific for both the target antigen and the label or tag on the CAR) and a domain that is recognized by or binds to the label, binding domain, or tag on the CAR. See, e.g., WO 2013/044225, WO 2016/000304, WO 2015/057834, WO 2015/057852, WO 2016/070061, U.S. Pat. No. 9,233,125, US 2016/0129109. In this way, a T-cell that expresses the CAR can be administered to a subject, but the CAR cannot bind its target antigen until the second composition comprising an antigen-specific binding domain is administered.

Alternative switch mechanisms include CARs that require multimerization in order to activate their signaling function (see, e.g., US 2015/0368342, US 2016/0175359, US 2015/0368360) and/or an exogenous signal, such as a small molecule drug (US 2016/0166613, Yung et al., Science, 2015), in order to elicit a T-cell response. Some CARs may also comprise a "suicide switch" to induce cell death of the CAR T-cells following treatment (Buddee et al., PLoS One, 2013) or to downregulate expression of the CAR following binding to the target antigen (WO 2016/011210).

Various techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to treat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction).

In some embodiments, the treatment can be administrated into patients undergoing an immunosuppressive treatment. The cells, or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, intrathecally, by intravenous or intralymphatic injection, or intraperitoneally. In some embodiments, the disclosed CARs may be delivered or administered into a cavity formed by the resection of tumor tissue (i.e. intracavity delivery) or directly into a tumor prior to resection (i.e. intratumoral delivery). In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. Dosing in CAR T cell therapies may for example involve administration of from $10^6$ to $10^9$ cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). For example, the CAR T cells can comprise a T cell with CD5L and/or p40 knockouts. Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of GVHD. The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFRBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1, T-BET, RORC, or TIM-3. In preferred embodiments, the gene locus involved in the expression of PD-1 or CTLA-4 genes is targeted. In other preferred embodiments, combinations of genes are targeted, such as but not limited to PD-1 and TIGIT. In preferred embodiments, the novel genes or gene combinations described herein are targeted or modulated.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

Immune cells may be obtained using any method known in the art. In one embodiment T cells that have infiltrated a tumor are isolated. T cells may be removed during surgery. T cells may be isolated after removal of tumor tissue by biopsy. T cells may be isolated by any means known in the art. In one embodiment the method may comprise obtaining a bulk population of T cells from a tumor sample by any suitable method known in the art. For example, a bulk population of T cells can be obtained from a tumor sample by dissociating the tumor sample into a cell suspension from which specific cell populations can be selected. Suitable methods of obtaining a bulk population of T cells may include, but are not limited to, any one or more of mechanically dissociating (e.g., mincing) the tumor, enzymatically dissociating (e.g., digesting) the tumor, and aspiration (e.g., as with a needle).

The bulk population of T cells obtained from a tumor sample may comprise any suitable type of T cell. Preferably, the bulk population of T cells obtained from a tumor sample comprises tumor infiltrating lymphocytes (TILs).

The tumor sample may be obtained from any mammal. Unless stated otherwise, as used herein, the term "mammal" refers to any mammal including, but not limited to, mammals of the order Logomorpha, such as rabbits; the order Carnivora, including Felines (cats) and Canines (dogs); the order Artiodactyla, including Bovines (cows) and Swines (pigs); or of the order Perissodactyla, including Equines (horses). The mammals may be non-human primates, e.g., of the order Primates, Ceboids, or Simoids (monkeys) or of the order Anthropoids (humans and apes). In some embodiments, the mammal may be a mammal of the order Rodentia, such as mice and hamsters. Preferably, the mammal is a non-human primate or a human. An especially preferred mammal is the human.

T cells can be obtained from a number of sources, including peripheral blood mononuclear cells, bone marrow, lymph node tissue, spleen tissue, and tumors. In certain embodiments of the present invention, T cells can be obtained from a unit of blood collected from a subject using any number of techniques known to the skilled artisan, such as Ficoll separation. In one preferred embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Initial activation steps in the absence of calcium lead to magnified activation. As those of ordinary skill in the art would readily, appreciate a washing step may be accomplished by methods known to those in the art, such as by using a semi-automated "flow-through" centrifuge (for example, the Cobe 2991 cell processor) according to the manufacturer's instructions. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient. A specific subpopulation of T cells, such as CD28+. CD4+, CDC, CD45RA+, and CD451RO+ T cells, can be further isolated by positive or negative selection techniques. For example, in one preferred embodiment, T cells are isolated by incubation with anti-CD3/anti-CD28 (i.e., 3×28)-conjugated beads, such as DSC BEADS® M-450 CD3/CD28 T, or XCYTE DYNA-BEADS™ for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells.

Enrichment of a T cell population by negative selection can be accomplished with a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD 11b, CD16, HLA-DR, and CD8.

Further, monocyte populations (i.e., CD14+ cells) may be depleted from blood preparations by a variety of methodologies, including anti-CD14 coated beads or columns, or utilization of the phagocytotic activity of these cells to facilitate removal. Accordingly, in one embodiment, the invention uses paramagnetic particles of a size sufficient to be engulfed by phagocytotic monocytes. In certain embodiments, the paramagnetic particles are commercially available beads, for example, those produced by Life Technologies under the trade name Dynabeads™. In one embodiment, other non-specific cells are removed by coating the paramagnetic particles with "irrelevant" proteins (e.g., serum proteins or antibodies). Irrelevant proteins and antibodies include those proteins and antibodies or fragments thereof that do not specifically target the T cells to be isolated. In certain embodiments the irrelevant beads include beads coated with sheep anti-mouse antibodies, goat anti-mouse antibodies, and human serum albumin.

In brief, such depletion of monocytes is performed by preincubating T cells isolated from whole blood, apheresed peripheral blood, or tumors with one or more varieties of irrelevant or non-antibody coupled paramagnetic particles at any amount that allows for removal of monocytes (approximately a 20:1 bead:cell ratio) for about 30 minutes to 2 hours at 22 to 37 degrees C., followed by magnetic removal of cells which have attached to or engulfed the paramagnetic particles. Such separation can be performed using standard methods available in the art. For example, any magnetic separation methodology may be used including a variety of which are commercially available, (e.g., DYNAL® Magnetic Particle Concentrator (DYNAL MPC®)). Assurance of requisite depletion can be monitored by a variety of methodologies known to those of ordinary skill in the art, including flow cytometric analysis of CD14 positive cells, before and after depletion.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, $CD4^+$ T cells express higher levels of CD28 and are more efficiently captured than CD8+ cells in dilute concentrations. In one embodiment, the concentration of cells used is $5\times10^6$/ml. In other embodiments, the concentration used can be from about $1\times10^5$/ml to $1\times10^6$/ml, and any integer value in between.

T cells can also be frozen. Wishing not to be bound by theory, the freeze and subsequent thaw step provides a more uniform product by removing granulocytes and to some extent monocytes in the cell population. After a washing step to remove plasma and platelets, the cells may be suspended in a freezing solution. While many freezing solutions and parameters are known in the art and will be useful in this context, one method involves using PBS containing 20% DMSO and 8% human serum albumin, or other suitable cell freezing media, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

T cells for use in the present invention may also be antigen-specific T cells. For example, tumor-specific T cells can be used. In certain embodiments, antigen-specific T cells can be isolated from a patient of interest, such as a patient afflicted with a cancer or an infectious disease. In one embodiment neoepitopes are determined for a subject and T cells specific to these antigens are isolated. Antigen-specific cells for use in expansion may also be generated in vitro using any number of methods known in the art, for example, as described in U.S. Patent Publication No. US 20040224402 entitled, Generation And Isolation of Antigen-Specific T Cells, or in U.S. Pat. No. 6,040,177. Antigen-specific cells for use in the present invention may also be generated using any number of methods known in the art, for example, as described in Current Protocols in Immunology, or Current Protocols in Cell Biology, both published by John Wiley & Sons, Inc., Boston, Mass.

In a related embodiment, it may be desirable to sort or otherwise positively select (e.g. via magnetic selection) the antigen specific cells prior to or following one or two rounds of expansion. Sorting or positively selecting antigen-specific cells can be carried out using peptide-MHC tetramers (Altman, et al., Science. 1996 Oct. 4; 274(5284):94-6). In another embodiment the adaptable tetramer technology approach is used (Andersen et al., 2012 Nat Protoc. 7:891-902). Tetramers are limited by the need to utilize predicted binding peptides based on prior hypotheses, and the restriction to specific HLAs. Peptide-MHC tetramers can be generated using techniques known in the art and can be made with any MHC molecule of interest and any antigen of interest as described herein. Specific epitopes to be used in this context can be identified using numerous assays known in the art. For example, the ability of a polypeptide to bind to MHC class I may be evaluated indirectly by monitoring the ability to promote incorporation of $^{125}$I labeled β2-microglobulin (β2m) into MHC class I/β2m/peptide heterotrimeric complexes (see Parker et al., J. Immunol. 152:163, 1994).

In one embodiment cells are directly labeled with an epitope-specific reagent for isolation by flow cytometry followed by characterization of phenotype and TCRs. In one T cells are isolated by contacting the T cell specific antibodies. Sorting of antigen-specific T cells, or generally any cells of the present invention, can be carried out using any of a variety of commercially available cell sorters, including, but not limited to, MoFlo sorter (DakoCytomation, Fort Collins, Colo.), FACSAria™, FACSArray™, FACSVantage™, BD™ LSI II, and FACSCalibur™ (BD Biosciences, San Jose, Calif.).

In a preferred embodiment, the method comprises selecting cells that also express CD3. The method may comprise specifically selecting the cells in any suitable manner. Preferably, the selecting is carried out using flow cytometry. The flow cytometry may be carried out using any suitable method known in the art. The flow cytometry may employ any suitable antibodies and stains. Preferably, the antibody is chosen such that it specifically recognizes and binds to the particular biomarker being selected. For example, the specific selection of CD3, CD8, TIM-3, LAG-3, 4-1BB, or PD-1 may be carried out using anti-CD3, anti-CD8, anti-TIM-3, anti-LAG-3, anti-4-1BB, or anti-PD-1 antibodies, respectively. The antibody or antibodies may be conjugated to a bead (e.g., a magnetic bead) or to a fluorochrome. Preferably, the flow cytometry is fluorescence-activated cell sorting (FACS). TCRs expressed on T cells can be selected based on reactivity to autologous tumors. Additionally, T cells that are reactive to tumors can be selected for based on markers using the methods described in patent publication Nos. WO2014133567 and WO2014133568, herein incorporated by reference in their entirety. Additionally, activated T cells can be selected for based on surface expression of CD107a.

In one embodiment of the invention, the method further comprises expanding the numbers of T cells in the enriched cell population. Such methods are described in U.S. Pat. No. 8,637,307 and is herein incorporated by reference in its entirety. The numbers of T cells may be increased at least about 3-fold (or 4-, 5-, 6-, 7-, 8-, or 9-fold), more preferably at least about 10-fold (or 20-, 30-, 40-, 50-, 60-, 70-, 80-, or 90-fold), more preferably at least about 100-fold, more preferably at least about 1,000 fold, or most preferably at least about 100,000-fold. The numbers of T cells may be expanded using any suitable method known in the art. Exemplary methods of expanding the numbers of cells are described in patent publication No. WO 2003057171, U.S. Pat. No. 8,034,334, and U.S. Patent Application Publication No. 2012/0244133, each of which is incorporated herein by reference.

In one embodiment, ex vivo T cell expansion can be performed by isolation of T cells and subsequent stimulation or activation followed by further expansion. In one embodiment of the invention, the T cells may be stimulated or activated by a single agent. In another embodiment, T cells are stimulated or activated with two agents, one that induces a primary signal and a second that is a co-stimulatory signal. Ligands useful for stimulating a single signal or stimulating a primary signal and an accessory molecule that stimulates a second signal may be used in soluble form. Ligands may be attached to the surface of a cell, to an Engineered Multivalent Signaling Platform (EMSP), or immobilized on a surface. In a preferred embodiment both primary and secondary agents are co-immobilized on a surface, for example a bead or a cell. In one embodiment, the molecule providing the primary activation signal may be a CD3 ligand, and the co-stimulatory molecule may be a CD28 ligand or 4-1BB ligand.

Antibodies to CD5L, CD5L: CD5L, or CD5L:p40 Heterodimer

As already mentioned, some embodiments comprise methods that include administering an antibody or an antigen fragment thereof that binds to and inhibits the activity of CD5L monomer, CD5L homodimer, or the CD5L:p40 heterodimer, e.g., that specifically inhibits binding of the CD5L monomer, CD5L homodimer, or CD5L:p40 heterodimer to the IL-23 receptor, or that specifically inhibits formation of the CD5L homodimer or CD5L:p40 heterodimer.

The term "antibody" as used herein refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments the antibody has effector function and can fix complement. In some embodiments, the antibody has reduced or no ability to bind an Fc receptor. For example, the antibody can be an isotype or subtype, fragment or other mutant, which does not support binding to an Fc receptor, e.g., it has a mutagenized or deleted Fc receptor binding region. Methods for making antibodies and fragments thereof are known in the art, see, e.g., Harlow et. al., editors, Antibodies: A Laboratory Manual (1988); Goding, Monoclonal Antibodies: Principles and Practice, (N.Y. Academic Press 1983); Howard and Kaser, Making and Using Antibodies: A Practical Handbook (CRC Press; 1st edition, Dec. 13, 2006); Kontermann and Dübel, Antibody Engineering Volume 1 (Springer Protocols) (Springer; 2nd ed., May 21, 2010); Lo, Antibody Engineering: Methods and Protocols (Methods in Molecular Biology) (Humana Press; Nov. 10, 2010); and Dübel, Handbook of Therapeutic Antibodies: Technologies, Emerging Developments and Approved Therapeutics, (Wiley-VCH; 1 edition Sep. 7, 2010).

Inhibitory Nucleic Acids

Some embodiments comprise decreasing protein expression (e.g., CD5L or p40 expression) with inhibitory nucleic acids. Inhibitory nucleic acids useful in the present methods and compositions include antisense oligonucleotides, ribozymes, external guide sequence (EGS) oligonucleotides, siRNA compounds, single- or double-stranded RNA interference (RNAi) compounds such as siRNA compounds, modified bases/locked nucleic acids (LNAs), antagomirs, peptide nucleic acids (PNAs), ribozymes, and other oligomeric compounds or oligonucleotide mimetics which hybridize to at least a portion of the target nucleic acid and modulate its function. In some embodiments, the inhibitory nucleic acids include antisense RNA, antisense DNA, chimeric antisense oligonucleotides, antisense oligonucleotides comprising modified linkages, interference RNA (RNAi), short interfering RNA (siRNA); a micro, interfering RNA (miRNA); a small, temporal RNA (stRNA); or a short, hairpin RNA (shRNA); small RNA-induced gene activation (RNAa); small activating RNAs (saRNAs), or combinations thereof. See, e.g., WO 2010040112; Burnett and Rossi (2012) Chem Biol. 19 (1):60-71; and WO2015130968, which is incorporated herein by reference in its entirety.

In some embodiments, the inhibitory nucleic acids are 10 to 50, 13 to 50, or 13 to 30 nucleotides in length. One having ordinary skill in the art will appreciate that this embodies oligonucleotides having antisense portions of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleotides in length, or any range there within. In some embodiments, the oligonucleotides are 15 nucleotides in length. In some embodiments, the antisense or oligonucleotide compounds of the invention are 12 or 13 to 30 nucleotides in length. One having ordinary skill in the art will appreciate that this embodies inhibitory nucleic acids having antisense portions of 12, 13, 14, 15, 16, 17, 18, 19, 20, 21, 22, 23, 24, 25, 26, 27, 28, 29 or 30 nucleotides in length, or any range there within.

In some embodiments, the inhibitory nucleic acids are chimeric oligonucleotides that contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the target) and a region that is a substrate for enzymes capable of cleaving RNA:DNA or RNA:RNA hybrids. Chimeric inhibitory nucleic acids of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures comprise, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; 5,700,922; 8,604,192; 8,697,663; 8,703,728; 8,796,437; 8,865,677; and 8,883,752 each of which is herein incorporated by reference.

In some embodiments, the inhibitory nucleic acid comprises at least one nucleotide modified at the 2' position of the sugar, most preferably a 2'-O-alkyl, 2'-O-alkyl-O-alkyl or 2'-fluoro-modified nucleotide. In other preferred embodiments, RNA modifications include 2'-fluoro, 2'-amino and 2'-O-methyl modifications on the ribose of pyrimidines, abasic residues or an inverted base at the 3' end of the RNA. Such modifications are routinely incorporated into oligonucleotides and these oligonucleotides have been shown to have a higher Tm (i.e., higher target binding affinity) than; 2'-deoxyoligonucleotides against a given target.

A number of nucleotide and nucleoside modifications have been shown to make the oligonucleotide into which they are incorporated more resistant to nuclease digestion than the native oligodeoxynucleotide; these modified oligos survive intact for a longer time than unmodified oligonucleotides. Specific examples of modified oligonucleotides include those comprising modified backbones, for example, phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioate backbones and those with heteroatom backbones, particularly CH2-NH—O—CH2, CH, ~N(CH3)~O~CH2 (known as a methylene(methylimino) or MMI backbone], CH2-O—N (CH3)—CH2, CH2-N(CH3)—N (CH3)—CH2 and O—N (CH3)—CH2-CH2 backbones, wherein the native phosphodiester backbone is represented as O—P—O—CH); amide backbones (De Mesmaeker (1995) Ace. Chem. Res. 28:366-374); morpholino backbone structures (Summerton and Weller, U.S. Pat. No. 5,034,506); peptide nucleic acid (PNA) backbone (wherein the phosphodiester backbone of the oligonucleotide is replaced with a polyamide backbone, the nucleotides being bound directly or indirectly to the aza nitrogen atoms of the polyamide backbone, Nielsen (1991) Science 254, 1497). Phosphorus-containing linkages include, but are not limited to, phosphorothioates, chiral phosphorothioates, phosphorodithioates, phosphotriesters, aminoalkylphosphotriesters, methyl and other alkyl phosphonates comprising 3'-alkylene phosphonates and chiral phosphonates, phosphinates, phosphoramidates comprising 3'-amino phosphoramidate and aminoalkylphosphoramidates, phosphonoacetate phosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'; see U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Morpholino-based oligomeric compounds are described in Dwaine A. Braasch and David R. Corey (2002) Biochemistry 41(14), 4503-4510); Genesis, volume 30, issue 3, 2001; Heasman, (2002) Dev. Biol. 243, 209-214; Nasevicius (2000) Nat. Genet. 26, 216-220; Lacerra (2000) Proc. Natl. Acad. Sci. 97, 9591-9596; and U.S. Pat. No. 5,034,506, issued Jul. 23, 1991. Cyclohexenyl nucleic acid oligonucleotide mimetics are described in Wang (2000) Am. Chem. Soc. 122, 8595-8602.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These comprise those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts; see U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,677,439; and 8,927,513 each of which is herein incorporated by reference.

One or more substituted sugar moieties can also be included, e.g., one of the following at the 2' position: OH, SH, $SCH_3$, F, OCN, $OCH_3$, $OCH_3$ $O(CH_2)n$ $CH_3$, $O(CH_2)n$ $NH_2$ or $O(CH_2)n$ $CH_3$ where n is from 1 to about 10; Ci to C10 lower alkyl, alkoxyalkoxy, substituted lower alkyl, alkaryl or aralkyl; Cl; Br; CN; CF3; OCF3; O-, S-, or N-alkyl; O-, S-, or N-alkenyl; SOCH3; SO2 CH3; ONO2; NO2; N3; NH2; heterocycloalkyl; heterocycloalkaryl; aminoalkylamino; polyalkylamino; substituted silyl; an RNA cleaving group; a reporter group; an intercalator; a group for improving the pharmacokinetic properties of an oligonucleotide; or a group for improving the pharmacodynamic properties of an oligonucleotide and other substituents having similar properties. A preferred modification includes 2'-methoxyethoxy [2'-O—CH$_2$CH$_2$OCH$_3$, also known as 2'-O-(2-methoxyethyl)] (Martin (1995) Helv. Chim. Acta 78, 486). Other preferred modifications include 2'-methoxy (2'-O—CH$_3$—), 2'-propoxy (2'-OCH$_2$ CH$_2$CH$_3$) and 2'-fluoro (2'-F). Similar modifications may also be made at other positions on the oligonucleotide, particularly the 3' position of the sugar on the 3' terminal nucleotide and the 5' position of 5' terminal nucleotide. Oligonucleotides may also have sugar mimetics such as cyclobutyls in place of the pentofuranosyl group.

Inhibitory nucleic acids can also include, additionally or alternatively, nucleobase (often referred to in the art simply as "base") modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-Me pyrimidines, particularly 5-methylcytosine (also referred to as 5-methyl-2' deoxycytosine and often referred to in the art as 5-Me-C), 5-hydroxymethylcytosine (HMC), glycosyl HMC and gentiobiosyl HMC, as well as synthetic nucleobases, e.g., 2-aminoadenine, 2-(methylamino)adenine, 2-(imidazolylalkyl)adenine, 2-(aminoalkylamino)adenine or other heterosubstituted alkyladenines, 2-thiouracil, 2-thiothymine, 5-bromouracil, 5-hydroxymethyluracil, 8-azaguanine, 7-deazaguanine, N6 (6-aminohexyl)adenine, 2,6-diaminopurine; 5-ribosyluracil (Carlile (2014) Nature 515 (7525): 143-6). Kornberg, A., DNA Replication, W. H. Freeman & Co., San Francisco, 1980, pp 75-77; Gebeyehu (1987) Nucl. Acids Res. 15:4513). A "universal" base known in the art, e.g., inosine, can also be included. 5-Me-C substitutions have been shown to increase nucleic acid duplex stability by 0.6-1.2<0>C. (Sanghvi, Y. S., in Crooke, S. T. and Lebleu, B., eds., Antisense Research and Applications, CRC Press, Boca Raton, 1993, pp. 276-278) and are presently preferred base substitutions.

It is not necessary for all positions in a given oligonucleotide to be uniformly modified, and in fact more than one of the aforementioned modifications may be incorporated in a single oligonucleotide or even at within a single nucleoside within an oligonucleotide. In some embodiments, both the nucleobase and backbone may be modified to enhance stability and activity (El-Sagheer (2014) Chem Sci 5:253-259).

In some embodiments, both a sugar and an internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, for example, an aminoethylglycine backbone. The nucleobases are retained and are bound directly or indirectly to aza nitrogen atoms of the amide portion of the backbone. Representative United States patents that teach the preparation of PNA compounds comprise, but are not limited to, U.S. Pat. Nos. 5,539,082; 5,714,331; and 5,719,262, each of which is herein incorporated by reference. Further teaching of PNA compounds can be found in Nielsen (1991) Science 254, 1497-1500; and Shi (2015).

Inhibitory nucleic acids can also include one or more nucleobase (often referred to in the art simply as "base") modifications or substitutions. As used herein, "unmodified" or "natural" nucleobases comprise the purine bases adenine (A) and guanine (G), and the pyrimidine bases thymine (T), cytosine (C) and uracil (U). Modified nucleobases comprise other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudo-uracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

Further, nucleobases comprise those disclosed in U.S. Pat. No. 3,687,808, those disclosed in 'The Concise Encyclopedia of Polymer Science And Engineering', pages 858-859, Kroschwitz, J. I., ed. John Wiley & Sons, 1990, those disclosed by Englisch et al., Angewandte Chemie, International Edition', 1991, 30, page 613, and those disclosed by Sanghvi, Y. S., Chapter 15, Antisense Research and Applications', pages 289-302, Crooke, S. T. and Lebleu, B. ea., CRC Press, 1993. Certain of these nucleobases are particularly useful for increasing the binding affinity of the oligomeric compounds of the invention. These include 5-substituted pyrimidines, 6-azapyrimidines and N-2, N-6 and 0-6 substituted purines, comprising 2-aminopropyladenine, 5-propynyluracil and 5-propynylcytosine. 5-methylcytosine substitutions have been shown to increase nucleic acid duplex stability by 0.6-1.2<0>C (Sanghvi, Y. S., Crooke, S. T. and Lebleu, B., eds, 'Antisense Research and Applications', CRC Press, Boca Raton, 1993, pp. 276-278) and are presently preferred base substitutions, even more particularly when combined with 2'-O-methoxyethyl sugar modifications. Modified nucleobases are described in U.S. Pat. No. 3,687,808, as well as U.S. Pat. Nos. 4,845,205; 5,130, 302; 5,134,066; 5,175,273; 5,367,066; 5,432,272; 5,457, 187; 5,459,255; 5,484,908; 5,502,177; 5,525,711; 5,552, 540; 5,587,469; 5,596,091; 5,614,617; 5,750,692, and 5,681,941, each of which is herein incorporated by reference.

In some embodiments, the inhibitory nucleic acids are chemically linked to one or more moieties or conjugates that enhance the activity, cellular distribution, or cellular uptake of the oligonucleotide. Such moieties comprise but are not limited to, lipid moieties such as a cholesterol moiety (Letsinger (1989) Proc. Natl. Acad. Sci. USA 86, 6553-6556), cholic acid (Manoharan (1994) Bioorg. Med. Chem. Let. 4, 1053-1060), a thioether, e.g., hexyl-S-tritylthiol (Manoharan (1992) Ann. N. Y. Acad. Sci. 660, 306-309; Manoharan (1993) Bioorg. Med. Chem. Let. 3, 2765-2770), a thiocholesterol (Oberhauser (1992) Nucl. Acids Res. 20, 533-538), an aliphatic chain, e.g., dodecanediol or undecyl residues (Kabanov (1990) FEBS Lett. 259, 327-330; Svinarchuk (1993) Biochimie 75, 49-54), a phospholipid, e.g., di-hexadecyl-rac-glycerol or triethylammonium 1,2-di-O-hexadecyl-rac-glycero-3-H-phosphonate (Manoharan (1995) Tetrahedron Lett. 36, 3651-3654; Shea (1990) Nucl. Acids Res. 18, 3777-3783), a polyamine or a polyethylene glycol chain (Mancharan (1995) Nucleosides & Nucleotides 14, 969-973), or adamantane acetic acid (Manoharan (1995) Tetrahedron Lett. 36, 3651-3654), a palmityl moiety (Mishra (1995) Biochim. Biophys. Acta 1264, 229-237), or an octadecylamine or hexylamino-carbonyl-t oxycholesterol moiety (Crooke (1996) J. Pharmacol. Exp. Ther. 277, 923-937).

See also U.S. Pat. Nos. 4,828,979; 4,948,882; 5,218,105; 5,525,465; 5,541,313; 5,545,730; 5,552,538; 5,578,717; 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928; 5,688,941, 8,865,677; 8,877,917 each of which is herein incorporated by reference.

These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application No. PCT/US92/09196, filed Oct. 23, 1992, and U.S. Pat. No. 6,287,860, which are incorporated herein by reference. Conjugate moieties include, but are not limited to, lipid moieties such as a cholesterol moiety, cholic acid, a thioether, e.g., hexyl-5-tritylthiol, a thiocholesterol, an aliphatic chain, e.g., dodecanediol or undecyl residues, a phospholipid, e.g., di-hexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxy cholesterol moiety. See, e.g., U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203; 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941.

The inhibitory nucleic acids useful in the present methods are sufficiently complementary to the target lncRNA, i.e., hybridize sufficiently well and with sufficient specificity, to give the desired effect. "Complementary" in this context refers to the capacity for pairing, through hydrogen bonding, between two sequences comprising naturally or non-naturally occurring bases or analogs thereof. For example, if a base at one position of an inhibitory nucleic acid is capable of hydrogen bonding with a base at the corresponding position of a lncRNA, then the bases are considered to be complementary to each other at that position. 100% complementarity is not required.

In some embodiments, the location on a target lncRNA to which an inhibitory nucleic acids hybridizes is defined as a target region to which a protein binding partner binds. These regions can be identified by reviewing the data submitted herewith in Appendix I and identifying regions that are enriched in the dataset; these regions are likely to include the protein binding sequences. Routine methods can be used to design an inhibitory nucleic acid that binds to this sequence with sufficient specificity. In some embodiments, the methods include using bioinformatics methods known in the art to identify regions of secondary structure, e.g., one, two, or more stem-loop structures, or pseudoknots, and selecting those regions to target with an inhibitory nucleic acid.

While the specific sequences of certain exemplary target segments are set forth herein, one of skill in the art will recognize that these serve to illustrate and describe particular embodiments within the scope of the present invention. Additional target segments are readily identifiable by one having ordinary skill in the art in view of this disclosure. Target segments 5-500 nucleotides in length comprising a stretch of at least five (5) consecutive nucleotides within the protein binding region, or immediately adjacent thereto, are considered to be suitable for targeting as well. Target segments can include sequences that comprise at least the 5 consecutive nucleotides from the 5'-terminus of one of the protein binding regions (the remaining nucleotides being a consecutive stretch of the same RNA beginning immediately upstream of the 5'-terminus of the binding segment and continuing until the inhibitory nucleic acid contains about 5 to about 100 nucleotides). Similarly preferred target segments are represented by RNA sequences that comprise at least the 5 consecutive nucleotides from the 3'-terminus of one of the illustrative preferred target segments (the remaining nucleotides being a consecutive stretch of the same lncRNA beginning immediately downstream of the 3'-terminus of the target segment and continuing until the inhibitory nucleic acid contains about 5 to about 100 nucleotides). One having skill in the art armed with the sequences provided herein will be able, without undue experimentation, to identify further preferred protein binding regions to target.

Once one or more target regions, segments or sites have been identified, inhibitory nucleic acid compounds are chosen that are sufficiently complementary to the target, i.e., that hybridize sufficiently well and with sufficient specificity (i.e., do not substantially bind to other non-target RNAs), to give the desired effect.

Making and Using Inhibitory Nucleic Acids

The inhibitory nucleic acids used to practice the methods described herein, whether RNA, cDNA, genomic DNA, vectors, viruses or hybrids thereof, can be isolated from a variety of sources, genetically engineered, amplified, and/or expressed, generated recombinantly or synthetically by well-known chemical synthesis techniques, as described in, e.g., Adams (1983) J. Am. Chem. Soc. 105:661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; Maier (2000) Org Lett 2(13):1819-1822; Egeland (2005) Nucleic Acids Res 33(14):e125; Krotz (2005) Pharm Dev Technol 10(2):283-90 U.S. Pat. No. 4,458,066. Recombinant nucleic acid sequences can be individually isolated or cloned and tested for a desired activity. Any recombinant expression system can be used, including e.g. in vitro bacterial, fungal, mammalian, yeast, insect or plant cell expression systems.

Nucleic acid sequences of the invention can be inserted into delivery vectors and expressed from transcription units within the vectors. The recombinant vectors can be DNA plasmids or viral vectors. Generation of the vector construct can be accomplished using any suitable genetic engineering techniques well known in the art, including, without limitation, the standard techniques of PCR, oligonucleotide synthesis, restriction endonuclease digestion or "seamless cloning", ligation, transformation, plasmid purification, and DNA sequencing, for example as described in Sambrook et al. "Molecular Cloning: A Laboratory Manual." (1989)), Coffin et al. (Retroviruses. (1997)) and "RNA Viruses: A Practical Approach" (Alan J. Cann, Ed., Oxford University Press, (2000)). "Seamless cloning" allows joining of multiple fragments of nucleic acids in a single, isothermal reaction (Gibson (2009) Nat Methods 6:343-345; Werner (2012) Bioeng Bugs 3:38-43; Sanjana (2012) Nat Protoc 7:171-192). As will be apparent to one of ordinary skill in the art, a variety of suitable vectors are available for transferring nucleic acids of the invention into cells. The selection of an appropriate vector to deliver nucleic acids and optimization of the conditions for insertion of the selected expression vector into the cell, are within the scope of one of ordinary skill in the art without the need for undue experimentation. Viral vectors comprise a nucleotide sequence having sequences for the production of recombinant virus in a packaging cell. Viral vectors expressing nucleic acids of the invention can be constructed based on viral backbones including, but not limited to, a retrovirus, lentivirus, adenovirus, adeno-associated virus, pox virus or alphavirus (Warnock (2011) Methods in Molecular Biology 737:1-25). The recombinant vectors capable of expressing the nucleic acids of the invention can be delivered as described herein, and persist in target cells (e.g., stable transformants).

This can be achieved, for example, by administering an inhibitory nucleic acid, e.g., antisense oligonucleotides complementary to p40 and/or CD5L. Other inhibitory nucleic acids for use in practicing the methods described herein and that are complementary to p40 and/or CD5L can be those which inhibit post-transcriptional processing of p40 or CD5L, such as inhibitors of mRNA translation (antisense), agents of RNA interference (RNAi), catalytically active RNA molecules (ribozymes), and RNAs that bind proteins and other molecular ligands (aptamers). Additional methods exist to inhibit endogenous microRNA (miRNA) activity through the use of antisense-miRNA oligonucleotides (antagomirs) and RNA competitive inhibitors or decoys (miRNA sponges).

For further disclosure regarding inhibitory nucleic acids, please see US2010/0317718 (antisense oligos); US2010/0249052 (double-stranded ribonucleic acid (dsRNA)); US2009/0181914 and US2010/0234451 (LNAs); US2007/0191294 (siRNA analogues); US2008/0249039 (modified siRNA); and WO2010/129746 and WO2010/040112 (inhibitory nucleic acids).

Antisense

In some embodiments, the inhibitory nucleic acids are antisense oligonucleotides. Antisense oligonucleotides are typically designed to block expression of a DNA or RNA target by binding to the target and halting expression at the level of transcription, translation, or splicing. Antisense oligonucleotides of the present invention are complementary nucleic acid sequences designed to hybridize under stringent conditions to p40 and/or CD5L. Thus, oligonucleotides are chosen that are sufficiently complementary to the target, i.e., that hybridize sufficiently well and with sufficient specificity, to give the desired effect, while striving to avoid significant off-target effects i.e. must not directly bind to, or directly significantly affect expression levels of, transcripts other than the intended target. The optimal length of the antisense oligonucleotide may very but it should be as short as possible while ensuring that its target sequence is unique in the transcriptome i.e. antisense oligonucleotides may be as short as 12-mers (Seth (2009) J Med Chem 52:10-13) to 18-22 nucleotides in length.

In the context of this invention, hybridization means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. Complementary, as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target.

It is understood in the art that a complementary nucleic acid sequence need not be 100% complementary to that of its target nucleic acid to be specifically hybridisable. A complementary nucleic acid sequence of the invention is specifically hybridisable when binding of the sequence to the target DNA or RNA molecule interferes with the normal function of the target DNA or RNA to cause a loss of activity, and there is a sufficient degree of complementarity to avoid non-specific binding of the sequence to non-target sequences under conditions in which specific binding is desired, i.e., under physiological conditions in the case of in vivo assays or therapeutic treatment, and in the case of in vitro assays, under conditions in which the assays are performed under suitable conditions of stringency. The antisense oligonucleotides useful in the methods described herein have at least 80% sequence complementarity to a target region within the target nucleic acid, e.g., 90%, 95%, or 100% sequence complementarity to the target region within p40 or CD5L (e.g., a target region comprising the seed sequence). Percent complementarity of an antisense compound with a region of a target nucleic acid can be determined routinely using basic local alignment search tools (BLAST programs) (Altschul (1990) J. Mol. Biol. 215, 403-410; Zhang and Madden (1997) Genome Res. 7, 649-656). The specificity of an antisense oligonucleotide can also be determined routinely using BLAST program against the entire genome of a given species For example, stringent salt concentration will ordinarily be less than about 750 mM NaCl and 75 mM trisodium citrate, preferably less than about 500 mM NaCl and 50 mM trisodium citrate, and more preferably less than about 250 mM NaCl and 25 mM trisodium citrate. Low stringency hybridization can be obtained in the absence of organic solvent, e.g., formamide, while high stringency hybridization can be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In a preferred embodiment, hybridization will occur at 30° C. in 750 mM NaCl, 75 mM trisodium citrate, and 1% SDS. In a more preferred embodiment, hybridization will occur at 37° C. in 500 mM NaCl, 50 mM trisodium citrate, 1% SDS, 35% formamide, and 100 µg/ml denatured salmon sperm DNA (ssDNA). In a most preferred embodiment, hybridization will occur at 42° C. in 250 mM NaCl, 25 mM trisodium citrate, 1% SDS, 50% formamide, and 200 µg/ml ssDNA. Useful variations on these conditions will be readily apparent to those skilled in the art. For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will preferably be less than about 30 mM NaCl and 3 mM trisodium citrate, and most preferably less than about 15 mM NaCl and 1.5 mM trisodium citrate. Stringent temperature conditions for the wash steps will ordinarily include a temperature of at least about 25° C., more preferably of at least about 42° C., and even more preferably of at least about 68° C. In a preferred embodiment, wash steps will occur at 25° C. in 30 mM NaCl, 3 mM trisodium citrate, and 0.1% SDS. In a more preferred embodiment, wash steps will occur at 42° C. in 15 mM NaCl, 1.5 mM trisodium citrate, and 0.1% SDS. In a more preferred embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York, Hilario (2007) Methods Mol Biol 353:27-38.

Inhibitory nucleic acids for use in the methods described herein can include one or more modifications, e.g., be stabilized against nucleolytic degradation such as by the incorporation of a modification, e.g., a nucleotide modification. For example, inhibitory nucleic acids can include a phosphorothioate at least the first, second, or third internucleotide linkage at the 5' or 3' end of the nucleotide sequence. As another example, inhibitory nucleic acids can include a 2'-modified nucleotide, e.g., a 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA). As another example, the inhibitory nucleic acids can include at least one 2'-O-methyl-modified nucleotide, and in some embodiments, all of the nucleotides include a 2'-O-methyl modification.

Modifications

Chemical modifications, particularly the use of locked nucleic acids (LNAs) (Okiba (1997) Tetrahedron Lett 39:5401-5404; Singh (1998) Chem Commun 4:455-456), 2'-O-methoxyethyl (2'-O-MOE) (Martin (1995) Helv Chim Acta 78:486-504; You (2006) Nucleic Acids Res 34(8):e60; Owczarzy (2011) Biochem 50(43):9352-9367), constrained ethyl BNA (cET) (Murray (2012) Nucleic Acids Res 40: 6135-6143), and gapmer oligonucleotides, which contain 2-5 chemically modified nucleotides (LNA, 2'-O-MOE RNA or cET) at each terminus flanking a central 5-10 base "gap" of DNA (Monia (1993) J Biol Chem 268:14514-14522; Wahlestedt (2000) PNAS 97:5633-5638), improve antisense oligonucleotide binding affinity for the target RNA, which increases the steric block efficiency. Antisense oligos that hybridize to p40 or CD5L, can be identified through experimentation.

Techniques for the manipulation of inhibitory nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook et al., Molecular Cloning; A Laboratory Manual 3d ed. (2001); Current Protocols in Molecular Biology, Ausubel et al., eds. (John Wiley & Sons, Inc., New York 2010); Kriegler, Gene Transfer and Expression: A Laboratory Manual (1990); Laboratory Techniques In Biochemistry And Molecular Biology: Hybridization With Nucleic Acid Probes, Part I. Theory and Nucleic Acid Preparation, Tijssen, ed. Elsevier, N.Y. (1993).

Modified Bases/Locked Nucleic Acids (LNAs)

In some embodiments, the inhibitory nucleic acids are "locked," i.e., comprise nucleic acid analogues in which the ribose ring is "locked" by a methylene bridge connecting the 2'-O atom and the 4'-C atom (see, e.g., Kaupinnen (2005) Drug Disc. Today 2(3):287-290; Koshkin (1998) J. Am. Chem. Soc. 120(50):13252-13253). For additional modifications see US 20100004320, US 20090298916, and US 20090143326.

siRNA/shRNA

In some embodiments, the nucleic acid sequence that is complementary to p40 or CD5L can be an interfering RNA, including but not limited to a small interfering RNA ("siRNA") or a small hairpin RNA ("shRNA"). Methods for constructing interfering RNAs are well known in the art. For example, the interfering RNA can be assembled from two separate oligonucleotides, where one strand is the sense strand and the other is the antisense strand, wherein the antisense and sense strands are self-complementary (i.e., each strand comprises nucleotide sequence that is complementary to nucleotide sequence in the other strand; such as where the antisense strand and sense strand form a duplex or double stranded structure); the antisense strand comprises nucleotide sequence that is complementary to a nucleotide sequence in a target nucleic acid molecule or a portion thereof (i.e., an undesired gene) and the sense strand comprises nucleotide sequence corresponding to the target nucleic acid sequence or a portion thereof. Alternatively, interfering RNA is assembled from a single oligonucleotide, where the self-complementary sense and antisense regions are linked by means of nucleic acid based or non-nucleic acid-based linker(s). The interfering RNA can be a polynucleotide with a duplex, asymmetric duplex, hairpin or asymmetric hairpin secondary structure, having self-complementary sense and antisense regions, wherein the antisense region comprises a nucleotide sequence that is complementary to nucleotide sequence in a separate target nucleic acid molecule or a portion thereof and the sense region having nucleotide sequence corresponding to the target nucleic acid sequence or a portion thereof. The interfering can be a circular single-stranded polynucleotide having two or more loop structures and a stem comprising self-complementary sense and antisense regions, wherein the antisense region comprises nucleotide sequence that is complementary to nucleotide sequence in a target nucleic acid molecule or a portion thereof and the sense region having nucleotide sequence corresponding to the target nucleic acid sequence or a portion thereof, and wherein the circular polynucleotide can be processed either in vivo or in vitro to generate an active siRNA molecule capable of mediating RNA interference. RNA interference may cause translational repression and degradation of target mRNAs with imperfect complementarity or sequence-specific cleavage of perfectly complementary mRNAs.

In some embodiments, the interfering RNA coding region encodes a self-complementary RNA molecule having a sense region, an antisense region and a loop region. Such an RNA molecule when expressed desirably forms a "hairpin" structure, and is referred to herein as an "shRNA." The loop region is generally between about 2 and about 10 nucleotides in length. In some embodiments, the loop region is from about 6 to about 9 nucleotides in length. In some embodiments, the sense region and the antisense region are between about 15 and about 20 nucleotides in length. Following post-transcriptional processing, the small hairpin RNA is converted into a siRNA by a cleavage event mediated by the enzyme Dicer, which is a member of the RNase III family. The siRNA is then capable of inhibiting the expression of a gene with which it shares homology. After the siRNA has cleaved its target, it is released from that RNA to search for another target and can repeatedly bind and cleave new targets (Brummelkamp (2002) Science 296:550-553; Lee (2002) Nature Biotechnol., 20, 500-505; Miyagishi and Taira (2002) Nature Biotechnol 20:497-500; Paddison (2002) Genes & Dev. 16:948-958; Paul (2002) Nature Biotechnol 20, 505-508; Sui (2002) Proc. Natl. Acad. Sd. USA 99(6), 5515-5520; Yu (2002) Proc Natl Acad Sci USA 99:6047-6052; Peer and Lieberman (2011) Gen Ther 18, 1127-1133).

The target RNA cleavage reaction guided by siRNAs is highly sequence specific. In general, siRNA containing a nucleotide sequences identical to a portion of the target nucleic acid are preferred for inhibition. However, 100% sequence identity between the siRNA and the target gene is not required to practice the present invention. Thus the invention has the advantage of being able to tolerate sequence variations that might be expected due to genetic mutation, strain polymorphism, or evolutionary divergence. For example, siRNA sequences with insertions, deletions, and single point mutations relative to the target sequence have also been found to be effective for inhibition. Alternatively, siRNA sequences with nucleotide analog substitutions or insertions can be effective for inhibition. In general the siRNAs must retain specificity for their target, i.e., must not directly bind to, or directly significantly affect expression levels of, transcripts other than the intended target. shRNAs that are constitutively expressed form promoters can ensure long-term gene silencing. Most methods commonly used for delivery of siRNAs rely on commonly used techniques for introducing an exogenous nucleic acid into a cell including calcium phosphate or calcium chloride precipitation, microinjection, DEAE-dextran-mediated transfection, lipofection, commercially available cationic polymers and lipids and cell-penetrating peptides, electroporation or stable nucleic acid-lipid particles (SNALPs), all of which are routine in the art. siRNAs can also be conjugated to small molecules to direct binding to cell-surface receptors, such as cholesterol (Wolfrum (2007) Nat Biotechnol 25:1149-1157), alpha-tocopherol (Nishina (2008) Mol Ther 16:734-40), lithocholic acid or lauric acid (Lorenz (2004) Bioorg Med Chem Lett 14:4975-4977), polyconjugates (Rozema (2007) PNAS 104:12982-12987). A variation of conjugated siRNAs are aptamer-siRNA chimeras (McNamara (2006) Nat Biotechnol 24:1005-1015; Dassie (2009) Nat Biotechnol 27:839-849) and siRNA-fusion protein complexes, which is composed of a targeting peptide, such as an antibody fragment that recognizes a cell-surface receptor or ligand, linked to an RNA-binding peptide that can be complexed to siRNAs for targeted systemic siRNA delivery (Yao (2011) Sci Transl Med 4(130):130ra48.

Ribozymes

Trans-cleaving enzymatic nucleic acid molecules can also be used; they have shown promise as therapeutic agents for human disease (Usman & McSwiggen, (1995) Ann. Rep. Med. Chem. 30, 285-294; Christoffersen and Marr (1995) J. Med. Chem. 38, 2023-2037; Weng (2005) Mol Cancer Ther 4, 948-955; Armado (2004) Hum Gene Ther 15, 251-262; Macpherson (2005) J Gene Med 7, 552-564; Muhlbacher (2010) Curr Opin Pharamacol 10(5):551-6). Enzymatic nucleic acid molecules can be designed to cleave specific p40 and/or CD5L targets within the background of cellular RNA. Such a cleavage event renders the p40 and/or CD5L non-functional.

In general, enzymatic nucleic acids with RNA cleaving activity act by first binding to a target RNA. Such binding occurs through the target binding portion of an enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel (1979) Proc. R. Soc. London B 205, 435) have been used to evolve new nucleic acid catalysts with improved properties, new functions and capable of catalyzing a variety of reactions, such as cleavage and ligation of phosphodiester linkages and amide linkages, (Joyce (1989) Gene 82, 83-87; Beaudry (1992) Science 257, 635-641; Joyce (1992) Scientific American 267, 90-97; Breaker (1994) TIBTECH 12, 268; Bartel (1993) Science 261:1411-1418; Szostak (1993) TIBS 17, 89-93; Kumar (1995) FASEB J. 9, 1183; Breaker (1996) Curr. Op. Biotech. 1, 442; Scherer (2003) Nat Biotechnol 21, 1457-1465; Berens (2015) Curr. Op. Biotech. 31, 10-15). Ribozymes can also be engineered to be allosterically activated by effector molecules (riboswitches, Liang (2011) Mol Cell 43, 915-926; Wieland (2010) Chem Biol 17, 236-242; U.S. Pat. No. 8,440,810). The development of ribozymes that are optimal for catalytic activity would contribute significantly to any strategy that employs RNA-cleaving ribozymes for the purpose of regulating gene expression. The most common ribozyme therapeutics are derived from either hammerhead or hairpin/paperclip motifs. The hammerhead ribozyme, for example, functions with a catalytic rate (kcat) of about 1 min-1 in the presence of saturating (10 rnM) concentrations of Mg2+ cofactor. An artificial "RNA ligase" ribozyme has been shown to catalyze the corresponding self-modification reaction with a rate of about 100 min-1. In addition, it is known that certain modified hammerhead ribozymes that have substrate binding arms made of DNA catalyze RNA cleavage with multiple turn-over rates that approach 100 min-1. Ribozymes can be delivered to target cells in RNA form or can be transcribed from vectors. Due to poor stability of fully-RNA ribozymes, ribozymes often require chemical modification, such as, 5'-PS backbone linkage, 2'-O-Me, 2'-deoxy-2'-C-allyl uridine, and terminal inverted 3'-3' deoxyabasic nucleotides (Kobayashi (2005) Cancer Chemother Pharmacol 56, 329-336).

CRISPR/Cas, TALENs, and Zinc Finger Nucleases (ZFNs)

As mentioned above, some embodiments comprise methods gene targeting and/or genome editing. Such methods are useful, e.g., in the context of decreasing protein expression in vivo and/or modifying cells in vitro (e.g., in the context of adoptive cell therapies). In some embodiments, genes are targeting and/or edited using DNA binding proteins. In some embodiments, the methods described herein include the use of transcription activator effector-like nucleases (TALENs), Clustered Regularly Interspaced Short Palindromic Repeats (CRISPR) Cas RNA-guided nucleases (RGNs), or zinc finger nucleases (ZFNs) to inhibit expression of CD5L and/or p40. In these methods, engineered nucleases are used to specifically target and disrupt expression of CD5L and/or p40. Methods for using CRISPR, TALENs, and ZFNs are well known in the art.

Gene Targeting and Genome Editing

As mentioned above, some embodiments comprise methods gene targeting and/or genome editing. Such methods are useful, e.g., in the context of decreasing protein expression in vivo and/or modifying cells in vitro (e.g., in the context of adoptive cell therapies). In some embodiments, genes are targeting and/or edited using DNA binding proteins.

In certain embodiments, the DNA binding protein is a (endo)nuclease or a variant thereof having altered or modified activity (i.e. a modified nuclease, as described herein elsewhere). In certain embodiments, said nuclease is a targeted or site-specific or homing nuclease or a variant thereof having altered or modified activity. In certain embodiments, said nuclease or targeted/site-specific/homing nuclease is, comprises, consists essentially of, or consists of a (modified) CRISPR/Cas system or complex, a (modified) Cas protein, a (modified) zinc finger, a (modified) zinc finger nuclease (ZFN), a (modified) transcription factor-like effector (TALE), a (modified) transcription factor-like effector nuclease (TALEN), or a (modified) meganuclease. In certain embodiments, said (modified) nuclease or targeted/site-specific/homing nuclease is, comprises, consists essentially of, or consists of a (modified) RNA-guided nuclease. As used herein, the term "Cas" generally refers to a (modified) effector protein of the CRISPR/Cas system or complex, and can be without limitation a (modified) Cas9, or other enzymes such as Cpf1, The term "Cas" may be used herein interchangeably with the terms "CRISPR" protein, "CRISPR/Cas protein", "CRISPR effector", "CRISPR/Cas effector", "CRISPR enzyme", "CRISPR/Cas enzyme" and the like, unless otherwise apparent, such as by specific and exclusive reference to Cas9. It is to be understood that the term "CRISPR protein" may be used interchangeably with "CRISPR enzyme", irrespective of whether the CRISPR protein has altered, such as increased or decreased (or no) enzymatic activity, compared to the wild type CRISPR protein. Likewise, as used herein, in certain embodiments, where appropriate and which will be apparent to the skilled person, the term "nuclease" may refer to a modified nuclease wherein catalytic activity has been altered, such as having increased or decreased nuclease activity, or no nuclease activity at all, as well as nickase activity, as well as otherwise modified nuclease as defined herein elsewhere, unless otherwise apparent, such as by specific and exclusive reference to unmodified nuclease.

As used herein, the term "targeting" of a selected nucleic acid sequence means that a nuclease or nuclease complex is acting in a nucleotide sequence specific manner. For instance, in the context of the CRISPR/Cas system, the guide RNA is capable of hybridizing with a selected nucleic acid sequence. As uses herein, "hybridization" or "hybridizing" refers to a reaction in which one or more polynucleotides react to form a complex that is stabilized via hydrogen bonding between the bases of the nucleotide residues. The hydrogen bonding may occur by Watson Crick base pairing, Hoogsteen binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PGR, or the cleavage of a polynucleotide by an enzyme. A sequence capable of hybridizing with a given sequence is referred to as the "complement" of the given sequence.

In certain embodiments, the DNA binding protein is a (modified) transcription activator-like effector nuclease (TALEN) system. Transcription activator-like effectors (TALEs) can be engineered to bind practically any desired DNA sequence. Exemplary methods of genome editing using the TALEN system can be found for example in Cermak T. Doyle E L. Christian M. Wang L. Zhang Y. Schmidt C, et al. Efficient design and assembly of custom TALEN and other TAL effector-based constructs for DNA targeting. Nucleic Acids Res. 2011; 39:e82; Zhang F. Cong L. Lodato S. Kosuri S. Church G M. Arlotta P Efficient construction of sequence-specific TAL effectors for modulating mammalian transcription. Nat Biotechnol. 2011; 29:149-153 and U.S. Pat. Nos. 8,450,471, 8,440,431 and 8,440,432, all of which are specifically incorporated by reference. By means of further guidance, and without limitation, naturally occurring TALEs or "wild type TALEs" are nucleic acid binding proteins secreted by numerous species of proteobacteria. TALE polypeptides contain a nucleic acid binding domain composed of tandem repeats of highly conserved monomer polypeptides that are predominantly 33, 34 or 35 amino acids in length and that differ from each other mainly in amino acid positions 12 and 13. In advantageous embodiments the nucleic acid is DNA. As used herein, the term "polypeptide monomers", or "TALE monomers" will be used to refer to the highly conserved repetitive polypeptide sequences within the TALE nucleic acid binding domain and the term "repeat variable di-residues" or "RVD" will be used to refer to the highly variable amino acids at positions 12 and 13 of the polypeptide monomers. As provided throughout the disclosure, the amino acid residues of the RVD are depicted using the IUPAC single letter code for amino acids. A general representation of a TALE monomer which is comprised within the DNA binding domain is $X_{1-11}$-($X_{12}X_{13}$)—$X_{14-33}$ or 34 or 35, where the subscript indicates the amino acid position and X represents any amino acid. $X_{12}X_{13}$ indicate the RVDs. In some polypeptide monomers, the variable amino acid at position 13 is missing or absent and in such polypeptide monomers, the RVD consists of a single amino acid. In such cases the RVD may be alternatively represented as X*, where X represents X12 and (*) indicates that X13 is absent. The DNA binding domain comprises several repeats of TALE monomers and this may be represented as (X1-11-(X12X13)—X14-33 or 34 or 35)z, where in an advantageous embodiment, z is at least 5 to 40. In a further advantageous embodiment, z is at least 10 to 26. The TALE monomers have a nucleotide binding affinity that is determined by the identity of the amino acids in its RVD. For example, polypeptide monomers with an RVD of NI preferentially bind to adenine (A), polypeptide monomers with an RVD of NG preferentially bind to thymine (T), polypeptide monomers with an RVD of HD preferentially bind to cytosine (C) and polypeptide monomers with an RVD of NN preferentially bind to both adenine (A) and guanine (G). In yet another embodiment of the invention, polypeptide monomers with an RVD of IG preferentially bind to T. Thus, the number and order of the polypeptide monomer repeats in the nucleic acid binding domain of a TALE determines its nucleic acid target specificity. In still further embodiments of the invention, polypeptide monomers with an RVD of NS recognize all four base pairs and may bind to A, T, G or C. The structure and function of TALEs is further described in, for example, Moscou et al., Science 326:1501 (2009); Boch et al., Science 326:1509-1512 (2009); and Zhang et al., Nature Biotechnology 29:149-153 (2011), each of which is incorporated by reference in its entirety.

In certain embodiments, the nucleic acid modification is effected by a (modified) zinc-finger nuclease (ZFN) system. The ZFN system uses artificial restriction enzymes generated by fusing a zinc finger DNA-binding domain to a DNA-cleavage domain that can be engineered to target desired DNA sequences. Exemplary methods of genome editing using ZFNs can be found for example in U.S. Pat. Nos. 6,534,261, 6,607,882, 6,746,838, 6,794,136, 6,824,978, 6,866,997, 6,933,113, 6,979,539, 7,013,219, 7,030,215, 7,220,719, 7,241,573, 7,241,574, 7,585,849, 7,595,376, 6,903,185, and 6,479,626, all of which are specifically incorporated by reference. By means of further guidance, and without limitation, artificial zinc-finger (ZF) technology involves arrays of ZF modules to target new DNA-binding sites in the genome. Each finger module in a ZF array targets three DNA bases. A customized array of individual zinc finger domains is assembled into a ZF protein (ZFP). ZFPs can comprise a functional domain. The first synthetic zinc finger nucleases (ZFNs) were developed by fusing a ZF protein to the catalytic domain of the Type IIS restriction enzyme FokI. (Kim, Y. G. et al., 1994, Chimeric restriction endonuclease, Proc. Natl. Acad. Sci. U.S.A. 91, 883-887; Kim, Y. G. et al., 1996, Hybrid restriction enzymes: zinc finger fusions to Fok I cleavage domain. Proc. Natl. Acad. Sci. U.S.A. 93, 1156-1160). Increased cleavage specificity can be attained with decreased off target activity by use of paired ZFN heterodimers, each targeting different nucleotide sequences separated by a short spacer. (Doyon, Y. et al., 2011, Enhancing zinc-finger-nuclease activity with improved obligate heterodimeric architectures. Nat. Methods 8, 74-79). ZFPs can also be designed as transcription activators and repressors and have been used to target many genes in a wide variety of organisms.

In certain embodiments, the nucleic acid modification is effected by a (modified) meganuclease, which are endodeoxyribonucleases characterized by a large recognition site (double-stranded DNA sequences of 12 to 40 base pairs). Exemplary method for using meganucleases can be found in U.S. Pat. Nos. 8,163,514; 8,133,697; 8,021,867; 8,119,361; 8,119,381; 8,124,369; and 8,129,134, which are specifically incorporated by reference.

In certain embodiments, the nucleic acid modification is effected by a (modified) CRISPR/Cas complex or system. With respect to general information on CRISPR/Cas Systems, components thereof, and delivery of such components, including methods, materials, delivery vehicles, vectors, particles, and making and using thereof, including as to amounts and formulations, as well as Cas9 CRISPR/Cas-expressing eukaryotic cells, Cas-9 CRISPR/Cas expressing eukaryotes, such as a mouse, reference is made to: U.S. Pat. Nos. 8,999,641, 8,993,233, 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213,991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105,035), US 2014-0186958 (U.S. application Ser. No. 14/105,017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), WO2015/058052 (PCT/US2014/061077), WO2015070083 (PCT/US2014/064663), WO2015/089354 (PCT/US2014/069902), WO2015/089351 (PCT/US2014/069897), WO2015/089364 (PCT/US2014/069925), WO2015/089427 (PCT/US2014/070068), WO2015/089473 (PCT/US2014/070152), WO2015/089486 (PCT/US2014/070175), WO/2016/04925 (PCT/US2015/

051830), WO/2016/094867 (PCT/US2015/065385), WO/2016/094872 (PCT/US2015/065393), WO/2016/094874 (PCT/US2015/065396), WO/2016/106244 (PCT/US2015/067177).

Reference is further made to Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013); RNA-guided editing of bacterial genomes using CRISPR-Cas systems. Jiang W., Bikard D., Cox D., Zhang F, Marraffini L A. Nat Biotechnol March; 31(3):233-9 (2013); One-Step Generation of Mice Carrying Mutations in Multiple Genes by CRISPR-Cas-Mediated Genome Engineering. Wang H., Yang H., Shivalila C S., Dawlaty M M., Cheng A W., Zhang F., Jaenisch R. Cell May 9; 153(4):910-8 (2013); Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. 2013 Aug. 22; 500(7463):472-6. doi: 10.1038/Nature12466. Epub 2013 Aug. 23; Double Nicking by RNA-Guided CRISPR Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13) 01015-5. (2013); DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013); Genome engineering using the CRISPR-Cas9 system. Ran, F A., Hsu, P D., Wright, J., Agarwala, V., Scott, D A., Zhang, F. Nature Protocols November; 8(11):2281-308. (2013); Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print]; Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27. (2014). 156(5):935-49; Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. (2014) April 20. doi: 10.1038/nbt.2889; CRISPR-Cas9 Knockin Mice for Genome Editing and Cancer Modeling, Platt et al., Cell 159(2): 440-455 (2014) DOI: 10.1016/j.cell.2014.09.014; Development and Applications of CRISPR-Cas9 for Genome Engineering, Hsu et al, Cell 157, 1262-1278 (Jun. 5, 2014) (Hsu 2014); Genetic screens in human cells using the CRISPR/Cas9 system, Wang et al., Science. 2014 Jan. 3; 343(6166): 80-84. doi:10.1126/science.1246981; Rational design of highly active sgRNAs for CRISPR-Cas9-mediated gene inactivation, Doench et al., Nature Biotechnology 32(12):1262-7 (2014) published online 3 Sep. 2014; doi:10.1038/nbt.3026, and In vivo interrogation of gene function in the mammalian brain using CRISPR-Cas9, Swiech et al, Nature Biotechnology 33, 102-106 (2015) published online 19 Oct. 2014; doi:10.1038/nbt.3055, Cpf1 is a Single RNA-Guided Endonuclease of a Class 2 CRISPR-Cas System, Zetsche et al., Cell 163, 1-13 (2015); Discovery and Functional Characterization of Diverse Class 2 CRISPR-Cas Systems, Shmakov et al., Mol Cell 60(3): 385-397 (2015); Each of these publications, patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Preferred DNA binding proteins are CRISPR/Cas enzymes or variants thereof. In certain embodiments, the CRISPR/Cas protein is a class 2 CRISPR/Cas protein. In certain embodiments, said CRISPR/Cas protein is a type II, type V, or type VI CRISPR/Cas protein. The CRISPR/Cas system does not require the generation of customized proteins to target specific sequences but rather a single Cas protein can be programmed by an RNA guide (gRNA) to recognize a specific nucleic acid target, in other words the Cas enzyme protein can be recruited to a specific nucleic acid target locus (which may comprise or consist of RNA and/or DNA) of interest using said short RNA guide.

In general, the CRISPR/Cas or CRISPR system is as used herein foregoing documents refers collectively to elements involved in the expression of or directing the activity of CRISPR-associated ("Cas") proteins or genes, including sequences encoding a Cas protein and a guide RNA. In this context of the guide RNA this may include one or more of, a tracr (trans-activating CRISPR) sequence (e.g. tracrRNA or an active partial tracrRNA), a tracr-mate sequence (encompassing a "direct repeat" and a tracrRNA-processed partial direct repeat in the context of an endogenous CRISPR system), a guide sequence (also referred to as a "spacer" in the context of an endogenous CRISPR system), In general, a CRISPR system is characterized by elements that promote the formation of a CRISPR complex at the site of a target sequence. In the context of formation of a CRISPR complex, "target sequence" refers to a sequence to which a guide sequence is designed to have complementarity, where hybridization between a target DNA sequence and a guide sequence promotes the formation of a CRISPR complex.

In certain embodiments, the gRNA comprises a guide sequence fused to a tracr mate sequence (or direct repeat), and a tracr sequence. In particular embodiments, the guide sequence fused to the tracr mate and the tracr sequence are provided or expressed as discrete RNA sequences. In preferred embodiments, the gRNA is a chimeric guide RNA or single guide RNA (sgRNA), comprising a guide sequence fused to the tracr mate which is itself linked to the tracr sequence. In particular embodiments, the CRISPR/Cas system or complex as described herein does not comprise and/or does not rely on the presence of a tracr sequence (e.g. if the Cas protein is Cpf1).

As used herein, the term "guide sequence" in the context of a CRISPR/Cas system, comprises any polynucleotide sequence having sufficient complementarity with a target nucleic acid sequence to hybridize with the target nucleic acid sequence and direct sequence-specific binding of a nucleic acid-targeting complex to the target nucleic acid sequence. In some embodiments, the degree of complementarity, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies; available at www.novocraft.com), ELAND (Illumina, San Diego, CA), SOAP (available at soap.genomics.org.cn), and Maq (available at maq.sourceforge.net). The ability of a guide sequence (within a nucleic acid-targeting guide RNA) to direct sequence-specific binding of a nucleic acid-targeting complex to a target nucleic acid sequence may be assessed by any suitable assay.

A guide sequence, and hence a nucleic acid-targeting guide RNA may be selected to target any target nucleic acid sequence. The target sequence may be DNA. The target sequence may be genomic DNA. The target sequence may be mitochondrial DNA.

In certain embodiments, the gRNA comprises a stem loop, preferably a single stem loop. In certain embodiments, the direct repeat sequence forms a stem loop, preferably a single stem loop. In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer. In particular embodiments, the CRISPR/Cas system requires a tracrRNA. The "tracrRNA" sequence or analogous terms includes any polynucleotide sequence that has sufficient complementarity with a crRNA sequence to hybridize. In some embodiments, the degree of complementarity between the tracrRNA sequence and crRNA sequence along the length of the shorter of the two when optimally aligned is about or more than about 25%, 30%, 40%, 50%, 60%, 70%, 80%, 90%, 95%, 97.5%, 99%, or higher. In some embodiments, the tracr sequence is about or more than about 5, 6, 7, 8, 9, 10, 11, 12, 13, 14, 15, 16, 17, 18, 19, 20, 25, 30, 40, 50, or more nucleotides in length. In some embodiments, the tracr sequence and gRNA sequence are contained within a single transcript, such that hybridization between the two produces a transcript having a secondary structure, such as a hairpin. In an embodiment of the invention, the transcript or transcribed polynucleotide sequence has at least two or more hairpins. In preferred embodiments, the transcript has two, three, four or five hairpins. In a further embodiment of the invention, the transcript has at most five hairpins. In a hairpin structure the portion of the sequence 5' of the final "N" and upstream of the loop may correspond to the tracr mate sequence, and the portion of the sequence 3' of the loop then corresponds to the tracr sequence. In a hairpin structure the portion of the sequence 5' of the final "N" and upstream of the loop may alternatively correspond to the tracr sequence, and the portion of the sequence 3' of the loop corresponds to the tracr mate sequence. In alternative embodiments, the CRISPR/Cas system does not require a tracrRNA, as is known by the skilled person.

In certain embodiments, the guide RNA (capable of guiding Cas to a target locus) may comprise (1) a guide sequence capable of hybridizing to a target locus and (2) a tracr mate or direct repeat sequence (in 5' to 3' orientation, or alternatively in 3' to 5' orientation, depending on the type of Cas protein, as is known by the skilled person). In particular embodiments, the CRISPR/Cas protein is characterized in that it makes use of a guide RNA comprising a guide sequence capable of hybridizing to a target locus and a direct repeat sequence, and does not require a tracrRNA. In particular embodiments, where the CRISPR/Cas protein is characterized in that it makes use of a tracrRNA, the guide sequence, tracr mate, and tracr sequence may reside in a single RNA, i.e. an sgRNA (arranged in a 5' to 3' orientation or alternatively arranged in a 3' to 5' orientation), or the tracr RNA may be a different RNA than the RNA containing the guide and tracr mate sequence. In these embodiments, the tracr hybridizes to the tracr mate sequence and directs the CRISPR/Cas complex to the target sequence.

In particular embodiments, the DNA binding protein is a catalytically active protein. In these embodiments, the formation of a nucleic acid-targeting complex (comprising a guide RNA hybridized to a target sequence results in modification (such as cleavage) of one or both DNA or RNA strands in or near (e.g., within 1, 2, 3, 4, 5, 6, 7, 8, 9, 10, 20, 50, or more base pairs from) the target sequence. As used herein the term "sequence(s) associated with a target locus of interest" refers to sequences near the vicinity of the target sequence (e.g. within 1, 2, 3, 4, 5, 6, 7, 8, 9, 10, 20, 50, or more base pairs from the target sequence, wherein the target sequence is comprised within a target locus of interest). The skilled person will be aware of specific cut sites for selected CRISPR/Cas systems, relative to the target sequence, which as is known in the art may be within the target sequence or alternatively 3' or 5' of the target sequence.

Accordingly, in particular embodiments, the DNA binding protein has nucleic acid cleavage activity. In some embodiments, the nuclease as described herein may direct cleavage of one or both nucleic acid (DNA, RNA, or hybrids, which may be single or double stranded) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be blunt (e.g. for Cas9, such as SaCas9 or SpCas9). In some embodiments, the cleavage may be staggered (e.g. for Cpf1), i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is upstream of the PAM. In some embodiments, the cleavage site is downstream of the PAM.

In certain embodiments, the target sequence should be associated with a PAM (protospacer adjacent motif) or PFS (protospacer flanking sequence or site); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence). Examples of PAM sequences are given in the examples section below, and the skilled person will be able to identify further PAM sequences for use with a given CRISPR enzyme. Further, engineering of the PAM Interacting (PI) domain may allow programing of PAM specificity, improve target site recognition fidelity, and increase the versatility of the Cas, e.g. Cas9, genome engineering platform. Cas proteins, such as Cas9 proteins may be engineered to alter their PAM specificity, for example as described in Kleinstiver B P et al. Engineered CRISPR-Cas9 nucleases with altered PAM specificities. Nature. 2015 Jul. 23; 523(7561):481-5. doi: 10.1038/nature14592. In some embodiments, the method comprises allowing a CRISPR complex to bind to the target polynucleotide to effect cleavage of said target polynucleotide thereby modifying the target polynucleotide, wherein the CRISPR complex comprises a CRISPR enzyme complexed with a guide sequence hybridized to a target sequence within said target polynucleotide, wherein said guide sequence is linked to a tracr mate sequence which in turn hybridizes to a tracr sequence. The skilled person will understand that other Cas proteins may be modified analogously.

In some embodiments, the nucleic acid-targeting effector protein may be mutated with respect to a corresponding wild-type enzyme such that the mutated nucleic acid-targeting effector protein lacks the ability to cleave one or both DNA strands of a target polynucleotide containing a target sequence. As a further example, two or more catalytic domains of a Cas protein (e.g. RuvC I, RuvC II, and RuvC III or tÿe HNH domain of a Cas9 protein) may be mutated to produce a mutated Cas protein which cleaves only one DNA strand of a target sequence.

In particular embodiments, the nucleic acid-targeting effector protein may be mutated with respect to a corresponding wild-type enzyme such that the mutated nucleic acid-targeting effector protein lacks substantially all DNA cleavage activity. In some embodiments, a nucleic acid-targeting effector protein may be considered to substantially lack all DNA and/or RNA cleavage activity when the cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form.

As used herein, the term "modified" Cas generally refers to a Cas protein having one or more modifications or mutations (including point mutations, truncations, insertions, deletions, chimeras, fusion proteins, etc.) compared to the wild type Cas protein from which it is derived. By derived is meant that the derived enzyme is largely based, in the sense of having a high degree of sequence homology with, a wildtype enzyme, but that it has been mutated (modified) in some way as known in the art or as described herein.

As detailed above, in certain embodiments, the nuclease as referred to herein is modified. As used herein, the term "modified" refers to which may or may not have an altered functionality. By means of example, and in particular with reference to Cas proteins, modifications which do not result in an altered functionality include for instance codon optimization for expression into a particular host, or providing the nuclease with a particular marker (e.g. for visualization). Modifications with may result in altered functionality may also include mutations, including point mutations, insertions, deletions, truncations (including split nucleases), etc., as well as chimeric nucleases (e.g. comprising domains from different orthologues or homologues) or fusion proteins. Fusion proteins may without limitation include for instance fusions with heterologous domains or functional domains (e.g. localization signals, catalytic domains, etc.). Accordingly, in certain embodiments, the modified nuclease may be used as a generic nucleic acid binding protein with fusion to or being operably linked to a functional domain. In certain embodiments, various different modifications may be combined (e.g. a mutated nuclease which is catalytically inactive and which further is fused to a functional domain, such as for instance to induce DNA methylation or another nucleic acid modification, such as including without limitation a break (e.g. by a different nuclease (domain)), a mutation, a deletion, an insertion, a replacement, a ligation, a digestion, a break or a recombination). As used herein, "altered functionality" includes without limitation an altered specificity (e.g. altered target recognition, increased (e.g. "enhanced" Cas proteins) or decreased specificity, or altered PAM recognition), altered activity (e.g. increased or decreased catalytic activity, including catalytically inactive nucleases or nickases), and/or altered stability (e.g. fusions with destabilization domains). Suitable heterologous domains include without limitation a nuclease, a ligase, a repair protein, a methyltransferase, (viral) integrase, a recombinase, a transposase, an argonaute, a cytidine deaminase, a retron, a group II intron, a phosphatase, a phosphorylase, a sulfurylase, a kinase, a polymerase, an exonuclease, etc. Examples of all these modifications are known in the art. It will be understood that a "modified" nuclease as referred to herein, and in particular a "modified" Cas or "modified" CRISPR/Cas system or complex preferably still has the capacity to interact with or bind to the polynucleic acid (e.g. in complex with the gRNA).

By means of further guidance and without limitation, in certain embodiments, the nuclease may be modified as detailed below. As already indicated, more than one of the indicated modifications may be combined. For instance, codon optimization may be combined with NLS or NES fusions, catalytically inactive nuclease modifications or nickase mutants may be combined with fusions to functional (heterologous) domains, etc.

In certain embodiments, the nuclease, and in particular the Cas proteins of prokaryotic origin, may be codon optimized for expression into a particular host (cell). An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667). Whilst this is preferred, it will be appreciated that other examples are possible and codon optimization for a host species other than human, or for codon optimization for specific organs is known. In some embodiments, an enzyme coding sequence encoding a Cas is codon optimized for expression in particular cells, such as eukaryotic cells. The eukaryotic cells may be those of or derived from a particular organism, such as a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g. about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazusa.or.jp/codon/ and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, PA), are also available. In some embodiments, one or more codons (e.g. 1, 2, 3, 4, 5, 10, 15, 20, 25, 50, or more, or all codons) in a sequence encoding a Cas correspond to the most frequently used codon for a particular amino acid. Codon optimization may be for expression into any desired host (cell), including mammalian, plant, algae, or yeast.

In certain embodiments, the nuclease, in particular the Cas protein, may comprise one or more modifications resulting in enhanced activity and/or specificity, such as including mutating residues that stabilize the targeted or non-targeted strand (e.g. eCas9; "Rationally engineered Cas9 nucleases with improved specificity", Slaymaker et al. (2016), Science, 351(6268):84-88, incorporated herewith in its entirety by reference). In certain embodiments, the altered or modified activity of the engineered CRISPR protein comprises increased targeting efficiency or decreased off-target binding. In certain embodiments, the altered activity of the engineered CRISPR protein comprises modified cleavage activity. In certain embodiments, the altered activity comprises increased cleavage activity as to the target polynucleotide loci. In certain embodiments, the altered activity comprises decreased cleavage activity as to the target polynucleotide loci. In certain embodiments, the altered activity comprises decreased cleavage activity as to off-target polynucleotide loci. In certain embodiments, the altered or modified activity of the modified nuclease comprises altered helicase kinetics. In certain embodiments, the modified nuclease comprises a modification that alters association of the protein with the nucleic acid molecule comprising RNA (in the case of a Cas protein), or a strand of the target polynucleotide loci, or a strand of off-target polynucleotide loci. In an aspect of the invention, the engineered CRISPR protein comprises a modification that alters formation of the CRISPR complex. In certain embodiments, the altered activity comprises increased cleavage activity as to off-target polynucleotide loci. Accordingly, in certain embodiments, there is increased specificity for target polynucleotide loci as compared to off-target polynucleotide loci. In other embodiments, there is reduced specificity for target polynucleotide loci as compared to off-target polynucleotide loci. In certain embodiments, the mutations result in decreased off-target effects (e.g. cleavage or binding properties, activity, or kinetics), such as in case for Cas proteins for instance resulting in a lower tolerance for mismatches between target and gRNA. Other mutations may lead to increased off-target effects (e.g. cleavage or binding properties, activity, or kinetics). Other mutations may lead to increased or decreased on-target effects (e.g. cleavage or binding properties, activity, or kinetics). In certain embodiments, the mutations result in altered (e.g. increased or decreased) helicase activity, association or formation of the functional nuclease complex (e.g. CRISPR/Cas complex). In certain embodiments, the mutations result in an altered PAM recognition, i.e. a different PAM may be (in addition or in the alternative) be recognized, compared to the unmodified Cas protein (see e.g. "Engineered CRISPR-Cas9 nucleases with altered PAM specificities", Kleinstiver et al. (2015), Nature, 523(7561):481-485, incorporated herein by reference in its entirety). Particularly preferred mutations include positively charged residues and/or (evolutionary) conserved residues, such as conserved positively charged residues, in order to enhance specificity. In certain embodiments, such residues may be mutated to uncharged residues, such as alanine.

In certain embodiments, the nuclease, in particular the Cas protein, may comprise one or more modifications resulting in a nuclease that has reduced or no catalytic activity, or alternatively (in case of nucleases that target double stranded nucleic acids) resulting in a nuclease that only cleaves one strand, i.e. a nickase. By means of further guidance, and without limitation, for example, an aspartate-to-alanine substitution (D10A) in the RuvC I catalytic domain of Cas9 from S. pyogenes converts Cas9 from a nuclease that cleaves both strands to a nickase (cleaves a single strand). Other examples of mutations that render Cas9 a nickase include, without limitation, H840A, N854A, and N863A. As further guidance, where the enzyme is not SpCas9, mutations may be made at any or all residues corresponding to positions 10, 762, 840, 854, 863 and/or 986 of SpCas9 (which may be ascertained for instance by standard sequence comparison tools). In particular, any or all of the following mutations are preferred in SpCas9: D10A, E762A, H840A, N854A, N863A and/or D986A; as well as conservative substitution for any of the replacement amino acids is also envisaged. As a further example, two or more catalytic domains of Cas9 (RuvC I, RuvC II, and RuvC III or the HNH domain) may be mutated to produce a mutated Cas9 substantially lacking all DNA cleavage activity. In some embodiments, a D10A mutation is combined with one or more of H840A, N854A, or N863A mutations to produce a Cas9 enzyme substantially lacking all DNA cleavage activity. In some embodiments, a Cas is considered to substantially lack all DNA cleavage activity when the DNA cleavage activity of the mutated enzyme is about no more than 25%, 10%, 5%, 1%, 0.1%, 0.01%, or less of the DNA cleavage activity of the non-mutated form of the enzyme; an example can be when the DNA cleavage activity of the mutated form is nil or negligible as compared with the non-mutated form. Thus, the Cas may comprise one or more mutations and may be used as a generic DNA binding protein with or without fusion to a functional domain. The mutations may be artificially introduced mutations or gain- or loss-of-function mutations. The mutations may include but are not limited to mutations in one of the catalytic domains (e.g., D10 and H840) in the RuvC and HNH catalytic domains respectively; or the CRISPR enzyme can comprise one or more mutations selected from the group consisting of D10A, E762A, H840A, N854A, N863A or D986A and/or one or more mutations in a RuvC1 or HNH domain of the Cas or has a mutation as otherwise as discussed herein.

In certain embodiments, the nuclease is a split nuclease (see e.g. "A split-Cas9 architecture for inducible genome editing and transcription modulation", Zetsche et al. (2015), Nat Biotechnol. 33(2):139-42, incorporated herein by reference in its entirety). In a split nuclease, the activity (which may be a modified activity, as described herein elsewhere), relies on the two halves of the split nuclease to be joined, i.e. each half of the split nuclease does not possess the required activity, until joined. As further guidance, and without limitation, with specific reference to Cas9, a split Cas9 may result from splitting the Cas9 at any one of the following split points, according or with reference to SpCas9: a split position between 202A/203S; a split position between 255F/256D; a split position between 310E/3111; a split position between 534R/535K; a split position between 572E/573C; a split position between 713S/714G; a split position between 1003L/1004E; a split position between 1054G/1055E; a split position between 1114N/1115S; a split position between 1152K/1153S; a split position between 1245K/1246G; or a split between 1098 and 1099. Identifying potential split sides is most simply done with the help of a crystal structure. For Sp mutants, it should be readily apparent what the corresponding position for, for example, a sequence alignment. For non-Sp enzymes one can use the crystal structure of an ortholog if a relatively high degree of homology exists between the ortholog and the intended Cas9. Ideally, the split position should be located within a region or loop. Preferably, the split position occurs where an interruption of the amino acid sequence does not result in the partial or full destruction of a structural feature (e.g. alpha-helixes or beta-sheets). Unstructured regions (regions that did not show up in the crystal structure because these regions are not structured enough to be "frozen" in a crystal) are often preferred options. In certain embodiments, a functional domain may be provided on each of the split halves, thereby allowing the formation of homodimers or heterodimers. The functional domains may be (inducible) interact, thereby joining the split halves, and reconstituting (modified) nuclease activity. By means of example, an inducer energy source may inducibly allow dimerization of the split halves, through appropriate fusion partners. An inducer energy source may be considered to be simply an inducer or a dimerizing agent. The term 'inducer energy source' is used herein throughout for consistency. The inducer energy source (or inducer) acts to reconstitute the Cas9. In some embodiments, the inducer energy source brings the two parts of the Cas9 together through the action of the two halves of the inducible dimer. The two halves of the inducible dimer therefore are brought tougher in the presence of the inducer energy source. The two halves of the dimer will not form into the dimer (dimerize) without the inducer energy source. Thus, the two halves of the inducible dimer cooperate with the inducer energy source to dimerize the dimer. This in turn reconstitutes the Cas9 by bringing the first and second parts of the Cas9 together. The CRISPR enzyme fusion constructs each comprise one part of the split Cas9. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer. The Cas9 is split in the sense that the two parts of the Cas9 enzyme substantially comprise a functioning Cas9. That Cas9 may function as a genome editing enzyme (when forming a complex with the target DNA and the guide), such as a nickase or a nuclease (cleaving both strands of the DNA), or it may be a deadCas9 which is essentially a DNA-binding protein with very little or no catalytic activity, due to typically two or more mutations in its catalytic domains as described herein further.

In certain embodiments, the nuclease may comprise one or more additional (heterologous) functional domains, i.e. the modified nuclease is a fusion protein comprising the nuclease itself and one or more additional domains, which may be fused C-terminally or N-terminally to the nuclease, or alternatively inserted at suitable and appropriate sited internally within the nuclease (preferably without perturbing its function, which may be an otherwise modified function, such as including reduced or absent catalytic activity, nickase activity, etc.). any type of functional domain may suitably be used, such as without limitation including functional domains having one or more of the following activities: (DNA or RNA) methyltransferase activity, methylase activity, demethylase activity, DNA hydroxylmethylase domain, histone acetylase domain, histone deacetylases domain, transcription or translation activation activity, transcription or translation repression activity, transcription or translation release factor activity, histone modification activity, nuclease activity, single-strand RNA cleavage activity, double-strand RNA cleavage activity, single-strand DNA cleavage activity, double-strand DNA cleavage activity, nucleic acid binding activity, a protein acetyltransferase, a protein deacetylase, a protein methyltransferase, a protein deaminase, a protein kinase, a protein phosphatase, transposase domain, integrase domain, recombinase domain, resolvase domain, invertase domain, protease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinidase, histone tail protease, HDACs, histone methyltransferases (HMTs), and histone acetyltransferase (HAT) inhibitors, as well as HDAC and HMT recruiting proteins, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains. In some embodiments, the functional domain is an epigenetic regulator; see, e.g., Zhang et al., U.S. Pat. No. 8,507,272 (incorporated herein by reference in its entirety). In some embodiments, the functional domain is a transcriptional activation domain, such as VP64, p65, MyoD1, HSF1, RTA, SETT/9 or a histone acetyltransferase. In some embodiments, the functional domain is a transcription repression domain, such as KRAB. In some embodiments, the transcription repression domain is SID, or concatemers of SID (eg SID4X), NuE, or NcoR. In some embodiments, the functional domain is an epigenetic modifying domain, such that an epigenetic modifying enzyme is provided. In some embodiments, the functional domain is an activation domain, which may be the P65 activation domain. In some embodiments, the functional domain comprises nuclease activity. In one such embodiment, the functional domain may comprise FokI. Mention is made of U.S. Pat. Pub. 2014/0356959, U.S. Pat. Pub. 2014/0342456, U.S. Pat. Pub. 2015/0031132, and Mali, P. et al., 2013, Science 339(6121):823-6, doi: 10.1126/science.1232033, published online 3 Jan. 2013 and through the teachings herein the invention comprehends methods and materials of these documents applied in conjunction with the teachings herein. It is to be understood that also destabilization domains or localization domains as described herein elsewhere are encompassed by the generic term "functional domain". In certain embodiments, one or more functional domains are associated with the nuclease itself. In some embodiments, one or more functional domains are associated with an adaptor protein, for example as used with the modified guides of Konnerman et al. (Nature 517(7536): 583-588, 2015; incorporated herein by reference in its entirety), and hene form part of a Synergistic activator mediator (SAM) complex. The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains.

In certain embodiments, the nuclease, in particular the Cas protein, may comprise one or more modifications resulting in a destabilized nuclease when expressed in a host (cell). Such may be achieved by fusion of the nuclease with a destabilization domain (DD). Destabilizing domains have general utility to confer instability to a wide range of proteins; see, e.g., Miyazaki, J Am Chem Soc. Mar. 7, 2012; 134(9): 3942-3945, incorporated herein by reference. CMP8 or 4-hydroxytamoxifen can be destabilizing domains. More generally, A temperature-sensitive mutant of mammalian DHFR (DHFRts), a destabilizing residue by the N-end rule, was found to be stable at a permissive temperature but unstable at 37° C. The addition of methotrexate, a high-affinity ligand for mammalian DHFR, to cells expressing DHFRts inhibited degradation of the protein partially. This was an important demonstration that a small molecule ligand can stabilize a protein otherwise targeted for degradation in cells. A rapamycin derivative was used to stabilize an unstable mutant of the FRB domain of mTOR (FRB*) and restore the function of the fused kinase, GSK-3β.6,7 This system demonstrated that ligand-dependent stability represented an attractive strategy to regulate the function of a specific protein in a complex biological environment. A system to control protein activity can involve the DD becoming functional when the ubiquitin complementation occurs by rapamycin induced dimerization of FK506-binding protein and FKBP12. Mutants of human FKBP12 or ecDHFR protein can be engineered to be metabolically unstable in the absence of their high-affinity ligands, Shield-1 or trimethoprim (TMP), respectively. These mutants are some of the possible destabilizing domains (DDs) useful in the practice of the invention and instability of a DD as a fusion with a CRISPR enzyme confers to the CRISPR protein degradation of the entire fusion protein by the proteasome. Shield-1 and TMP bind to and stabilize the DD in a dose-dependent manner. The estrogen receptor ligand binding domain (ERLBD, residues 305-549 of ERS1) can also be engineered as a destabilizing domain. Since the estrogen receptor signaling pathway is involved in a variety of diseases such as breast cancer, the pathway has been widely studied and numerous agonist and antagonists of estrogen receptor have been developed. Thus, compatible pairs of ERLBD and drugs are known. There are ligands that bind to mutant but not wild-type forms of the ERLBD. By using one of these mutant domains encoding three mutations (L384M, M421G, G521R)12, it is possible to regulate the stability of an ERLBD-derived DD using a ligand that does not perturb endogenous estrogen-sensitive networks. An additional mutation (Y537S) can be introduced to further destabilize the ERLBD and to configure it as a potential DD candidate. This tetra-mutant is an advantageous DD development. The mutant ERLBD can be fused to a CRISPR enzyme and its stability can be regulated or perturbed using a ligand, whereby the CRISPR enzyme has a DD. Another DD can be a 12-kDa (107-amino-acid) tag based on a mutated FKBP protein, stabilized by Shield-1 ligand; see, e.g., Nature Methods 5, (2008). For instance a DD can be a modified FK506 binding protein 12 (FKBP12) that binds to and is reversibly stabilized by a synthetic, biologically inert small molecule, Shield-1; see, e.g., Banaszynski L A, Chen L C, Maynard-Smith L A, Ooi A G, Wandless T J. A rapid, reversible, and tunable method to regulate protein function in living cells using synthetic small molecules. Cell. 2006; 126:995-1004; Banaszynski L A, Sellmyer M A, Contag C H, Wandless T J, Thorne S H. Chemical control of protein stability and function in living mice. Nat Med. 2008; 14:1123-1127; Maynard-Smith L A, Chen L C, Banaszynski L A, Ooi A G, Wandless T J. A directed approach for engineering conditional protein stability using biologically silent small molecules. The Journal of biological chemistry. 2007; 282:24866-24872; and Rodriguez, Chem Biol. Mar. 23, 2012; 19(3): 391-398—all of which are incorporated herein by reference and may be employed in the practice of the invention in selected a DD to associate with a CRISPR enzyme in the practice of this invention. As can be seen, the knowledge in the art includes a number of DDs, and the DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the CRISPR enzyme and hence the CRISPR-Cas complex or system to be regulated or controlled—turned on or off so to speak, to thereby provide means for regulation or control of the system, e.g., in an in vivo or in vitro environment. For instance, when a protein of interest is expressed as a fusion with the DD tag, it is destabilized and rapidly degraded in the cell, e.g., by proteasomes. Thus, absence of stabilizing ligand leads to a D associated Cas being degraded. When a new DD is fused to a protein of interest, its instability is conferred to the protein of interest, resulting in the rapid degradation of the entire fusion protein. Peak activity for Cas is sometimes beneficial to reduce off-target effects. Thus, short bursts of high activity are preferred. The present invention is able to provide such peaks. In some senses the system is inducible. In some other senses, the system repressed in the absence of stabilizing ligand and de-repressed in the presence of stabilizing ligand. By means of example, and without limitation, in some embodiments, the DD is ER50. A corresponding stabilizing ligand for this DD is, in some embodiments, 4HT. As such, in some embodiments, one of the at least one DDs is ER50 and a stabilizing ligand therefor is 4HT or CMP8. In some embodiments, the DD is DHFR50. A corresponding stabilizing ligand for this DD is, in some embodiments, TMP. As such, in some embodiments, one of the at least one DDs is DHFR50 and a stabilizing ligand therefor is TMP. In some embodiments, the DD is ER50. A corresponding stabilizing ligand for this DD is, in some embodiments, CMP8. CMP8 may therefore be an alternative stabilizing ligand to 4HT in the ER50 system. While it may be possible that CMP8 and 4HT can/should be used in a competitive matter, some cell types may be more susceptible to one or the other of these two ligands, and from this disclosure and the knowledge in the art the skilled person can use CMP8 and/or 4HT. More than one (the same or different) DD may be present, and may be fused for instance C-terminally, or N-terminally, or even internally at suitable locations. Having two or more DDs which are heterologous may be advantageous as it would provide a greater level of degradation control.

In some embodiments, the fusion protein as described herein may comprise a linker between the nuclease and the fusion partner (e.g. functional domain). In some embodiments, the linker is a GlySer linker. Attachment of a functional domain or fusion protein can be via a linker, e.g., a flexible glycine-serine (GlyGlyGlySer) or (GGGS)3 or a rigid alpha-helical linker such as (Ala(GluAlaAlaAlaLys) Ala). Linkers such as (GGGGS)3 are preferably used herein to separate protein or peptide domains. (GGGGS)3 is preferable because it is a relatively long linker (15 amino acids). The glycine residues are the most flexible and the serine residues enhance the chance that the linker is on the outside of the protein. (GGGGS)6 (GGGGS)9 or (GGGGS)12 may preferably be used as alternatives. Other preferred alternatives are (GGGGS)1, (GGGGS)2, (GGGGS)4, (GGGGS)5, (GGGGS)7, (GGGGS)8, (GGGGS)10, or (GGGGS)11. Alternative linkers are available, but highly flexible linkers are thought to work best to allow for maximum opportunity for the 2 parts of the Cas9 to come together and thus reconstitute Cas9 activity. One alternative is that the NLS of nucleoplasmin can be used as a linker. For example, a linker can also be used between the Cas9 and any functional domain. Again, a (GGGGS)3 linker may be used here (or the 6, 9, or 12 repeat versions therefore) or the NLS of nucleoplasmin can be used as a linker between Cas9 and the functional domain.

In some embodiments, the nuclease is fused to one or more localization signals, such as nuclear localization sequences (NLSs), such as about or more than about 1, 2, 3, 4, 5, 6, 7, 8, 9, 10, or more NLSs. In some embodiments, the nuclease comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g. zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In a preferred embodiment of the invention, the nuclease comprises at most 6 NLSs. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV;

the NLS from nucleoplasmin (e.g. the nucleoplasmin bipartite NLS with the sequence KRPAATKKAGQAKKKK); the c-myc NLS having the amino acid sequence PAAKRVKLD or RQRRNELKRSP; the hRNPA1 M9 NLS having the sequence NQSSNFGPMKGGNFGGRSSGPYGGGGQYFAKPRNQGGY; the sequence RMRIZFKNKGKDTAELRRRRVEVSVELRKAKKDEQILKRRNV of the IBB domain from importin-alpha; the sequences VSRKRPRP and PPKKARED of the myoma T protein; the sequence POPKKKPL of human p53; the sequence SALIKKKKKMAP of mouse c-abl IV; the sequences DRLRR and PKQKKRK of the influenza virus NS1; the sequence RKLKKKIKKL of the Hepatitis virus delta antigen; the sequence REKKKFLKRR of the mouse Mx1 protein; the sequence KRKGDEVDGVDEVAKKKSKK of the human poly(ADP-ribose) polymerase; and the sequence RKCLQAGMNLEARKTKK of the steroid hormone receptors (human) glucocorticoid.

With particular reference to the CRISPR/Cas system as described herein, besides the Cas protein, in addition or in the alternative, the gRNA and/or tracr (where applicable) and/or tracr mate (or direct repeat) may be modified. Suitable modifications include, without limitation dead guides, escorted guides, protected guides, or guides provided with aptamers, suitable for ligating to, binding or recruiting functional domains (see e.g. also elsewhere herein the reference to synergistic activator mediators (SAM)). Mention is also made of WO/2016/049258 (FUNCTIONAL SCREENING WITH OPTIMIZED FUNCTIONAL CRISPR-CAS SYSTEMS (SAM)), WO/2016/094867 (PROTECTED GUIDE RNAS (PGRNAS); WO/2016/094872 (DEAD GUIDES FOR CRISPR TRANSCRIPTION FACTORS); WO/2016/094874 (ESCORTED AND FUNCTIONALIZED GUIDES FOR CRISPR-CAS SYSTEMS); all incorporated herein by reference. In certain embodiments, the tracr sequence (where appropriate) and/or tracr mate sequence (direct repeat), may comprise one or more protein-interacting RNA aptamers. The one or more aptamers may be located in the tetraloop and/or stemloop 2 of the tracr sequence. The one or more aptamers may be capable of binding MS2 bacteriophage coat protein. In certain embodiments, the gRNA (or trace or tracr mate) is modified by truncations, and/or incorporation of one or more mismatches vis-à-vis the intended target sequence or sequence to hybridize with.

By means of further guidance, and without limitation, in certain embodiments, the gRNA is a dead gRNA (dgRNA), which are guide sequences which are modified in a manner which allows for formation of the CRISPR complex and successful binding to the target, while at the same time, not allowing for successful nuclease activity (i.e. without nuclease activity/without indel activity). These dead guides or dead guide sequences can be thought of as catalytically inactive or conformationally inactive with regard to nuclease activity. Several structural parameters allow for a proper framework to arrive at such dead guides. Dead guide sequences are shorter than respective guide sequences which result in active Cas-specific indel formation. Dead guides are 5%, 10%, 20%, 30%, 40%, 50%, shorter than respective guides directed to the same Cas protein leading to active Cas-specific indel formation. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

By means of further guidance, and without limitation, in certain embodiments, the gRNA is an escorted gRNA (egRNA). By "escorted" is meant that the CRISPR-Cas system or complex or guide is delivered to a selected time or place within a cell, so that activity of the CRISPR-Cas system or complex or guide is spatially or temporally controlled. For example, the activity and destination of the CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The escorted Cpf1 CRISPR-Cas systems or complexes have a gRNA with a functional structure designed to improve gRNA structure, architecture, stability, genetic expression, or any combination thereof. Such a structure can include an aptamer. Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4).

By means of further guidance, and without limitation, in certain embodiments, the gRNA is a protected guide. Protected guides are designed to enhance the specificity of a Cas protein given individual guide RNAs through thermodynamic tuning of the binding specificity of the guide RNA to target nucleic acid. This is a general approach of introducing mismatches, elongation or truncation of the guide sequence to increase/decrease the number of complimentary bases vs. mismatched bases shared between a target and its potential off-target loci, in order to give thermodynamic advantage to targeted genomic loci over genomic off-targets. In certain embodiments, the guide sequence is modified by secondary structure to increase the specificity of the CRISPR-Cas system and whereby the secondary structure can protect against exonuclease activity and allow for 3' additions to the guide sequence. In certain embodiments, a "protector RNA" is hybridized to a guide sequence, wherein the "protector RNA" is an RNA strand complementary to the 5' end of the guide RNA (gRNA), to thereby generate a partially double-stranded gRNA. In an embodiment of the invention, protecting the mismatched bases with a perfectly complementary protector sequence decreases the likelihood of target binding to the mismatched basepairs at the 3' end. In certain embodiments, additional sequences comprising an extended length may also be present. [0004] Guide RNA (gRNA) extensions matching the genomic target provide gRNA protection and enhance specificity. Extension of the gRNA with matching sequence distal to the end of the spacer seed for individual genomic targets is envisaged to provide enhanced specificity. Matching gRNA extensions that enhance specificity have been observed in cells without truncation. Prediction of gRNA structure accompanying these stable length extensions has shown that stable forms arise from protective states, where the extension forms a closed loop with the gRNA seed due to complimentary sequences in the spacer extension and the spacer seed. These results demonstrate that the protected guide concept also includes sequences matching the genomic target sequence distal of the 20mer spacer-binding region. Thermodynamic prediction can be used to predict completely matching or partially matching guide extensions that result in protected gRNA states. This extends the concept of protected gRNAs to interaction between X and Z, where X will generally be of length 17-20 nt and Z is of length 1-30 nt. Thermodynamic prediction can be used to determine the optimal extension state for Z, potentially introducing small numbers of mismatches in Z to promote the formation of protected conformations between X and Z. Throughout the present application, the terms "X" and seed length (SL) are used interchangeably with the term exposed length (EpL) which denotes the number of nucleotides available for target DNA to bind; the terms "Y" and protector length (PL) are used interchangeably to represent the length of the protector; and the terms "Z", "E", "E'" and EL are used interchangeably to correspond to the term extended length (ExL) which represents the number of nucleotides by which the target sequence is extended. An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence. Addition of gRNA mismatches to the distal end of the gRNA can demonstrate enhanced specificity. The introduction of unprotected distal mismatches in Y or extension of the gRNA with distal mismatches (Z) can demonstrate enhanced specificity. This concept as mentioned is tied to X, Y, and Z components used in protected gRNAs. The unprotected mismatch concept may be further generalized to the concepts of X, Y, and Z described for protected guide RNAs.

In certain embodiments, any of the nucleases, including the modified nucleases as described herein, may be used in the methods, compositions, and kits according to the invention. In particular embodiments, nuclease activity of an unmodified nuclease may be compared with nuclease activity of any of the modified nucleases as described herein, e.g. to compare for instance off-target or on-target effects. Alternatively, nuclease activity (or a modified activity as described herein) of different modified nucleases may be compared, e.g. to compare for instance off-target or on-target effects.

His tag. Similarly, CD5L monomer and dimer were generated by cloning CD5L with His tag at C-terminus into a mammalian expression vector. The plasmids are expressed in mammalian cell line and secreted CD5L:p40, CD5L (monomer and dimer) were purified and confirmed by gel electrophoresis and HPLC.

```
CD5L sequence cloned:
   1    (maplfnlmla ilsifvgscf s)*esptkvqlv ggahrcegrv evehngqwgt vcddgwdrrd 61    vavvcrelnc gaviqtprga syqppaseqr vliqgvdcng tedtlaqcel nydvfdcshe 121    edagaqcenp dsdllfiped vrlvdgpghc qgrvevlhqs qwstvckagw nlqvskvvcr 181    qlgcgrallt ygscnkstqg kgpiwmgkms csgqeanlrs cllsrlennc thgedtwmec 241    edpfelklvg gdtpcsgrle vlhkgswgsv cddnwgeked qvvckqlgcg kslhpspktr 301    kiygpgagri wlddvncsgk eqslefcrhr lwgyhdcthk edvevictdf dv

*the signaling peptide was not included to better guide protein secretion in
the expression system p40/il12b sequence cloned
   1    mcpqkltisw faivllvspl mamwelekdv yvvevdwtpd apgetvnltc dtpeedditw 61    tsdqrhgvig sgktltitvk efldagqytc hkggetlshs hlllhkkeng iwsteilknf 121    knktflkcea pnysgrftcs wlvqrnmdlk fnikssssp dsravtcgma slsaekvtld 181    qrdyekysvs cqedvtcpta eetlpielal earqqnkyen ystsffirdi ikpdppknlq 241    mkplknsqve vsweypdsws tphsyfslkf fvriqrkkek mketeegcnq kgaflvekts 301    tevqckggnv cvqaqdryyn sscskwacvp crvrs
```

Also provided herein are compositions for use in carrying out the methods of the invention. More particularly, non-naturally occurring or engineered compositions are provided which comprise one or more of the elements required to ensure genomic perturbation. In particular embodiments, the compositions comprise one or more of the (modified) DNA binding protein, and/or a guide RNA. In particular embodiments, the composition comprises a vector. In further particular embodiments, the vector comprises a polynucleotide encoding a gRNA. In particular embodiments, the vector comprises two or more guide RNAs. Said two or more guide RNAs may target a different target (so as to ensure multiplex targeting) or the same target, in which case the different guide RNAs will target different sequences within the same target sequence. Where provided in a vector the different guide RNAs may be under common control of the same promotor, or may be each be under control of the same or different promoters.

Recombinant protein CD5L monomer and homodimer was purified from the supernatant of 293E cells transfected with a CD5L expression vector. Recombinant mCD5L:p40 was recovered from the supernatant of 293E cells transfected with the CD5L:p40 expression vector. After harvesting transfected 293E cells by centrifugation, the protein was affinity purified from the supernatant using Ni Sepharose 6 Fast Flow resin (GE Healthcare). After binding the protein to resin, the resin was washed with 20 mM Tris, 0.3M NaCl, pH 8.0 and the protein eluted using 20 mM Tris, 0.3M NaCl, 0.4M Imidazole, pH 8.0. The protein was further polished by a Superdex S200 sizing exclusion column (GE Healthcare) in buffer 10 mM NaHPO4, 0.15M NaCl, pH 7.2. The S200 profile of the mCD5L:p40 showed a single peak. The S200 profile of the mCD5L transfection showed two overlapping peaks, corresponding to the homo-dimer fraction first and then monomer fraction.

Example 1. Soluble CD5L and CD5L/p40 can Regulate T Cell Function and have Overlapping as Well as Distinct Roles CD5L can be secreted by macrophages (Miyazaki et al., 1999) and given its T-cell intrinsic role, we tested the hypothesis that soluble CD5L can regulate T cell function directly in vitro. Although Abdi et al. reported that CD5L can form a heterodimer with p40, no specific function was attributed to this potential cytokine (Abdi et al., 2014). We hypothesized that both soluble CD5L and CD5L:p40 heterodimer can regulate T cell function directly.

EXAMPLES

The invention is further described in the following examples, which do not limit the scope of the invention described in the claims.
Materials and Methods
The CD5L monomer, CD5L dimer and CD5L:p40 heterodimer generations were out-sourced to Biolegend under CDA. Briefly, to generate the CD5L:p40 heterodimer, Cd5l and Il12b (p40) were cloned into mammalian expression vector through a linker: P40-linker 2-3 (SGGG)-CD5L with To this end, we used recombinant CD5L monomer either alone or with recombinant p40 monomer and analyzed the transcriptome of activated CD4 T cells, either WT or CD5L$^{-/-}$, co-incubated with these soluble factors. First, we analyzed the effect of soluble CD5L alone. We reasoned that if soluble CD5L (sCD5L) functions similarly to that of T-cell intrinsic CD5L, the addition of sCD5L can reverse the effects of CD5L deficiency on T cells. Indeed, we showed that sCD5L reversed the expression profile of majority of genes differentially regulated by any of the conditions tested (FIG. 1A). To exclude inference from T cell endogenous CD5L expression, we focused on the impact of sCD5L on Cd5l$^{-/-}$ T cells. Of interest, sCD5L also regulated expression profile of genes that were not changed comparing WT and Cd5l$^{-/-}$ T cells or opposed the T-cell intrinsic function of CD5L (FIG. 1A), suggesting potential novel role of the soluble CD5L.

Next, we performed pathway analysis of genes regulated by soluble CD5L and found sCD5L regulated gene profile contains both a regulatory and an inflammatory component. First, we observed that in sCD5L treated T cells there was a significant enrichment of signature genes of regulatory T cells from four different datasets using MSigDB (Table 1). Interestingly the key transcription factor of Treg, Foxp3, was downregulated by sCD5L (Table 1). This is consistent with sCD5L also promoting factors (such as Il4, Il9) that have been implicated in destabilizing Foxp3 expression antagonizing retinoic acid (Table 1 and (Hill et al., 2008)). These data suggest that soluble CD5L may promote a regulatory program but independent of Foxp3 expression and may be an inducer of Th9 response. In addition to the regulatory component, we found that sCD5L regulated genes are significantly enriched for genes induced by IL-6/IL-1B but downregulated by IL-6/IL-1B/IL-23, suggesting soluble CD5L may antagonize IL-23 function (Table 1).

TABLE 1

Pathway analysis of soluble CD5L-dependent regulation of T cells.

| Enriched pathways | genes |
|---|---|
| A. Reversal/Novel (soluble) UP | |
| Treg (4 independent datasets) (FDR q-value 1.63 e-8) | (PDL2, LIF, SOCS2, IKZF4, ICOS, PROCR, NFIL3, CD200, TGM2, PRNP, CD70, XBP1, ATF4, LAD1, KLF9, CD83, Runx2, IRF8, IFNg etc) |
| RA treated memory CD4 (FDR q-value 9.58 e-10) | IER3, IL4, RAB33A, FZD7, NFIL3, SLAMF7, TNFSF9, FAIM3, IL9, Foxp3 |
| IL-6/IL-1B | IL-22, GJA1, EGR2, IL1RN, CD200, ITGA3 |
| IL-4 | IL-4 |
| B. Reversal/Novel (soluble) DOWN | |
| -IL-6/IL-1B/IL-23 | GMFG, MGLL, FRMD4B, MINA |

Soluble CD5L induces both a regulatory and proinflammatory program including Il9 response. Differentially regulated genes were investigated using Msigdb and selected significant enrichment are listed in A and B showing those upregulated and downregulated by soluble CD5L respectively. Red and Green indicates directionality: Red pathway means soluble CD5L treatment goes with, green pathway means goes against such pathways (In the above tables, the "Treg," "IL-6/IL-1B," and "IL-4" rows are red pathways, and the "RA treated memory CD4" and "IL-6/IL-1B/IL-23" rows are green pathways).

Figure 2:
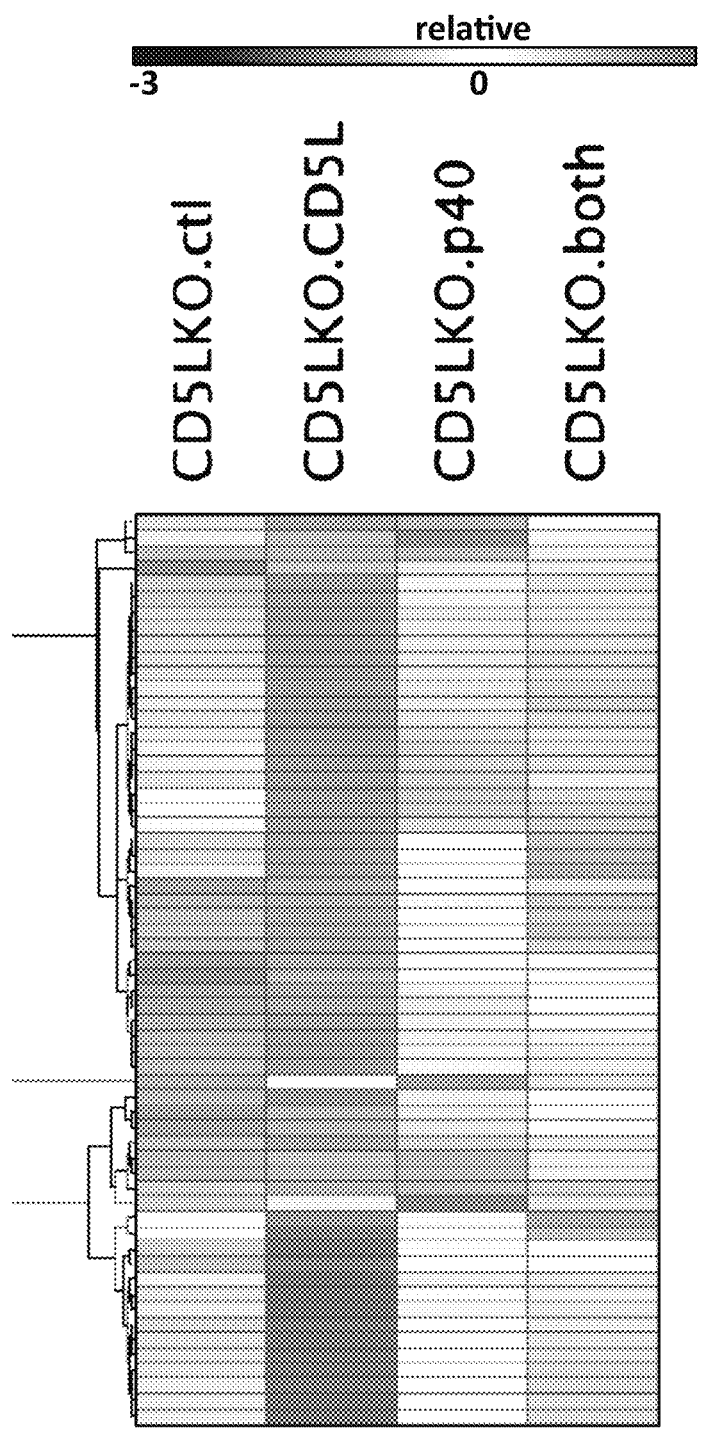
FIG. 2. Soluble CD5L (CD5Lm) and CD5L/p40 premix can have unique functions on T cells. Similar to FIG. 1. Th0 cells were incubated with soluble CD5L, CD5L/p40 mixture (premixed for 4 hours), p40 or control PBS.
Figure 2:
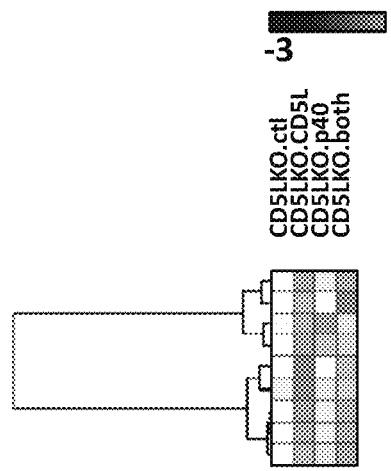
Figure 2:
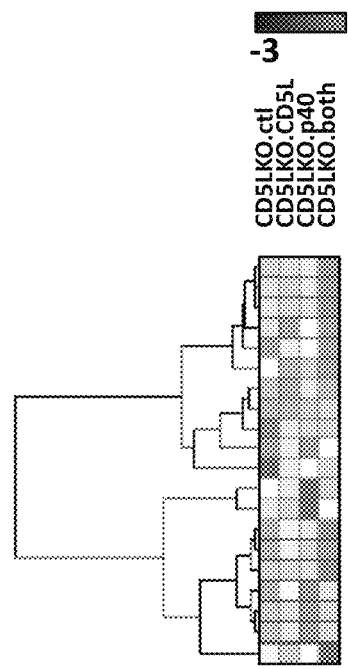
Figure 2:
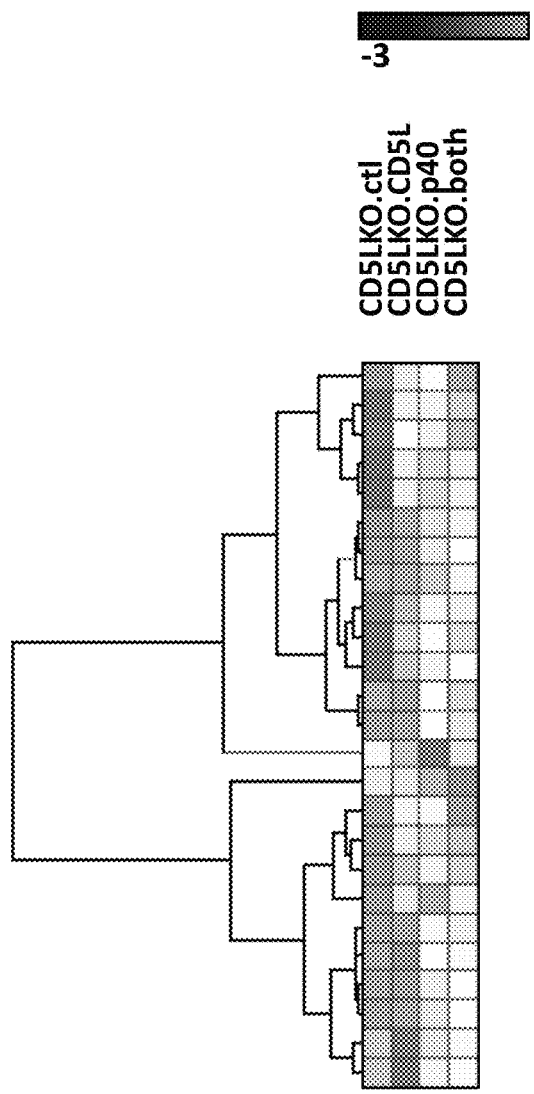

Finally, we compared the effect of sCD5L to that of sCD5L:p40 and found these two cytokines to regulate the expression profile of both similar and distinct set of genes (FIG. 2). Thus, these data collectively suggest sCD5L and sCD5L:p40 are novel cytokines that can regulate T cell function.

Example 2. T Cell Regulation by sCD5L and CD5L:p40 Depends on IL-23R Signaling

Figure 3A:
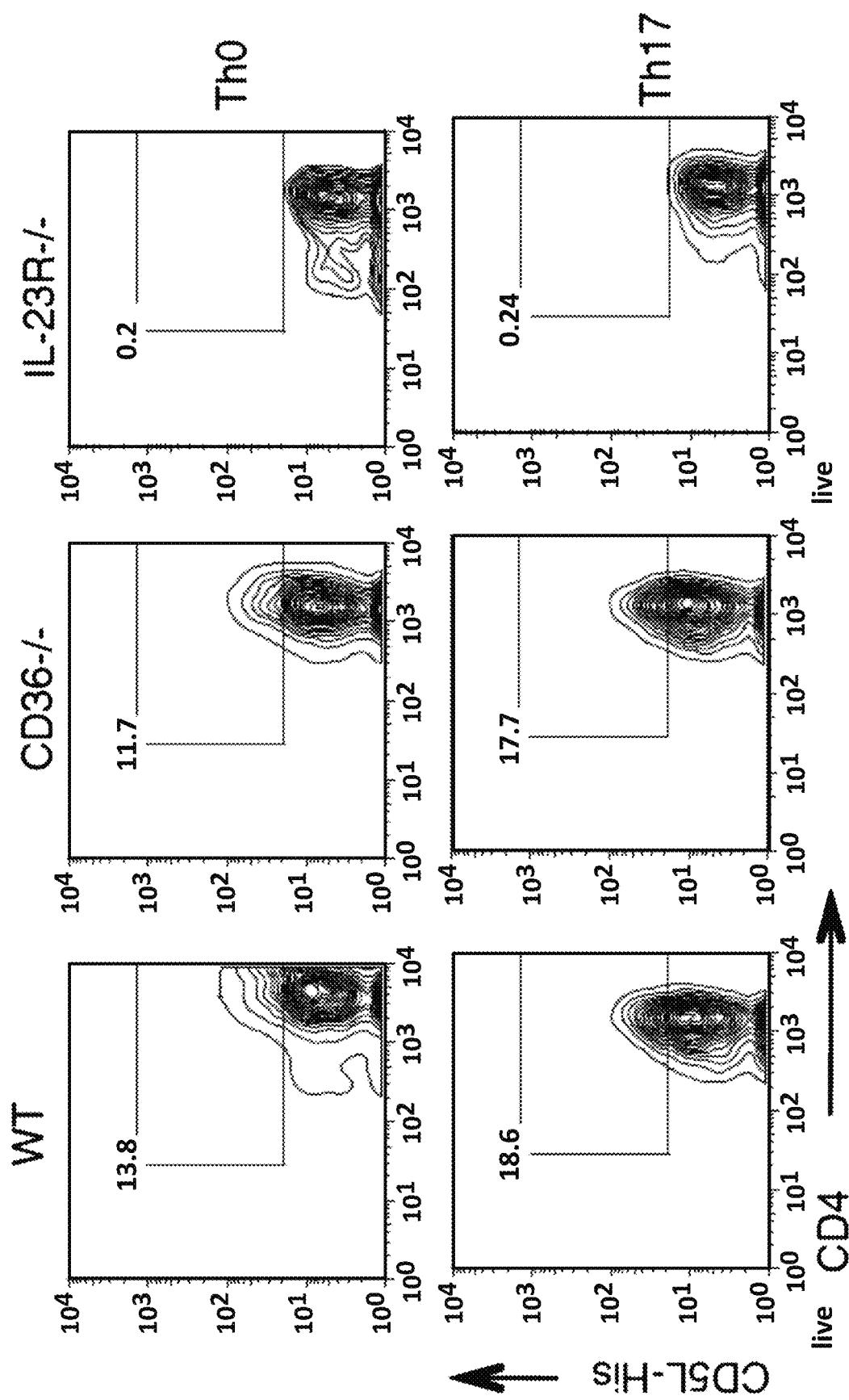
FIGS. 3A-C. The impact of soluble CD5L or CD5L/p40 can be dependent on IL-23R expression Similar to FIG. 1. CD5L−/− or CD5L−/− IL-23R−/− Th0 cells were incubated with soluble CD5L, CD5L/p40 mixture (premixed for 4 hours), p40 or control PBS.

As sCD5L and CD5L:p40 can regulate gene expression in T cells, we investigated what receptor(s) might be responsible for their function. CD5L was reported to interact with CD36, a scavenger receptor, and thus can be internalized into adipocytes (Kurokawa et al., 2010). We investigated whether CD36 is required for signaling of sCD5L in T cells. We showed that His-tagged sCD5L can stain WT and CD36$^{-/-}$ T cells equally well even at lower concentrations (FIG. 3A and data not shown). While this data is consistent with lower expression of CD36 on T cells compared to macrophage (ImmGen database), it also raises the question whether the sCD5L can bind to a different receptor on T cells.

CD5L can form a heterodimer with p40 and p40 can bind to either p19 or p35. We hypothesized that if sCD5L binds to a surface receptor it may be co-regulated/dependent on receptors for the other two cytokines: that is IL-12RB1, IL-12RB2 or IL-23R. We tested whether sCD5L can stain Il12rb1$^{-/-}$, Il12rb2$^{-/-}$ or Il23r$^{-/-}$ T cells as compared to WT (FIG. 3A and data not shown). Interestingly, the binding of sCD5L is abolished on Il23r$^{-/-}$ T cells and partially reduced on Il12rb1$^{-/-}$, Il12rb2$^{-/-}$ T cells. These findings suggest that CD5L may interact with a receptor that depends on IL-23R signaling.

Figure 3B:
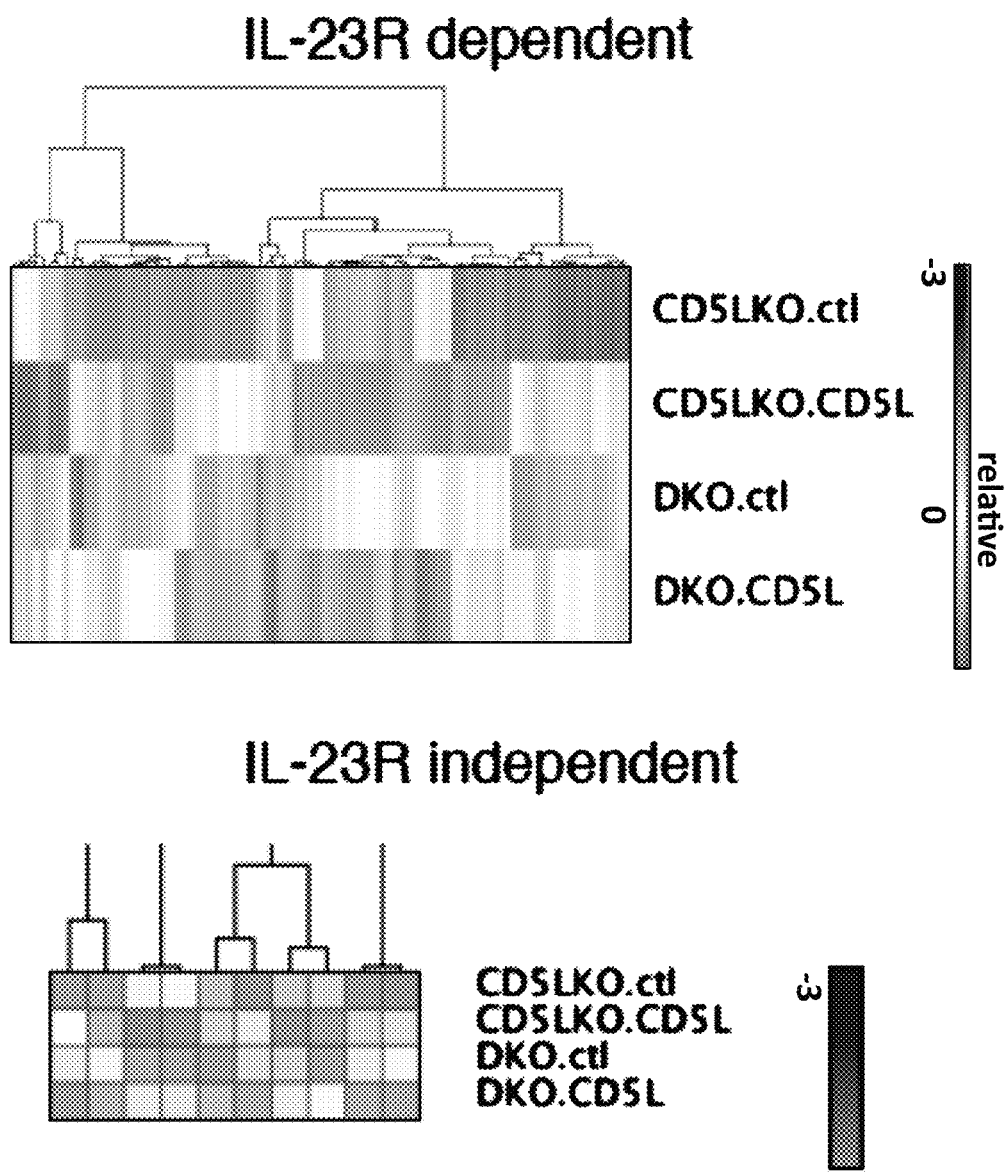
Figure 3C:
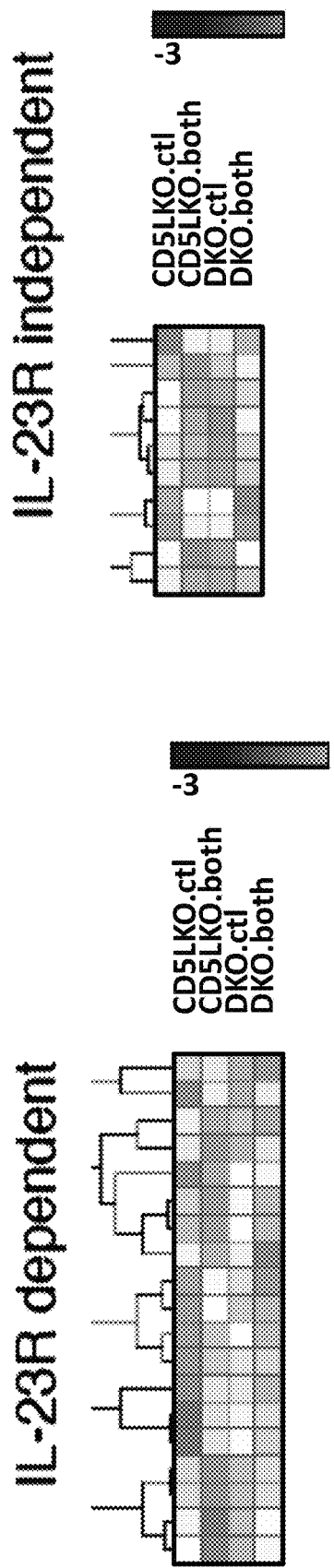

Next, we asked the question whether the function of sCD5L is also affected by the absence of IL-23R on T cells. To this end, we crossed Cd5l$^{-/-}$ mice with Il23r$^{-/-}$ mice and found that in the absence of IL-23R, the expression of 89% of genes (84 out of 94 based on nanostring set) regulated by sCD5L were no longer affected (FIG. 3B). The effect of CD5L:p40 heterodimer could also be partially dependent on IL-23R expression (FIG. 3C). Thus sCD5L and CD5L:p40 may interact with different receptors on T cells.

Example 3. CD5L Regulates not Only T Cells but Also Restrains Proinflammatory Function of Innate Lymphoid Cells (ILC) and is Expressed by ILC in Naïve Mouse The discovery that soluble CD5L can regulate T cell function directly and that its impact may dependent on IL-23R expression prompted us to study whether CD5L can regulate other cells that may also express IL-23R. To this end, we investigated the impact of CD5L on two such populations that express IL-23R: innate lymphoid cells (ILC) and dendritic cells (DC).

Figure 4A:
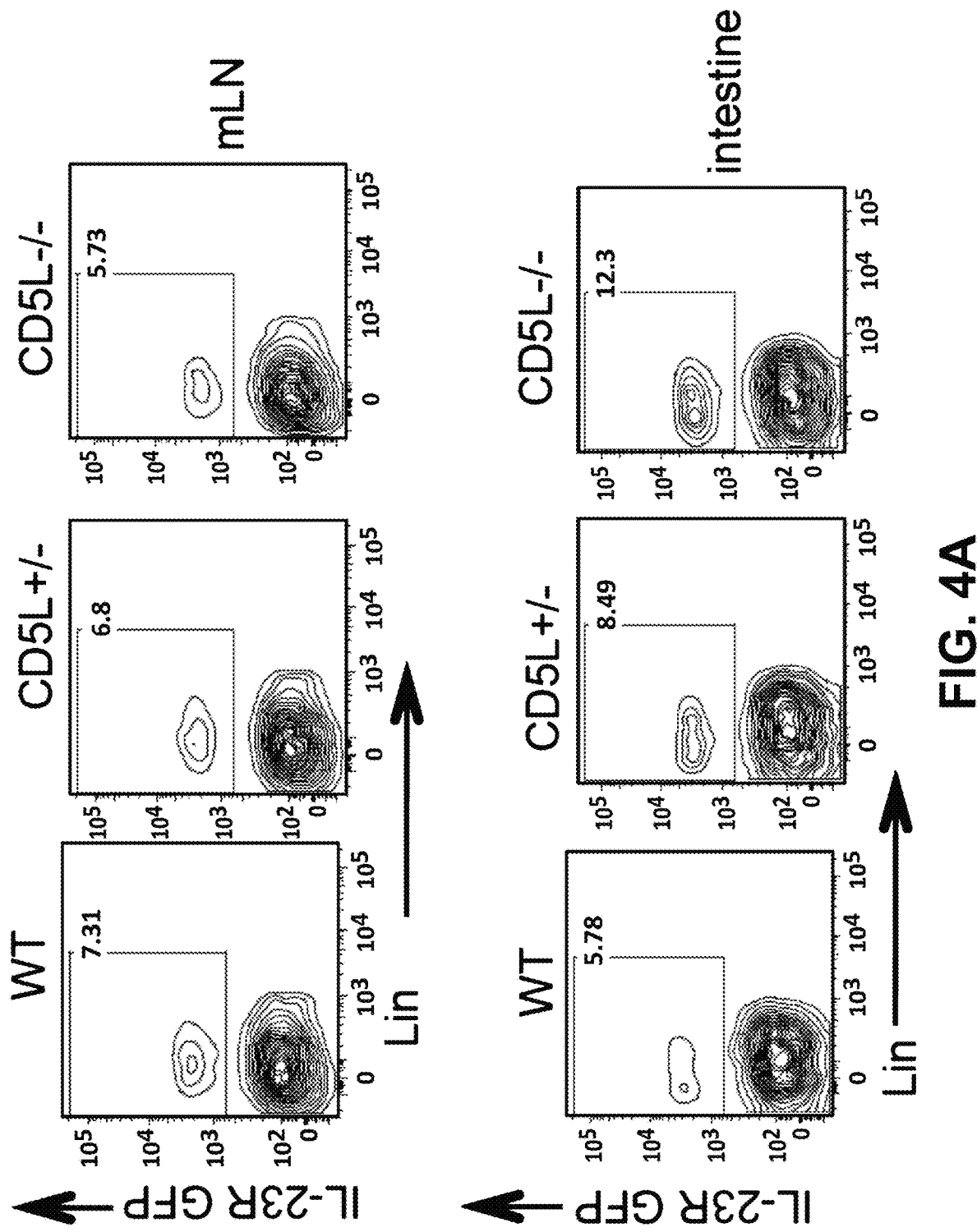
FIGS. 4A-G. CD5L regulates ILC function at steady state and during inflammation.
Figure 4B:
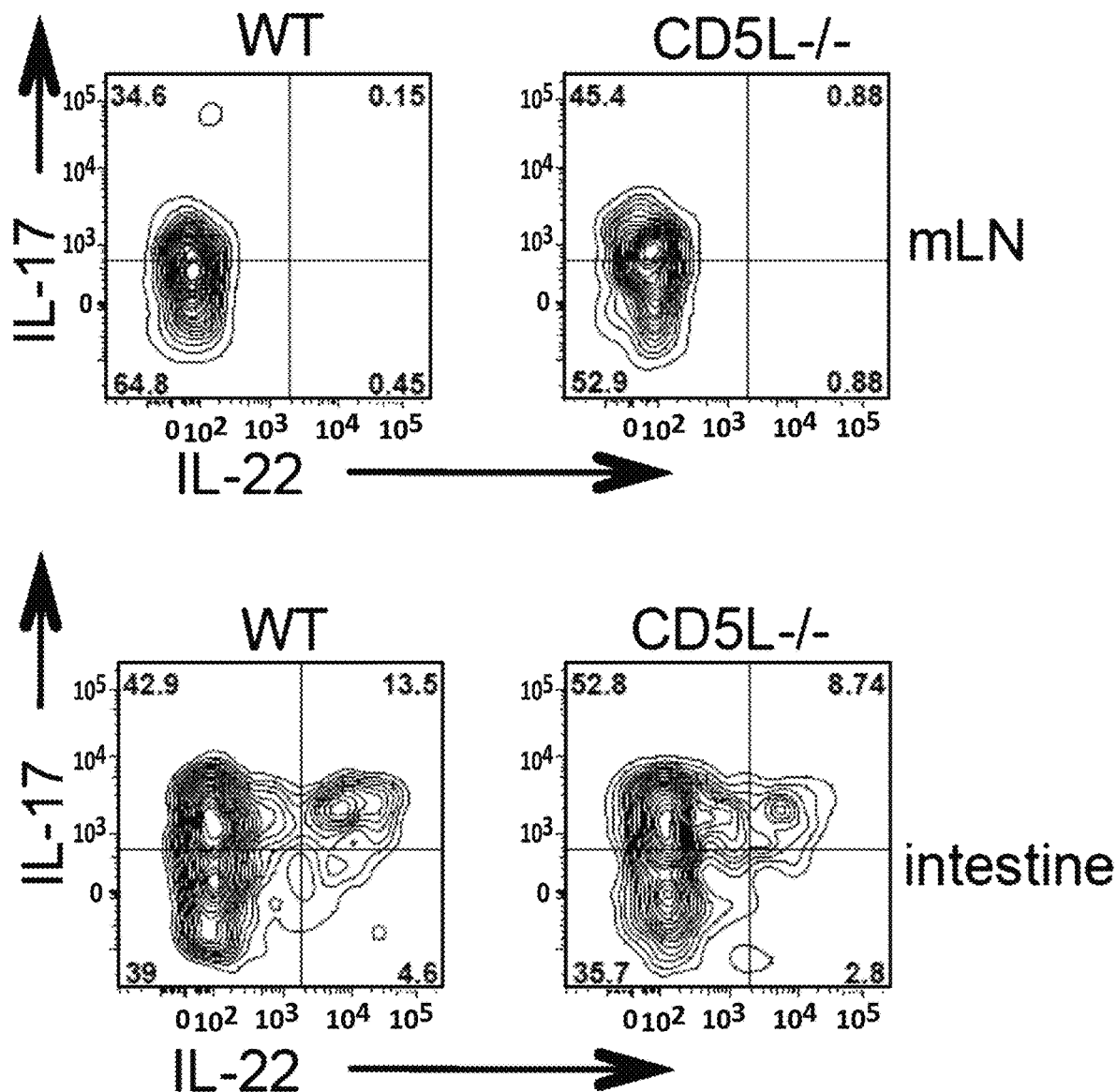
Figure 4C:
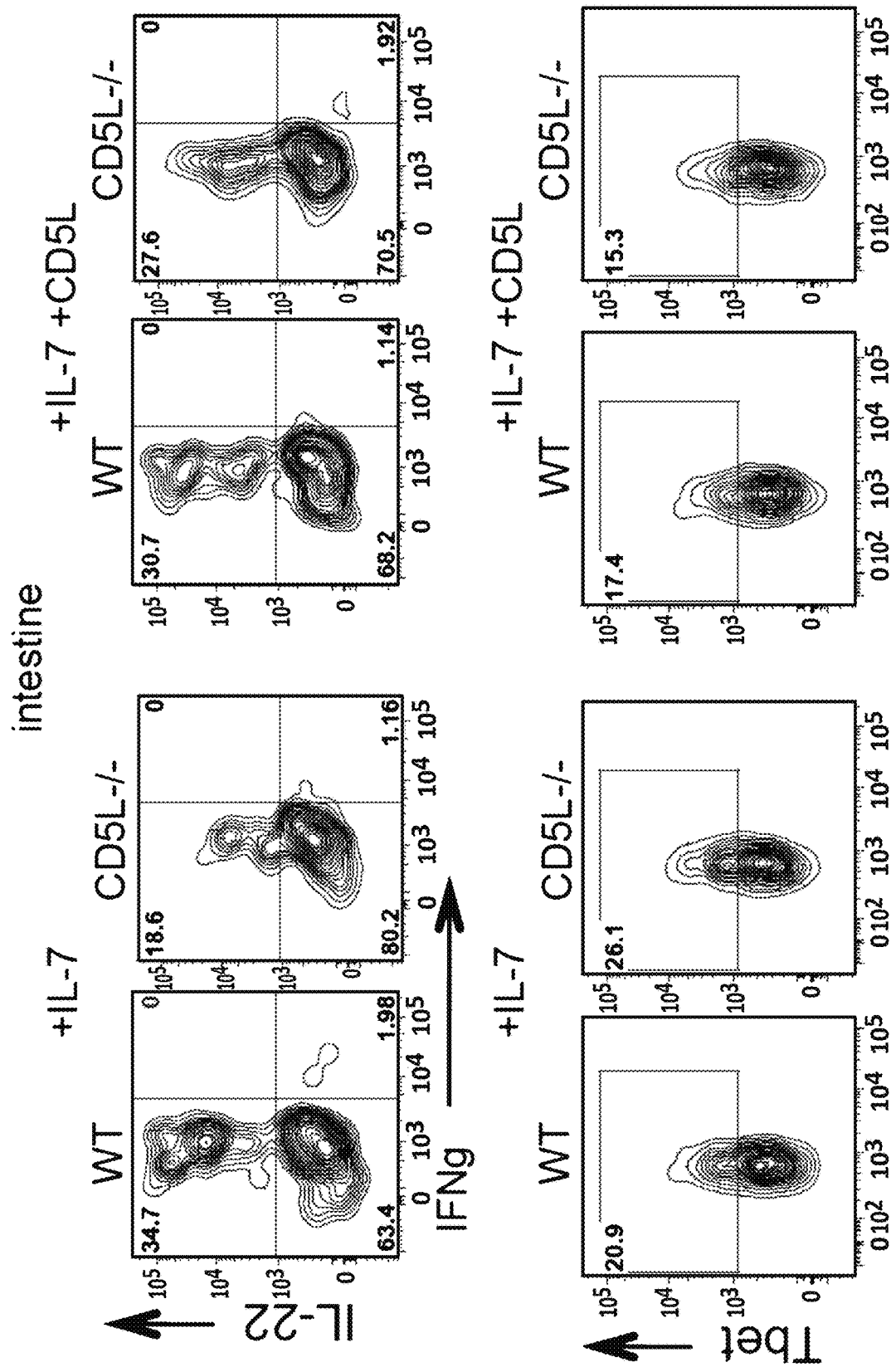
Figure 4D:
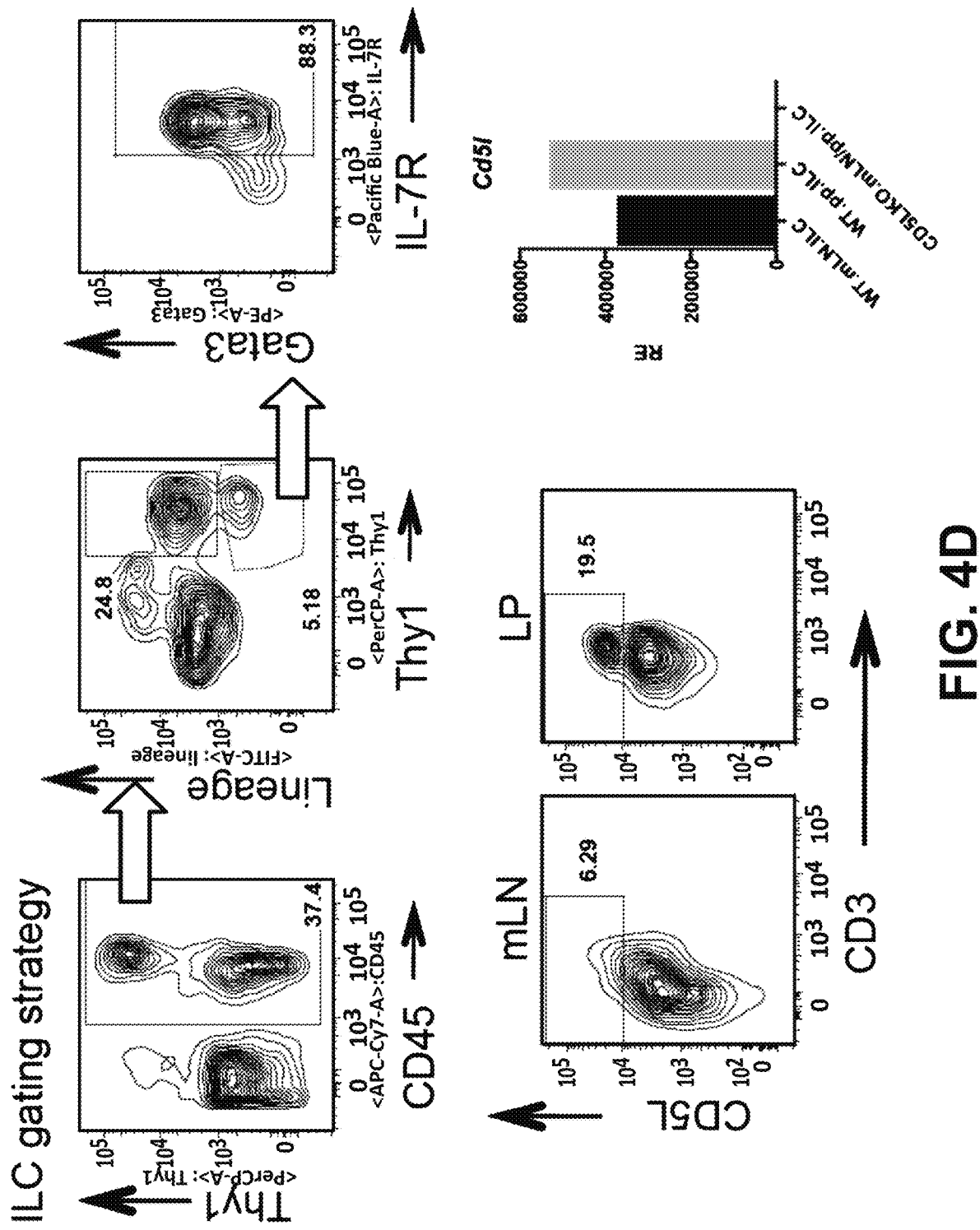

First, we analyzed the percent and function of ILC in naïve 6-month old WT versus Cd5l$^{-/-}$ mice. We observed that IL-23R expression on ILC from Lamina propria is significantly increased in the absence of CD5L (FIG. 4A). This is accompanied with higher proportion of ILCs producing IL-17 and Tbet, but lower percent of IL-22 producers (FIG. 4BC). We further demonstrated that the reduced IL-22 expression and increased Tbet expression by ILC can be reverted by soluble CD5L ex vivo (FIG. 4C). These data suggest that CD5L can regulate ILC function at steady state. Of interest, we observed that ILC isolated from both mLN and Lamina propria from naïve mice can express CD5L (FIG. 4D).

Figure 4E:
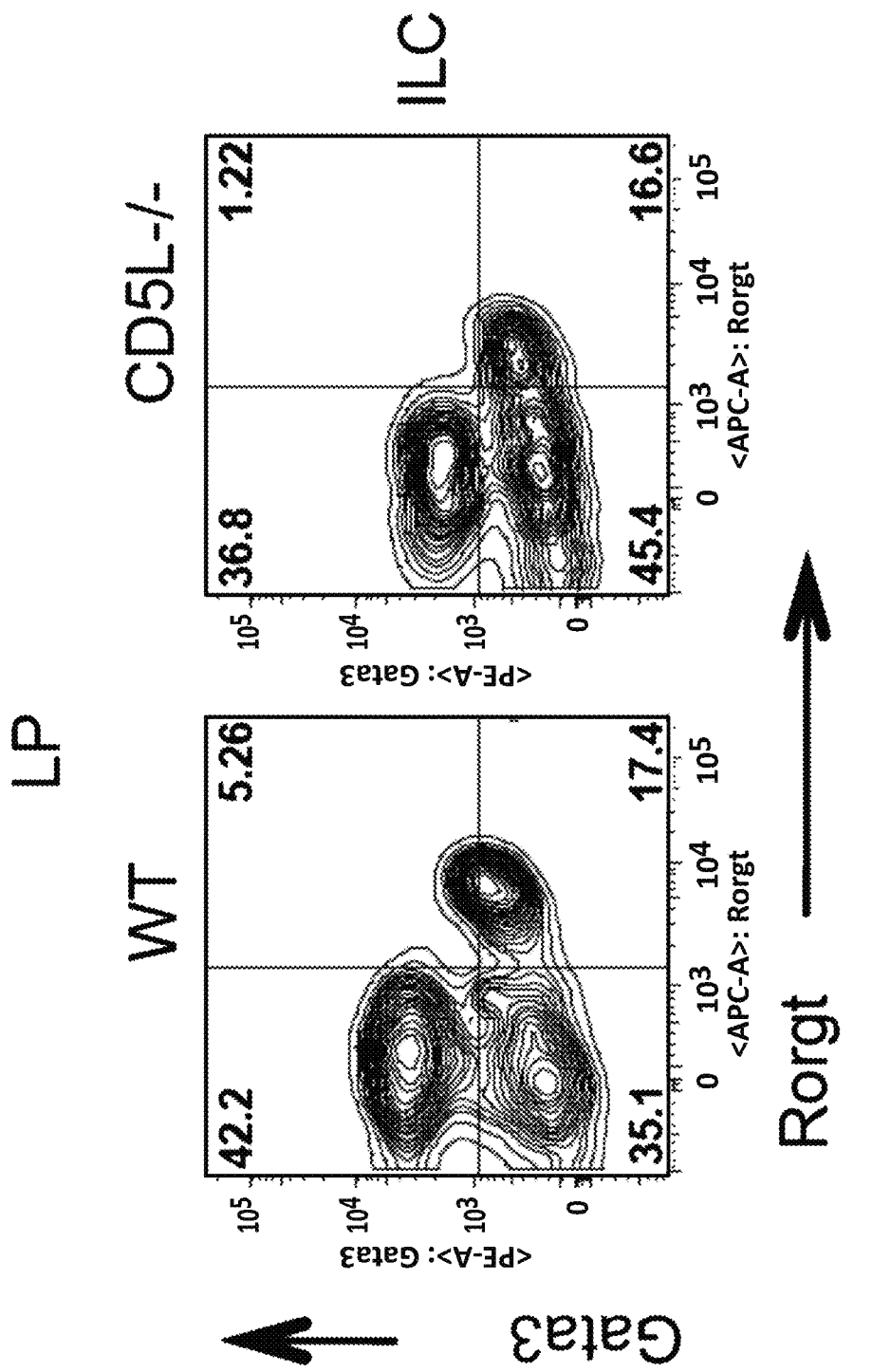
Figure 4F:
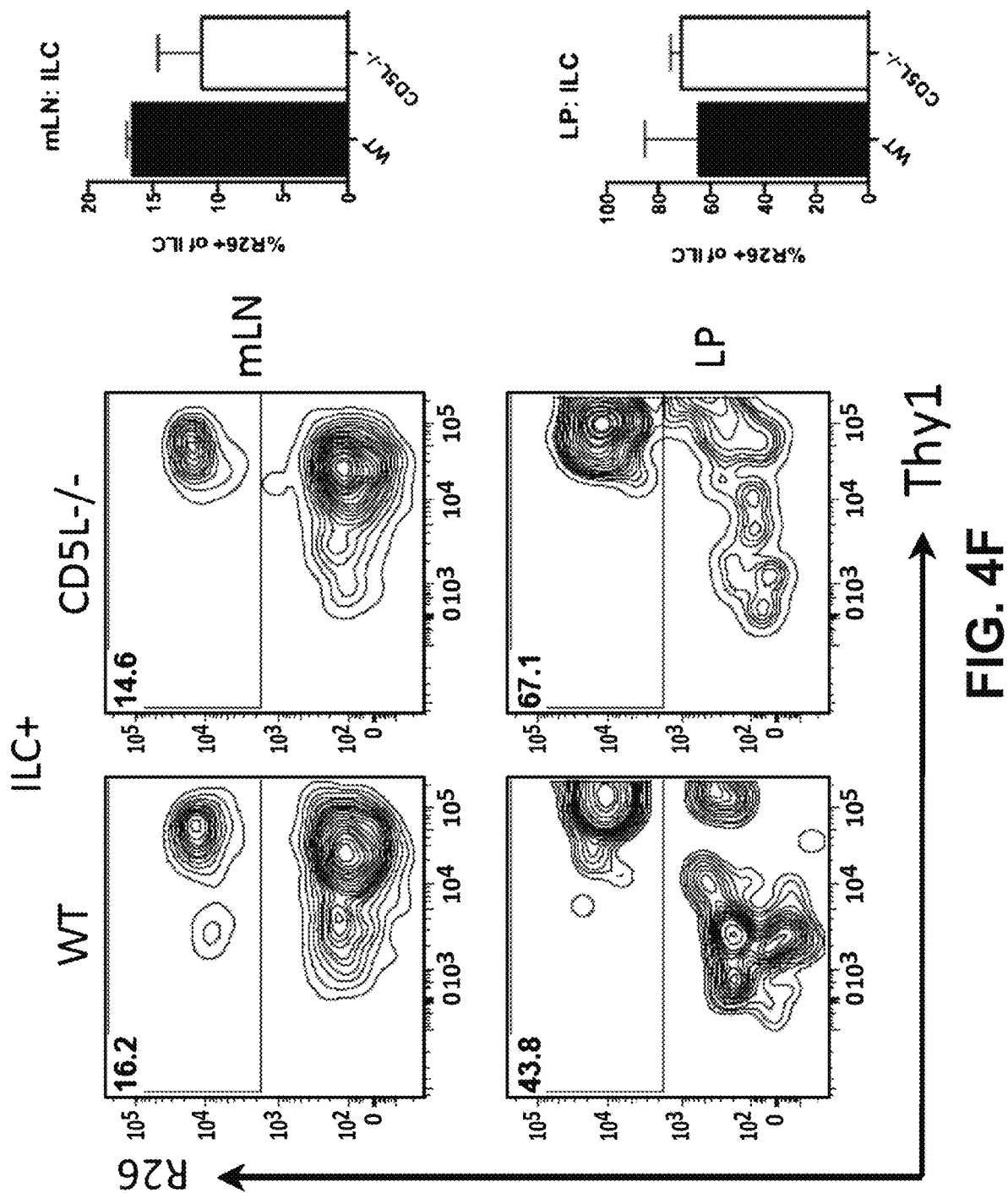
Figure 4G:
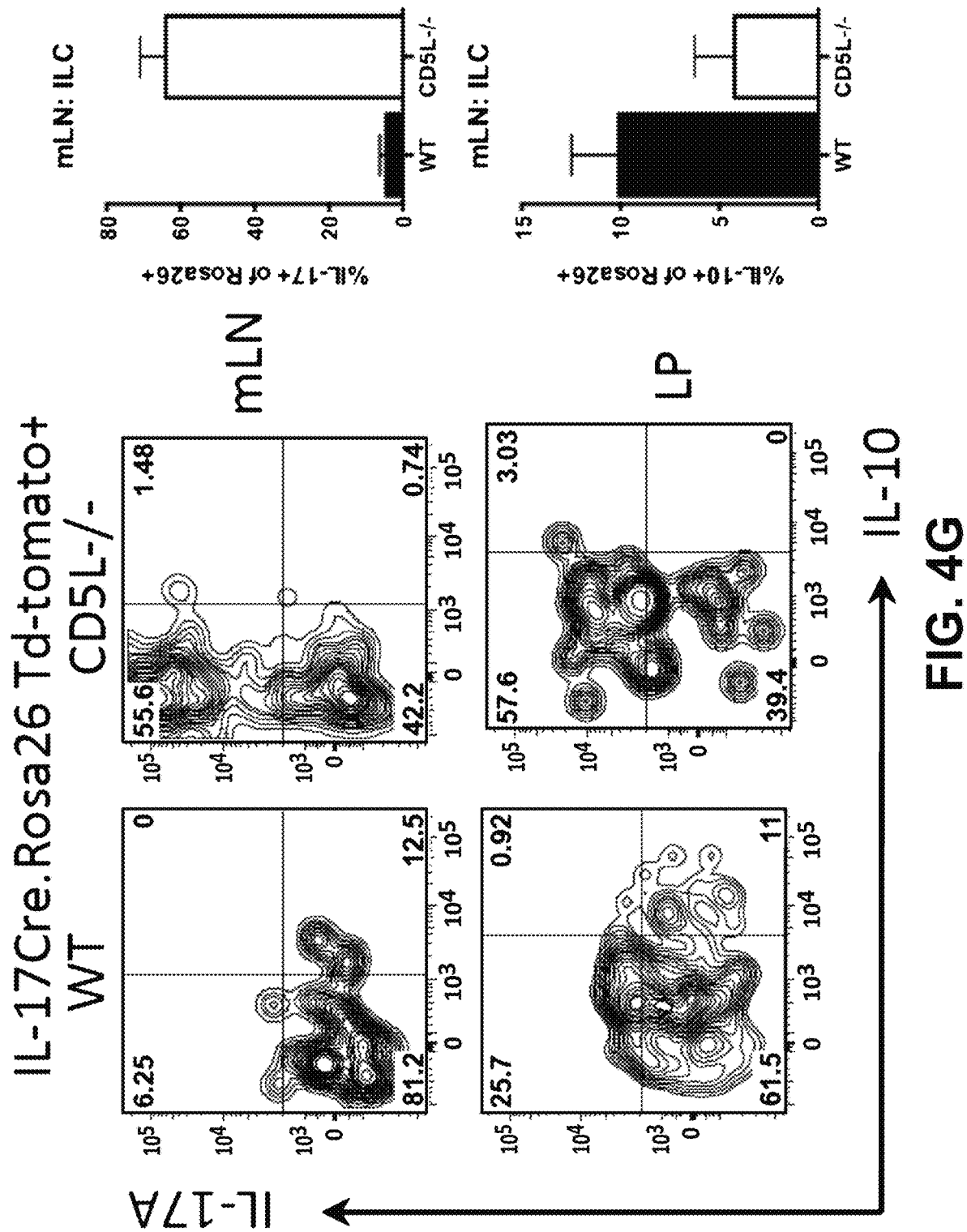

Next, we asked whether CD5L influence ILC during inflammation. As CD5L regulates IL-17 and IL-17 production is associated with ILC3, we crossed Cd5l$^{-/-}$ mice with fate mapping reporter mice Il17a$^{Cre}$Rosa26$^{Td\text{-}tomato}$ to better track ILC3 that has ever transcribed sufficient IL-17 to turn on the Cre. Using the DSS-induced acute colitis model, we showed that there is similar percent of Rosa26$^+$ ILC comparing 8-wk old WT. Il17a$^{Cre}$Rosa26$^{Td\text{-}tomato}$ and Cd5l$^{-/-}$ Il17a$^{Cre}$Rosa26$^{Td\text{-}tomato}$ mice at day 11 since DSS treatment (FIG. 4F), suggesting CD5L does not influence the differentiation of ILCs initially. Consistently, the percent of ILC that expresses Rorgt is not significantly altered (FIG. 4E). In contrast to the Rosa26 expression, ILC from WT.Il17a$^{Cre}$Rosa26$^{Td\text{-}tomato}$ make little IL-17 and turned on IL-10 expression in striking contrast to those from Cd5l$^{-/-}$ Il17a$^{Cre}$Rosa26$^{Td\text{-}tomato}$ mice which continue to produce much higher expression of IL-17 and are IL-10 negative (FIG. 4G). Thus CD5L can restrain proinflammatory function of ILC during acute inflammation.

Example 4. CD5L:p40 Promotes Regulatory Programs in CD11c$^+$ Cells in an IL-23R but not CD36 Dependent Manner It has been reported that CD5L can induce autophagy in the human macrophage cell line, THP, limiting TNFa and IL-1B expression and promoting IL-10 expression (Sanjurjo et al., 2015). The authors propose CD36 is the major recipient of CD5L in these cells. As we discovered that sCD5L (and CD5L:p40 heterodimer) could regulate T cells through an IL-23R-dependent alternative receptor, we tested the hypothesis that CD5L and CD5L:p40 may regulate myeloid cells in an IL-23R dependent pathway.

Figure 5:
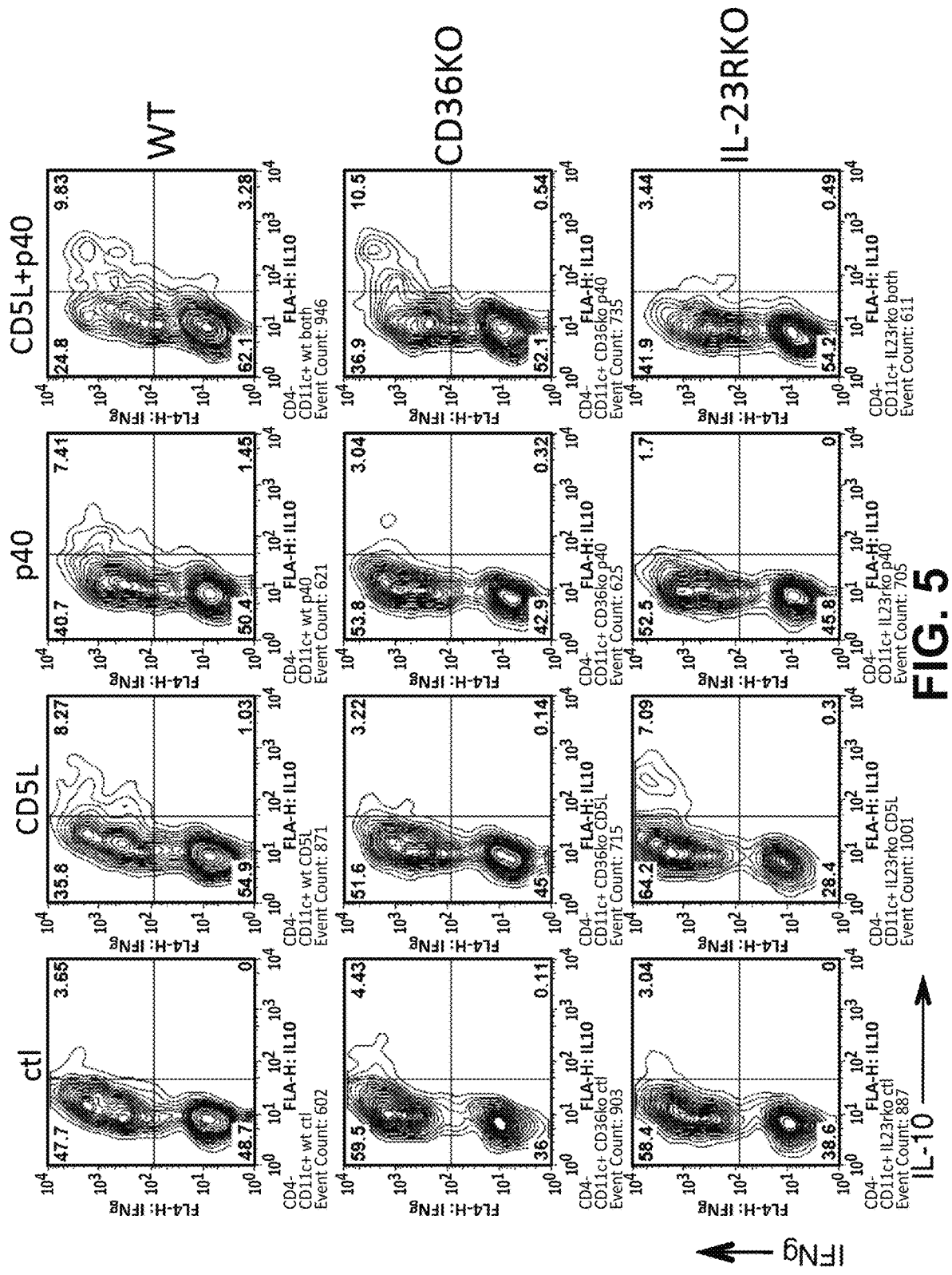
FIG. 5. CD5L and CD5L:p40 regulate CD11c$^+$ DC function. CD11c$^+$ cells were enriched and sorted from spleen of WT, CD36−/− and IL-23R−/− naïve mice. CD11c$^+$ cells were stimulated with 100 ng/ml LPS in the presence of either control, sCD5L, p40 or CD5L:p40 at 5 uM. Cells were harvested at 24 hours.

To test this hypothesis, we isolated WT, CD36$^{-/-}$ and IL-23R$^{-/-}$ CD11c$^+$ cells from spleen of naïve mice and stimulated the cells with LPS in the presence of sCD5L, p40 or CD5L:p40. We showed that sCD4L, p40 and CD5L:p40 can all induce IL-10 expression from CD11c' cells, however the effect of CD5L:p40 is dependent on IL-23R whereas the effect of sCD5L is dependent on CD36 (FIG. 5).

Example 5. CD5L Plays a Protective Role in Acute Colitis and Cancer

Figure 6A:
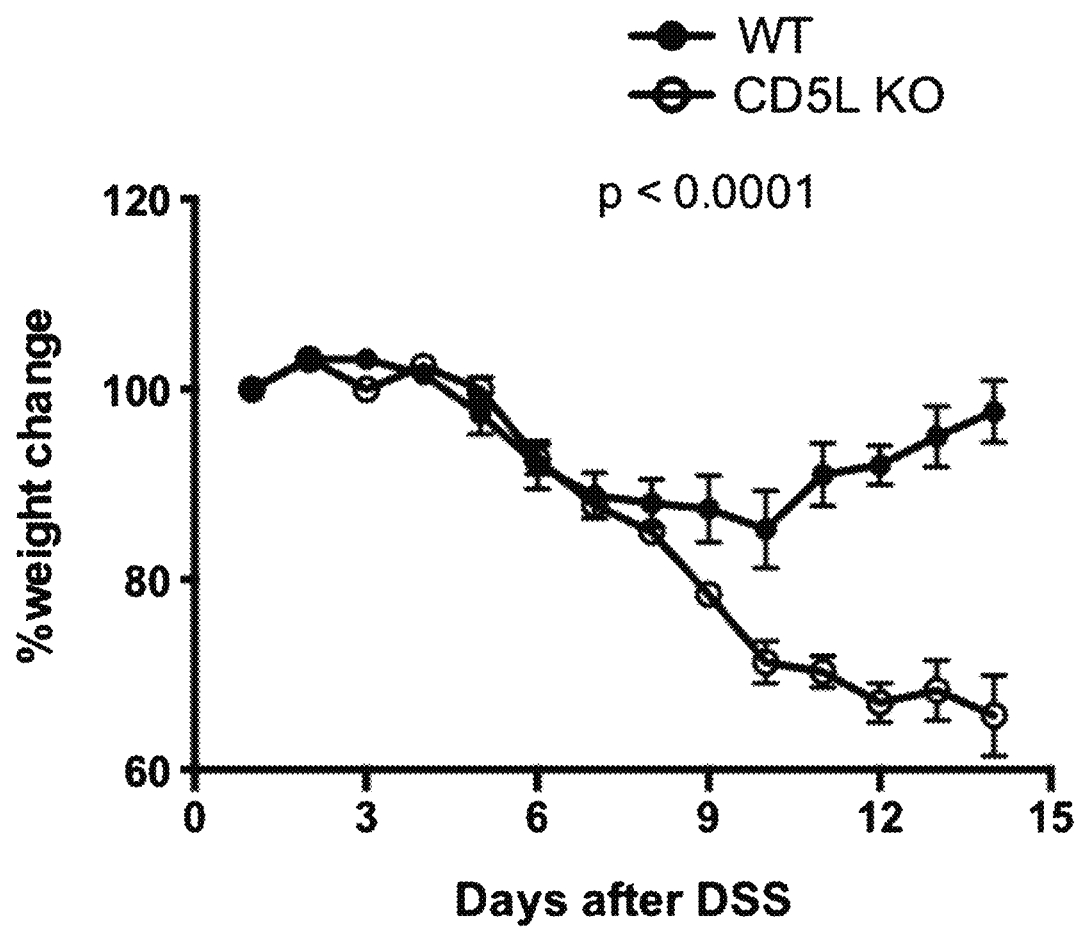
FIGS. 6A-D. CD5L$^{−/−}$ mice have more severe colitis in response to DSS-induced injury. 6-8 wk old WT or CD5L$^{−/−}$ mice were treated with 2.5% DSS in drinking water for 7 days followed by 7 days of regular water. Weight (FIG. 6A), colitis score (FIG. 6B) and colon length (FIG. 6C) and representative histology (FIG. 6D) were shown.
Figure 6C:
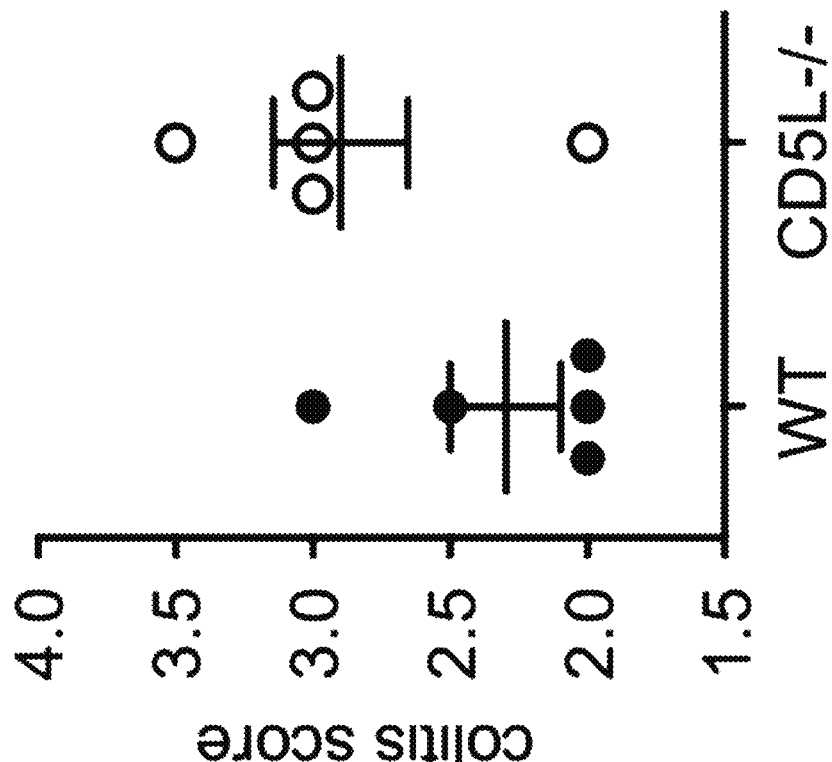
Figure 6B:
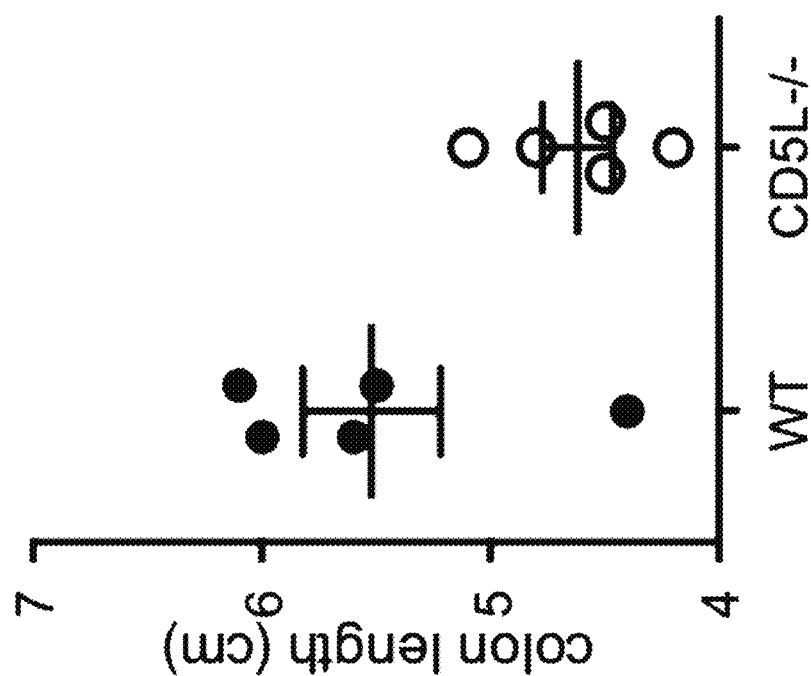
Figure 6D:
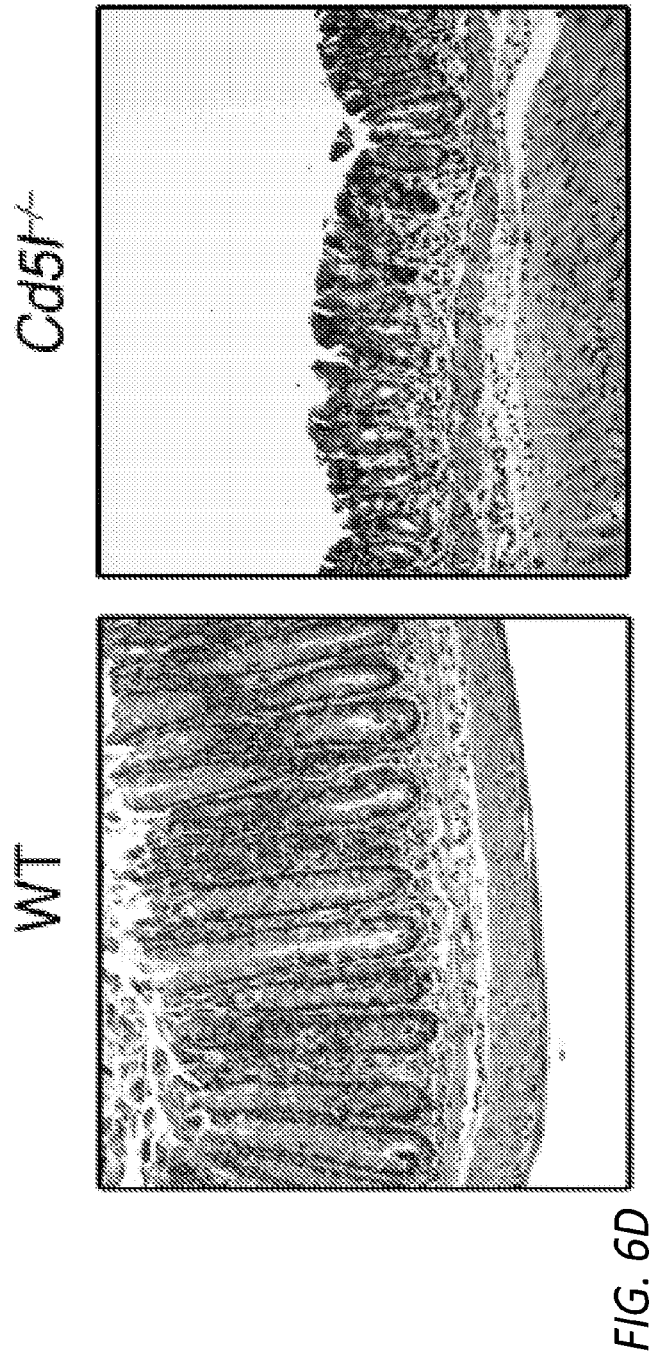

To test the function of CD5L and CD5L:p40 in vivo, we tested several disease models. CD5L$^{-/-}$ mice were treated with 2% DSS in drinking water for 6 days followed by normal water. Weight loss was reported as a percentage of initial weight in FIG. 6A. Colitis score and colon length were determined on day 14, and are shown in FIGS. 6B and C, respectively. Colon histology on day 14 is shown in FIG. 6D. This data demonstrates that CD5L influenced tumor progression in a B16 melanoma model.

Example 6. CD5L Ameliorates Autoimmune Diseases (Including MS), Acute Colitis, and Cancer To show that CD5L:p40 can ameliorate disease, we therapeutically treat mouse models of multiple sclerosis (EAE), colitis (e.g., DSS-induced injury model which is a mouse model for ulcerative colitis and T-cell dependent colitis model) or cancer (e.g., mice with inflammation-induced cancers, or human cancer xenografted onto mice) with recombinant CD5L:p40, or antibodies or antigen-binding fragments thereof or that bind to the heterodimers.

Figure 7A:
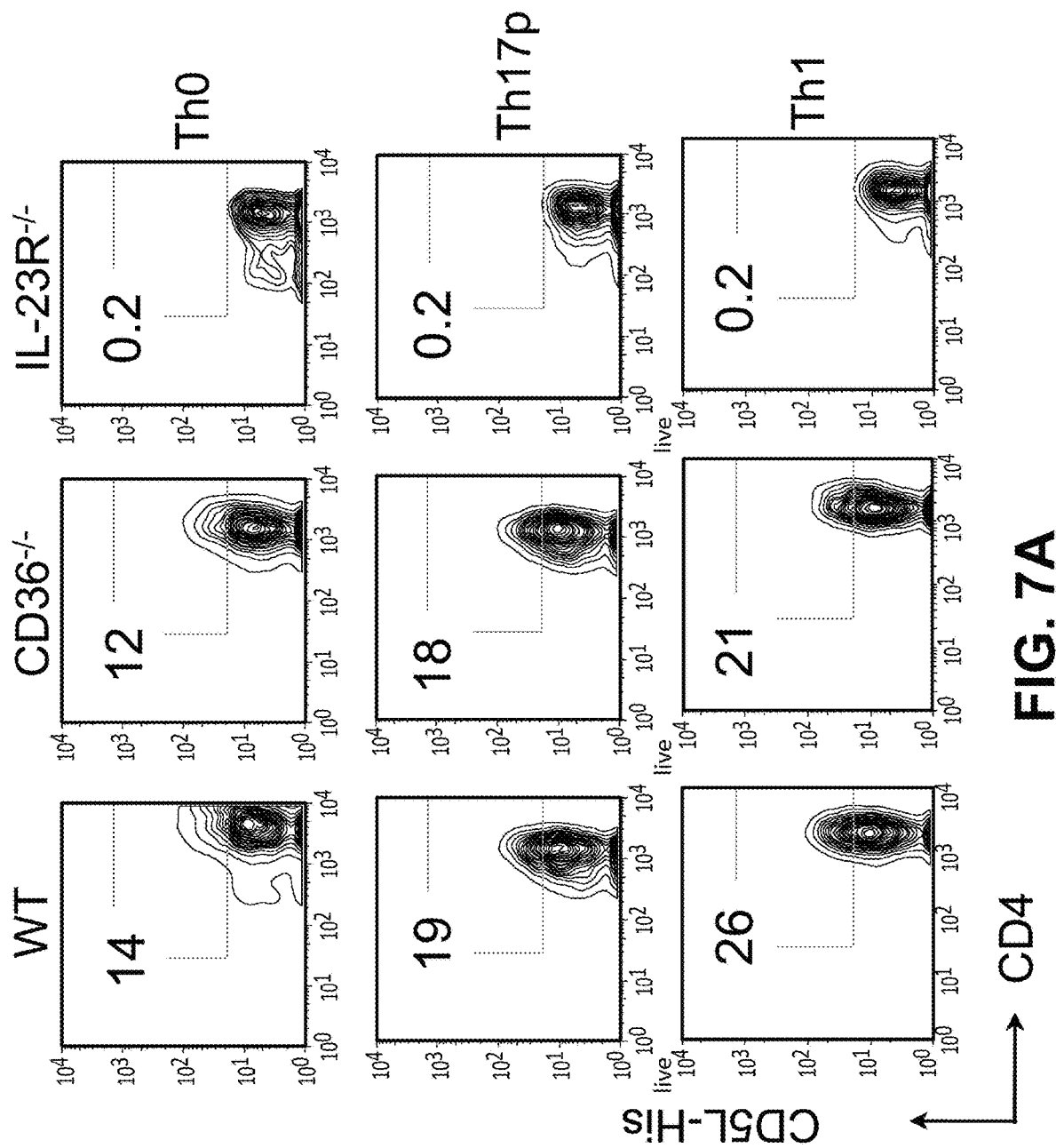
FIGS. 7A-C. Recombinant CD5L can bind to Th1 and Th17p (pathogenic Th17) cells and alleviate diseases severity of EAE and DSS induced colitis. Recombinant CD5L was generated with a His tag.

Example 7. Recombinant CD5L Binds to T Cells and Suppresses EAE and DSS-Induced Colitis Experiments were conducted to assess whether soluble CD5L could regulate effector T cells. In particular, soluble CD5L was directly evaluated using recombinant CD5L with a His-tag. Th0, Th1 (IL-12), and TH17p (IL-1b, IL-6, IL-23) cells were differentiated from naïve CD4 T cells in vitro for 4 days, and cells were harvested for staining with recombinant CD5L followed by anti-His APC antibodies and flow cytometry analysis. Flow cytometry data showed that CD5L can bind to both Th1 and pathogenic Th17 cells (Th17p) and to a lesser extent Th0 cells (FIG. 7A). The binding of CD5L on T cells was shown to not require CD36, but to be dependent on IL-23R (e.g., loss of IL-23R abrogated CD5L binding to T cells).

Figure 7B:
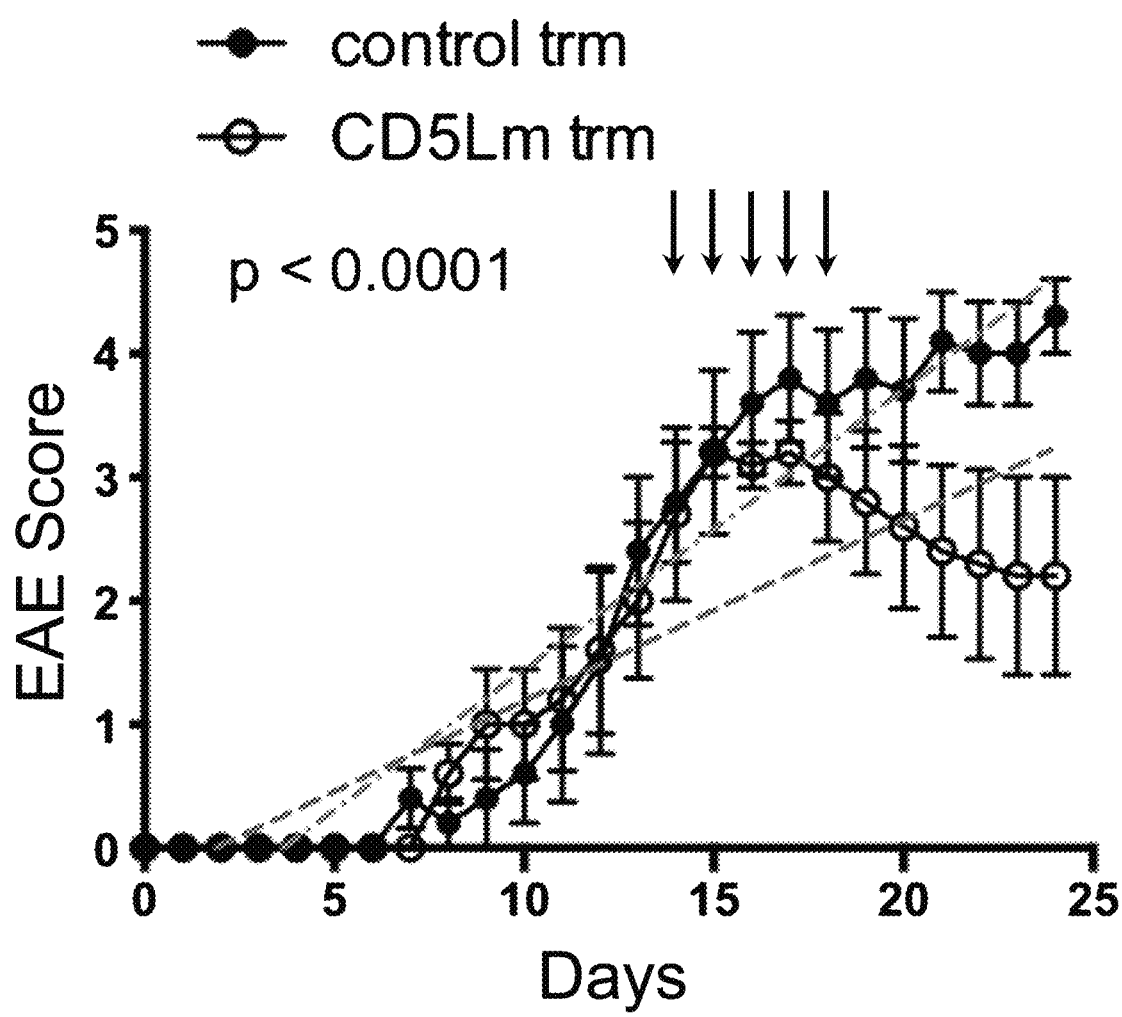

In vivo therapeutic experiments were conducted by immunizing wildtype mice with MOG/CFA following by PT injection to induce EAE. Mice at peak of disease (score=3 in FIG. 7B) were injected with either PBS (solid circles) or recombinant CD5L (empty circles) intraperitoneally daily for 5 consecutive days and mice were measured for disease progression. As shown in FIG. 7B, soluble CD5L was shown to have a therapeutic effect on EAE.

Figure 7C:
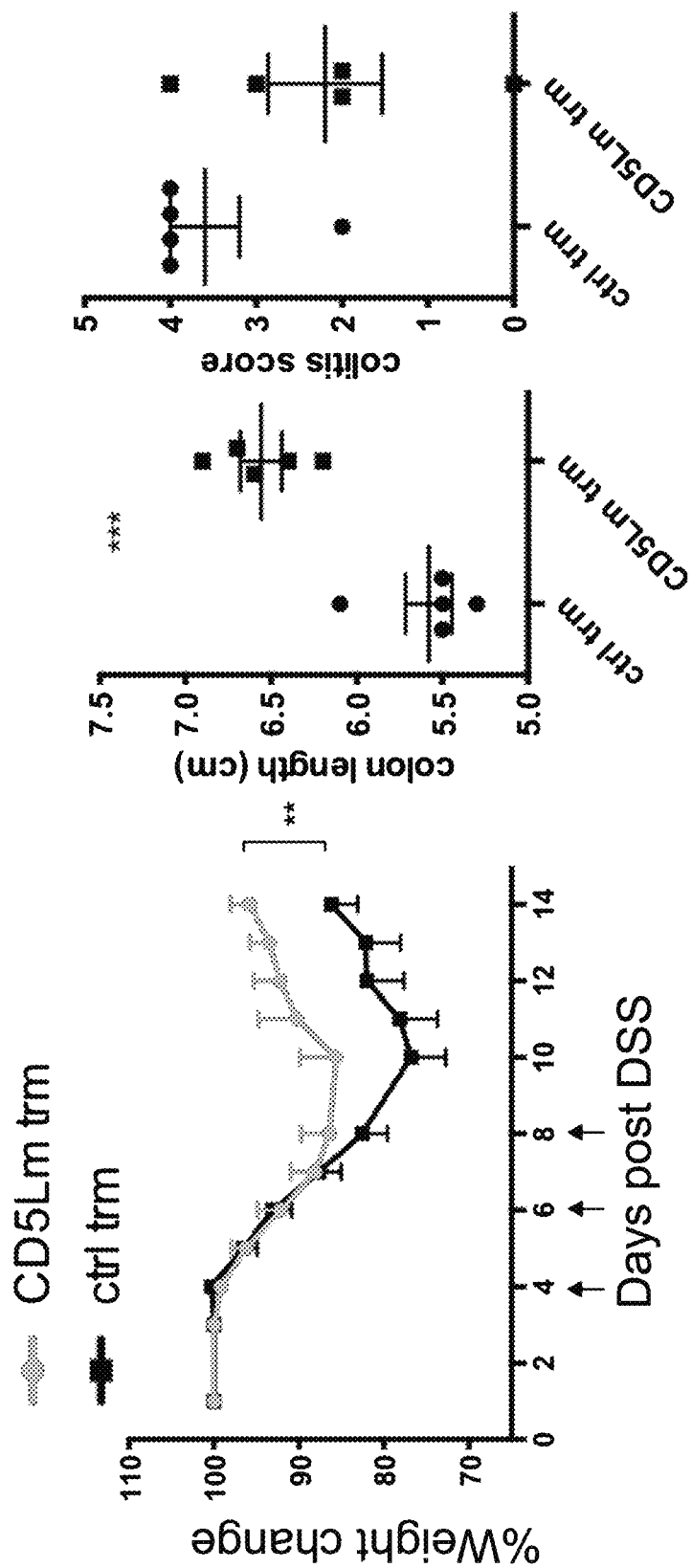

In a separate experiment, wildtype mice were induced with colitis via 2.5% DS in drinking water for 6 consecutive days, followed by normal water for 8 days. Mice were given either a control (PBS) or recombinant CD5L (CD5Lm) intraperitoneally on day 4, 6, and 8. Colon length and colitis score were recorded on day 14. As shown in FIG. 7C, recombinant CD5L was sufficient in alleviating colitis disease severity.

Example 8. Endogeneous CD5L Forms a Heterodimer (CD5L:p40) and is Inducible During an Acute Inflammation CD5L can bind to p40, the subunit shared by the cytokines IL-12 and IL-23, and form a heterodimer in vitro. This raises the intriguing possibility that CD5L can generate different soluble mediators with potentially distinct functions. To determine whether CD5L:p40 heterodimer can be detected in vivo in biological settings, recombinant CD5L:p40 (FIG. 8A) was generated and used to optimize an ELISA that allowed the detection of endogenous CD5L:p40 heterodimer.

Figures 8A, 8B:
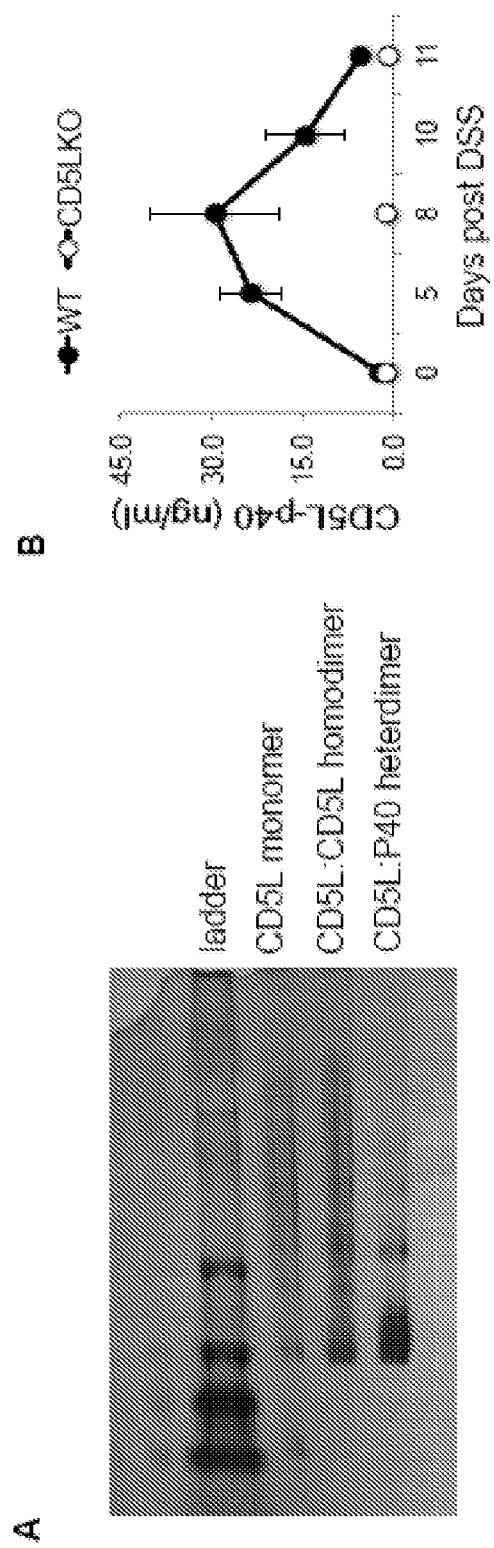
FIGS. 8A-B.

Serum was collected kinetically from wildtype and Cd5l$^{-/-}$ mice with DSS-induced colitis (2% DSS in drinking water for 6 days followed by 7 days of normal water) and the level of CD5L:p40 was measured using an ELISA assay. In the ELISA assay anti-IL-12 p40 was used to capture the heterodimer and enzyme linked anti-CD5L was used to detect the heterodimer. Data from this assay showed that natural CD5L:p40 heterodimer was induced during the course of DSS-induced colitis in serum (FIG. 8B).

Example 9. IL-27 and TLR9 Induce CD5L Dimerization

Figure 9A:
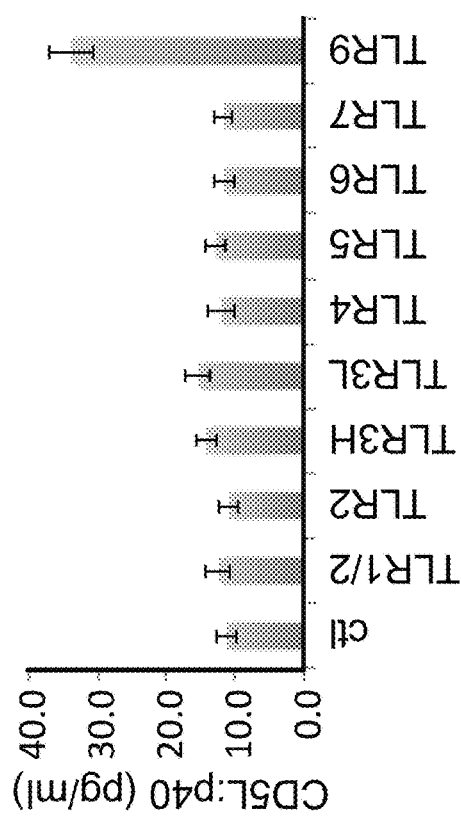
FIGS. 9A-B.
Figure 9B:
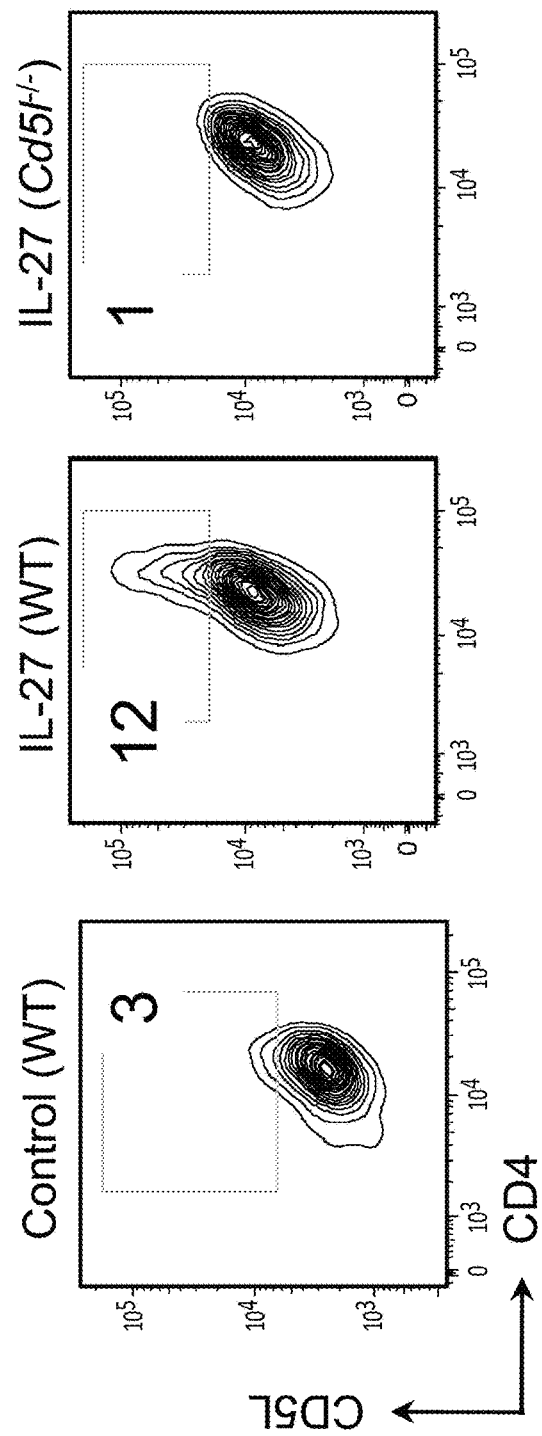

Preliminary screens were conducted to determine what signals could induce CD5L homodimer and CD5L:p40 heterodimer. In particular, bone marrow derived dendritic cells were stimulated with TLR ligands for 24 hours and the supernatant was analyzed for CD5L:p40 secretion by ELISA. The screens showed that TLR9 can induce the secretion of CD5L:p40 (FIG. 9A). To determine the signals that could induce CD5L on T cells, CD5L expression in Th0, Th1, Th2, Th17 and Tr1 cells was analyzed, and the data showed that the immunosuppressive cytokine IL-27 can indeed induce CD5L (FIG. 9B and data not shown).

Figure 10C:
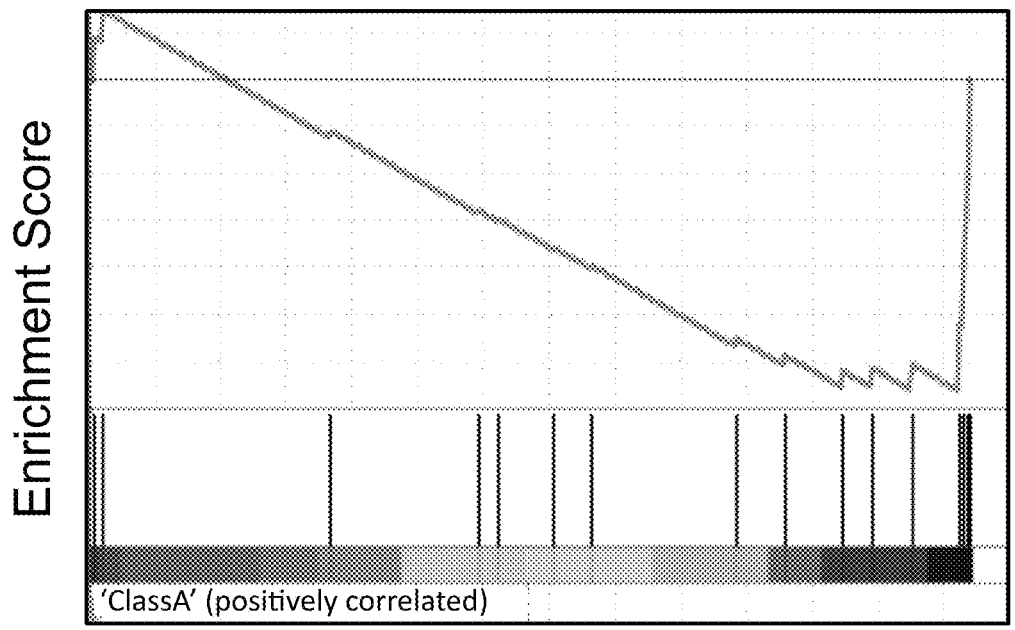
Figure 10D:
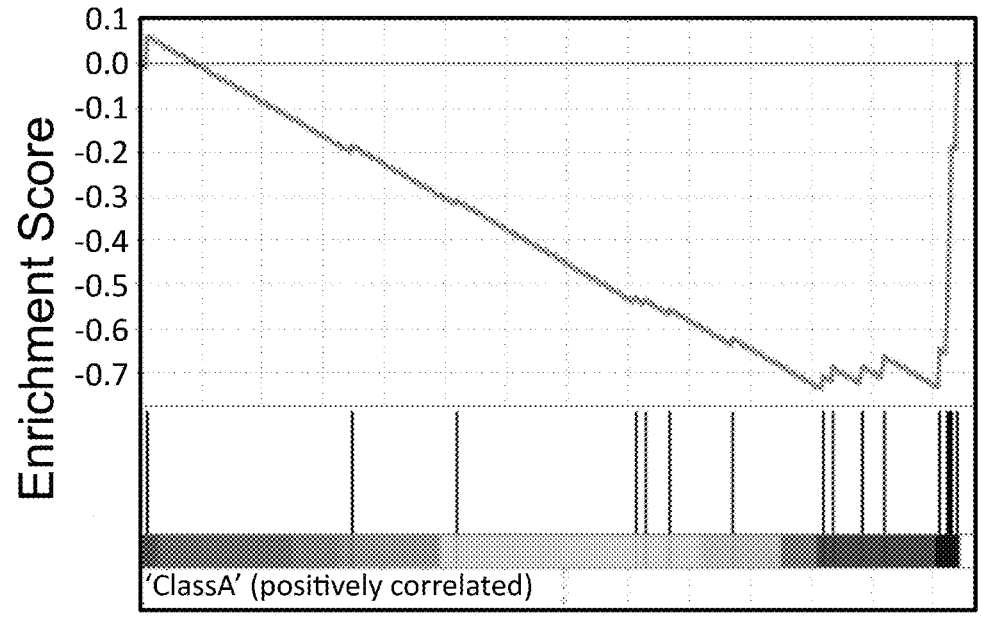

Example 10. CD5L Homo/Heterodimer Inhibits IL-17 Production and the Pathogenic Th17 Cell Signature To determine the function of CD5L homo/heterodimers on Th17 cells directly, pathogenic Th17 cells (IL-1b+IL-6+IL-23) were treated with either PBS (control), CD5L homodimers or CD5L:p40 heterodimers. IL-17 expression of T cells was measuring by FACS (FIG. 10A), and IL-17 production in serum was measured by ELISA (FIG. 10B). These experiments showed that both forms of CD5L inhibited IL-17 expression (FIGS. 10A-B).

To test whether recombinant CD5L can regulate the transcriptome of Th17 cells and particularly the pathogenic signature, the RNA expression of control and treated cells was studied with a custom-code set of 337 genes, and analyzed against signature genes of pathogenic Th17 cells (e.g., il23r, il22, il1r1, csf2) with GSEA, using the nanostring platform. The signature of pathogenic Th17 cells was significantly reduced by both CD5L:CD5L and CD5L:p40 as compared to a control (FIG. 10C (FDR q=0.031, NOM p=0.000, NES=−1.66) and 10D (FDR q=0.031, NOM p=0.000, NES=−1.47), respectively).

Figure 11A:
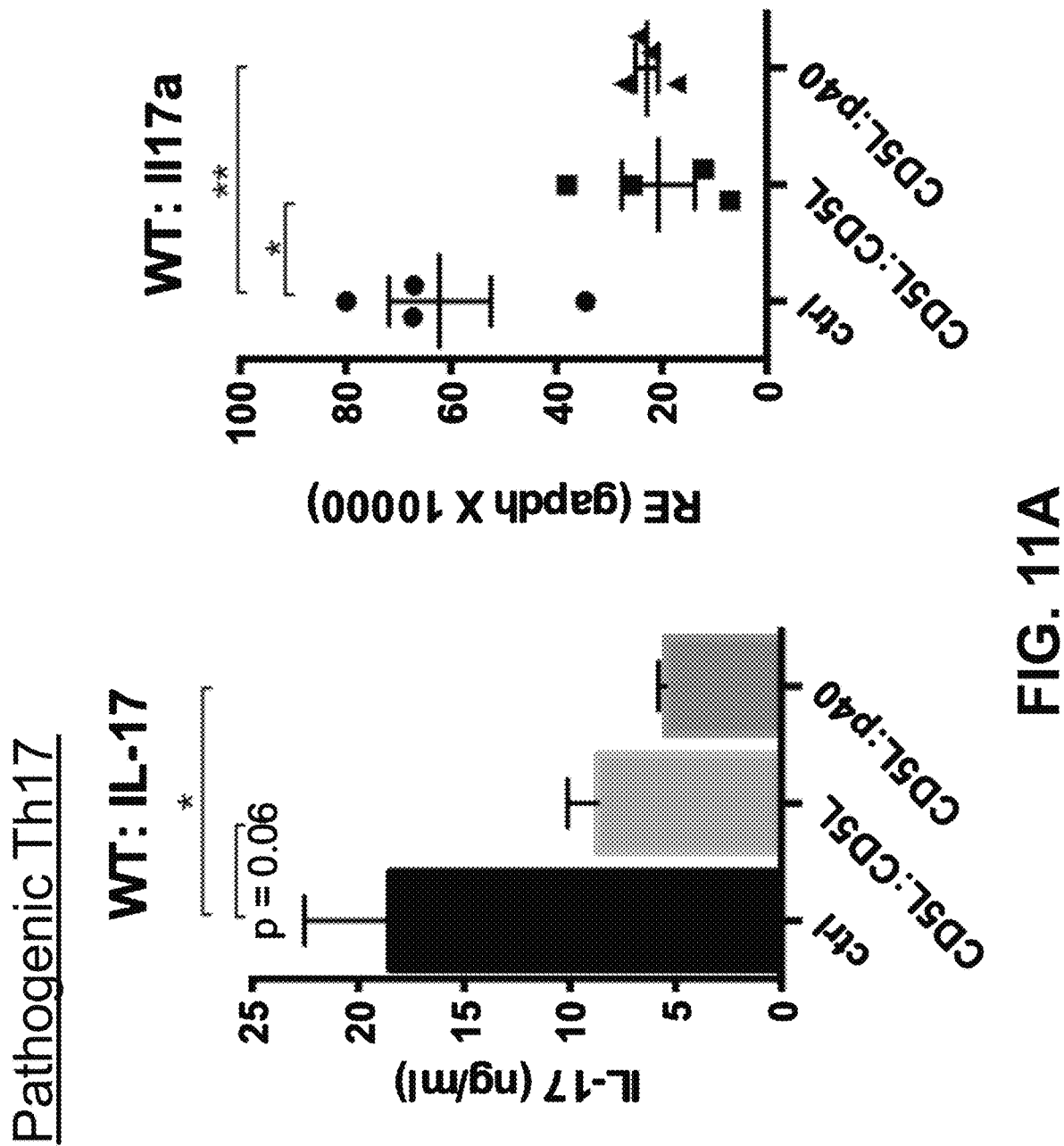
FIGS. 11A-B.
Figure 11B:
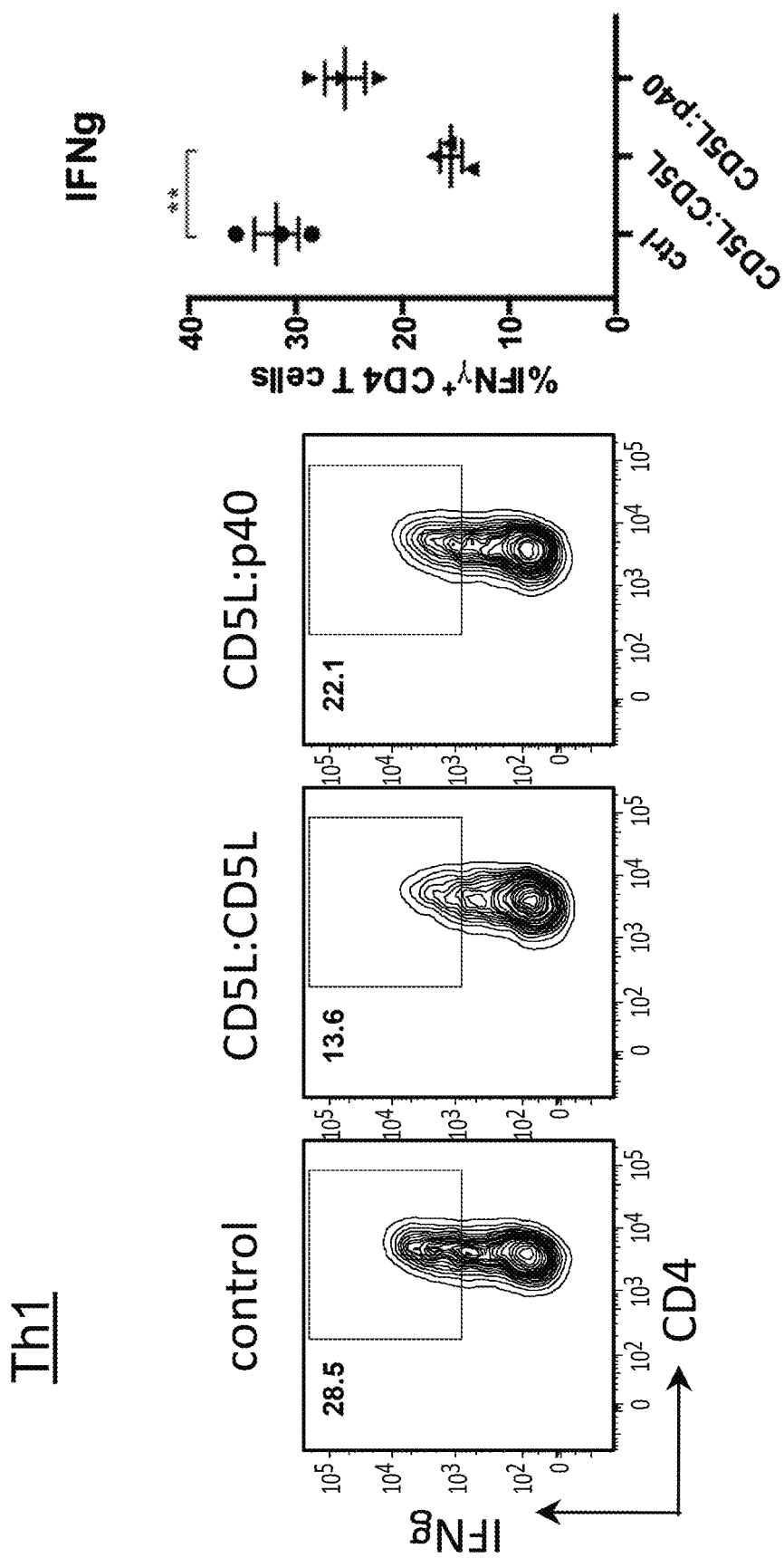

Example 11. CD5L Suppresses IL-17 and IFNg Expression from Pathogenic Th17 Cells and Th1 Cells, Respectively Pathogenic Th17 cells and Th1 cells were differentiated from naïve CD4 cells ($CD44^{low}CD62L^+CD25-CD4^+$) from wildtype mice with IL-1b, IL-6, and IL-23 (Th17) or IL-12 (Th1) in the presence of a control, CD5L homodimer, or CD5L:p40 heterodimer for 48 hrs (Th17) or 72 hours (Th1). IL-27 expression in Th17 cells was measured by ELISA in supernatant (FIG. 11A, left side) and by qPCR from RNA purified from cells (FIG. 11A, right side). IFNg expression in Th1 cells was measured by intracellular staining followed by flow cytometry analysis (FIG. 11B). The results showed that CD5L suppresses IL-17 and IFNg production in pathogenic T cells.

Figure 12A:
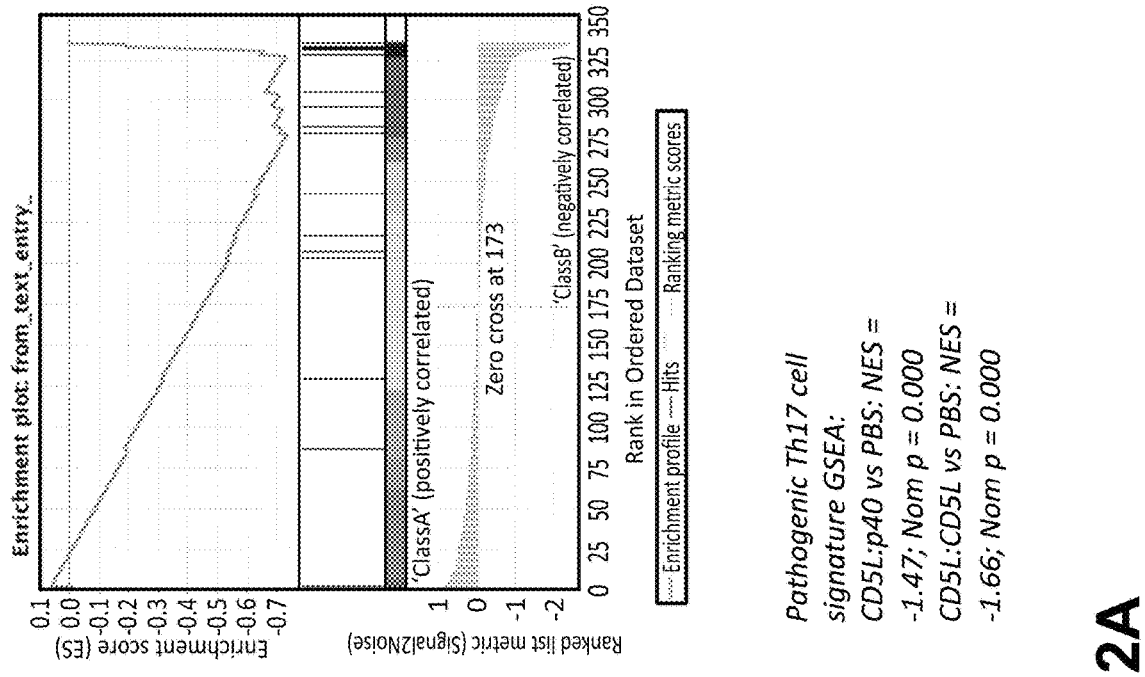
FIGS. 12A-B.
Figure 12A:
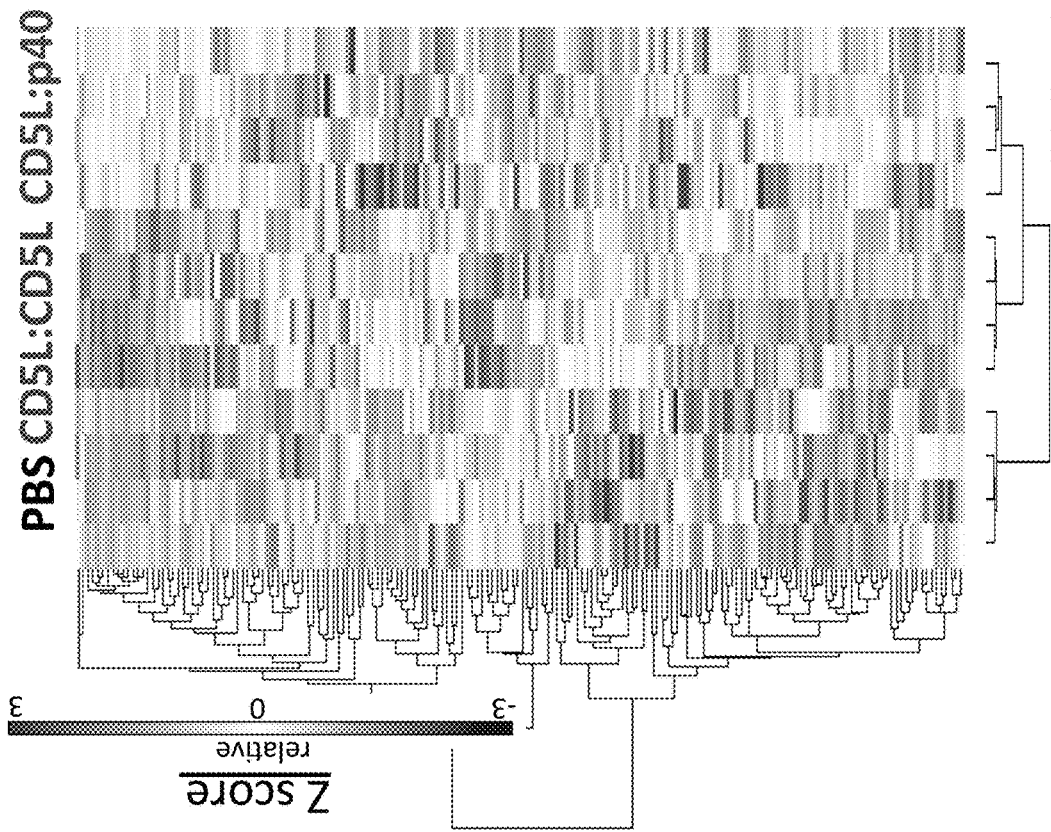
Figure 12B:
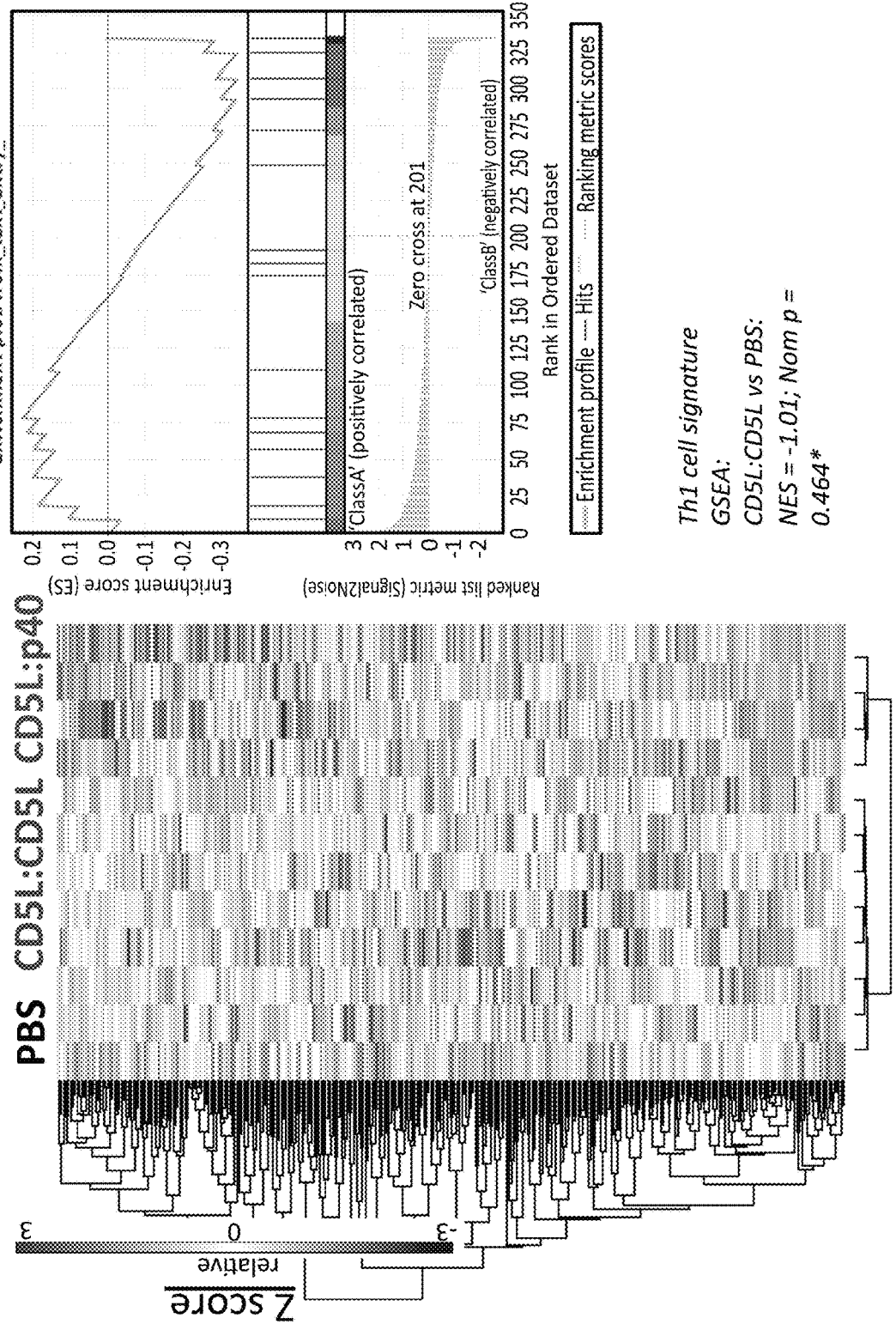

To assess pathogenic T cell signatures, RNA was extracted from both Th17 and Th1 cells after 48 hours of differentiation. Extracted RNA was analyzed with a custom codeset of 337 genes using the nanostring platform (four replicates for each conditions were measured). The Spearman coefficient was used for clustering. A heat map of differentially expressed genes as compared to control (defined by p<0.05) is shown in FIG. 12A for Th17 cells and FIG. 12B for Th1 cells (left panels). GSEA analysis against the pathogenic signatures are shown in the right panels of FIGS. 12A and B.

Example 12. Endogenous CD5L Promotes EAE Resolution and is Expressed by Both Non-Pathogenic Th17 Cells and CD11b+ Cells During EAE Development To determine which cells express CD5L during EAE, $cd5l^{-/-}$ mice were immunized with MOG/CFA to induce EAE and followed for clinical scores. Th17 cells (IL-17.GFP+CD4+) and CD11b+ myeloid cells were sorted from both spleen and CNS of mice at peak disease (score=3). Mice with global CD5L deficiency showed more severe and sustained EAE compared to controls (FIG. 13A), indicated that CD5L contributes to EAE resolution.

To assess CD5L expression in EAE, IL-17 GFP reported mice were immunized with MOG/CFA to induce EAE. Mice were sacrificed at peak of disease (score=3). Th17 cells were sorted based on CD4+GFP+ and macrophage were sorted based on CD11b+ from both the spleen and CNS of the mice. RNA was purified from sorted cells and qPCR was used to measured CD5L expression. The experiments showed that CD5L was preferentially expressed by Th17 cells in the spleen and by macrophage cells in the CNS (FIG. 13B).

Figure 14A:
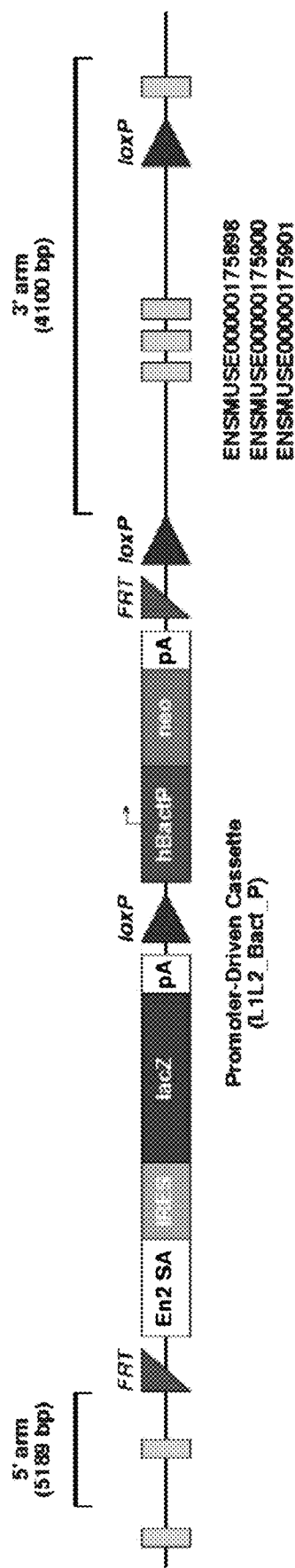
FIGS. 14A-B.
Figure 14B:
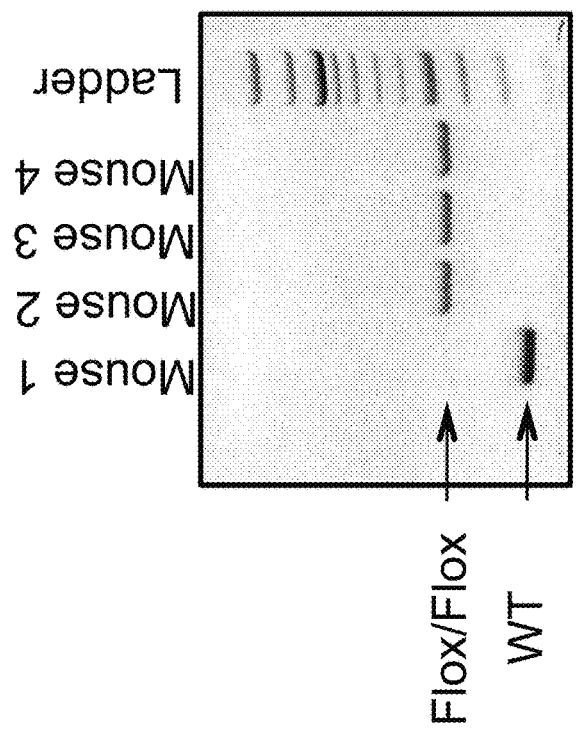

Example 13. Generation of CD5L Conditional Knockout Mouse; Role in Tumor Immunity To study the cellular source of CD5L during EAE development, CD5L flox/flox mice (CD5Lfl/fl) were generated by crossing FLPo mice and mice that were heterozygous with the construct shown in FIG. 14A (purchased from EUCOMM/KOMP). The CD5L flox/flox mice were bred to homozygosity and crossed with CD4-Cre, IL-17-Cre and LysM-Cre for conditional deletion of the Cre-loxP system. Representative genotyping results for CD5L flox/flox mice are shown in FIG. 14B. $CD5L^{fl/fl}$ mice were successfully crossed with LysMCre, CD4Cre and IL-17Cre mice to specifically delete CD5L in myeloid lineage cells, T cells and IL-17-producing cells respectively.

Figures 15A, 15B:
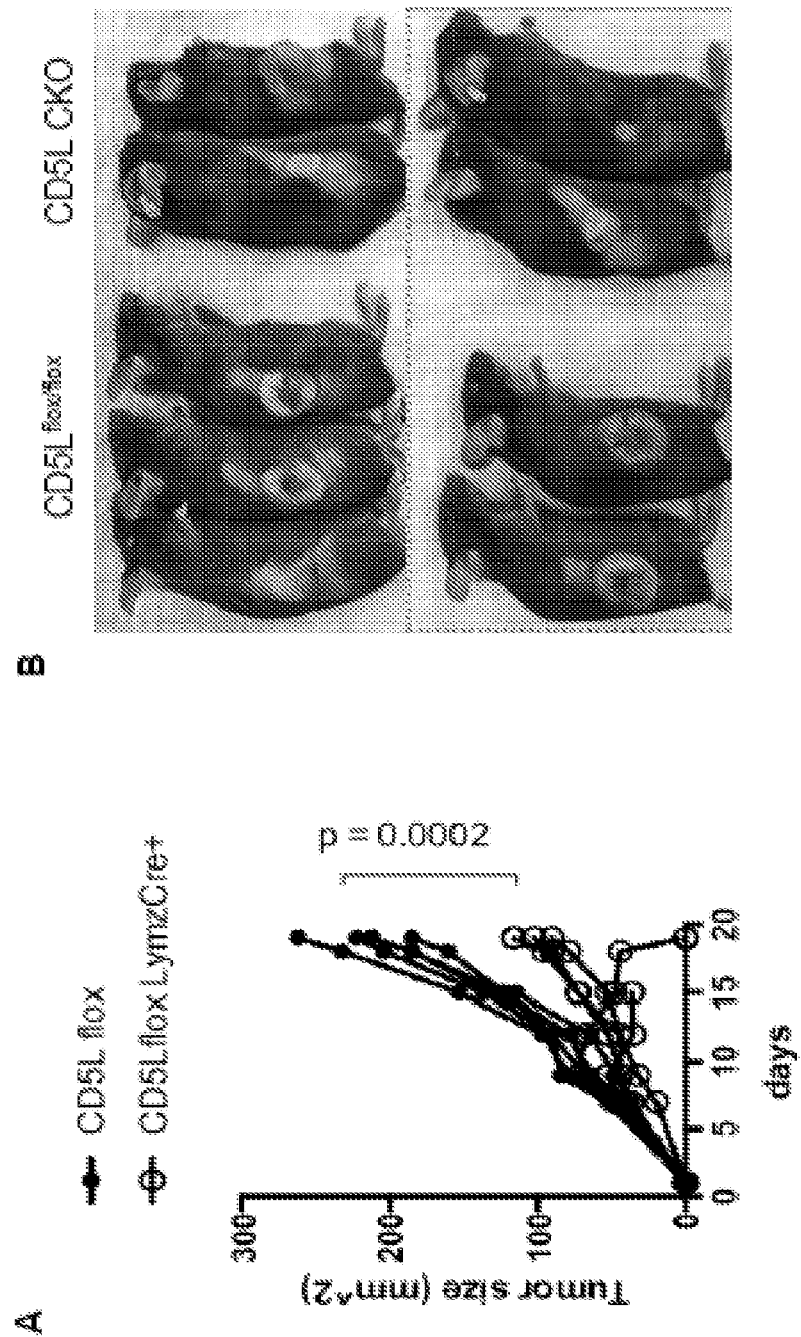
FIG. 15A-B.

$CD5L^{flox/flox}Lymx^{Cre+}$ (CD5L CKO) and $CD5L^{flox/flox}$ mice were injected with $1\times10^6$ MC38 colon carcinoma subcutaneously on the right flank. Tumor size was measured up to 19 days post-injection, and is plotted in FIG. 15A. Pictures of mice sacrificed on day 19 post tumor cell injection are shown in FIG. 15B.

Figure 16:
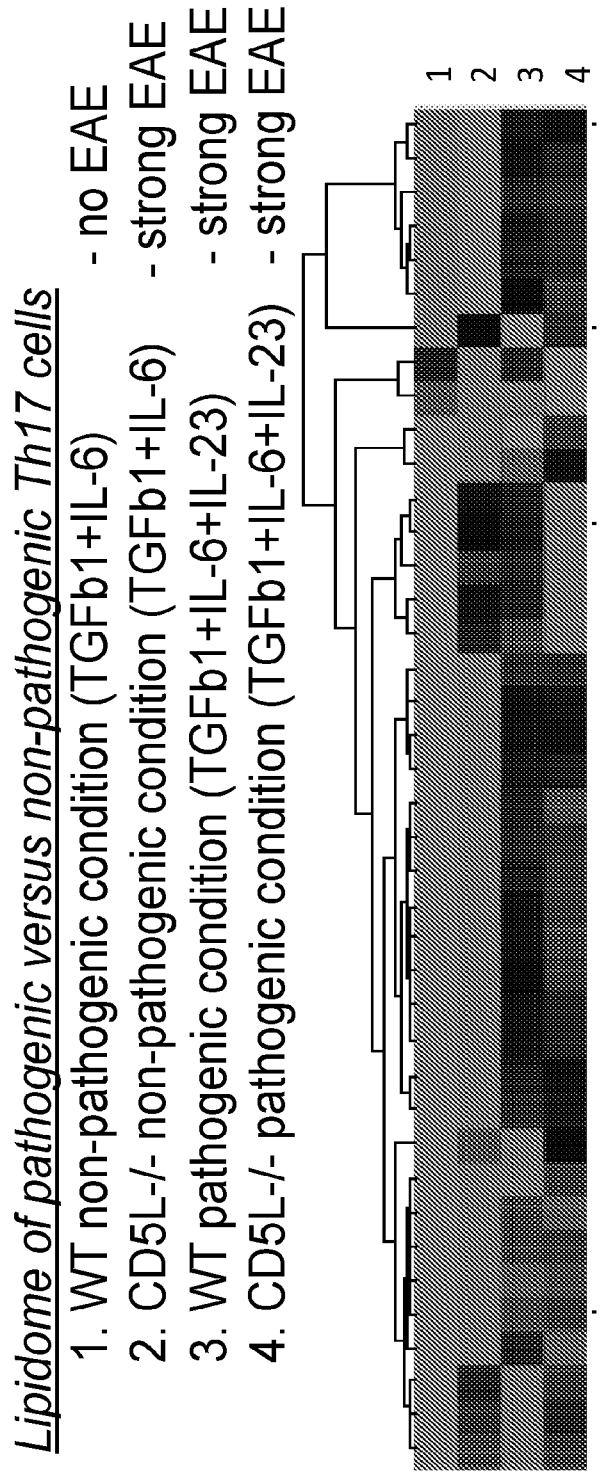
FIG. 16 depicts the lipidome of wildtype and cd5l$^{−/−}$ Th17 cells differentiated under pathogenic and non-pathogenic conditions.

Example 14. CD5L and IL-23 Alter Lipidome of Th17 Cells in Correlation with T Cell Function and EAE Th17 cells were differentiated from naïve cells under pathogenic and non-pathogenic conditions and harvested for LC/MS at 96 hours. The lipidome of wildtype and $Cd5l^{-/-}$ Th17 cells was analyzed. A striking correlation of the lipidome of Th17 cells to their function and ability to induce EAE was found (FIG. 16). In fact, Th17 cell function could be changed based on alterations of the Th17 cell lipidome.

Figure 17:
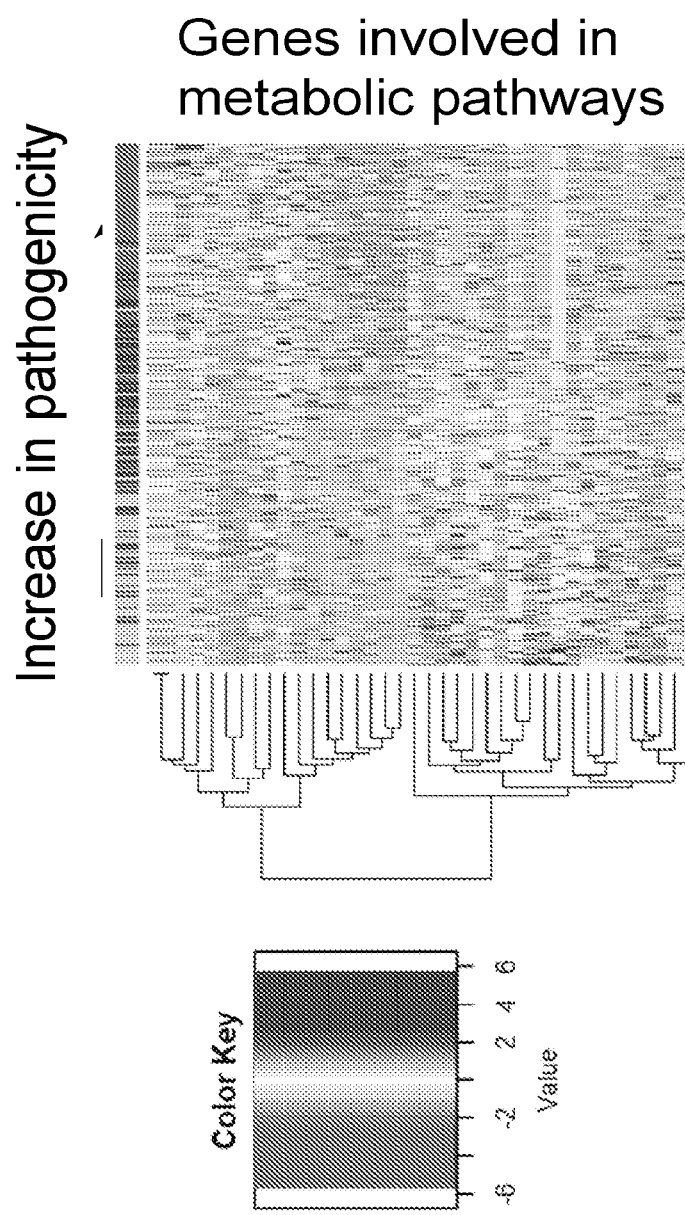
FIG. 17 is a plot showing that metabolic transcriptome expression covaries with Th17 cell pathogenicity.

Example 15. Gene Expression Profile of Metabolic Pathways Correlates with Th17 Cell Pathogenicity To determine whether metabolic genes are differentially expressed at the transcriptome level in Th17 cells with different functional state, the metabolic transcriptome in single cell RNAseq data was analyzed. The analysis showed metabolic transcriptome expression covariance with Th17 cell pathogenicity (FIG. 17).

Figures 18A, 18B:
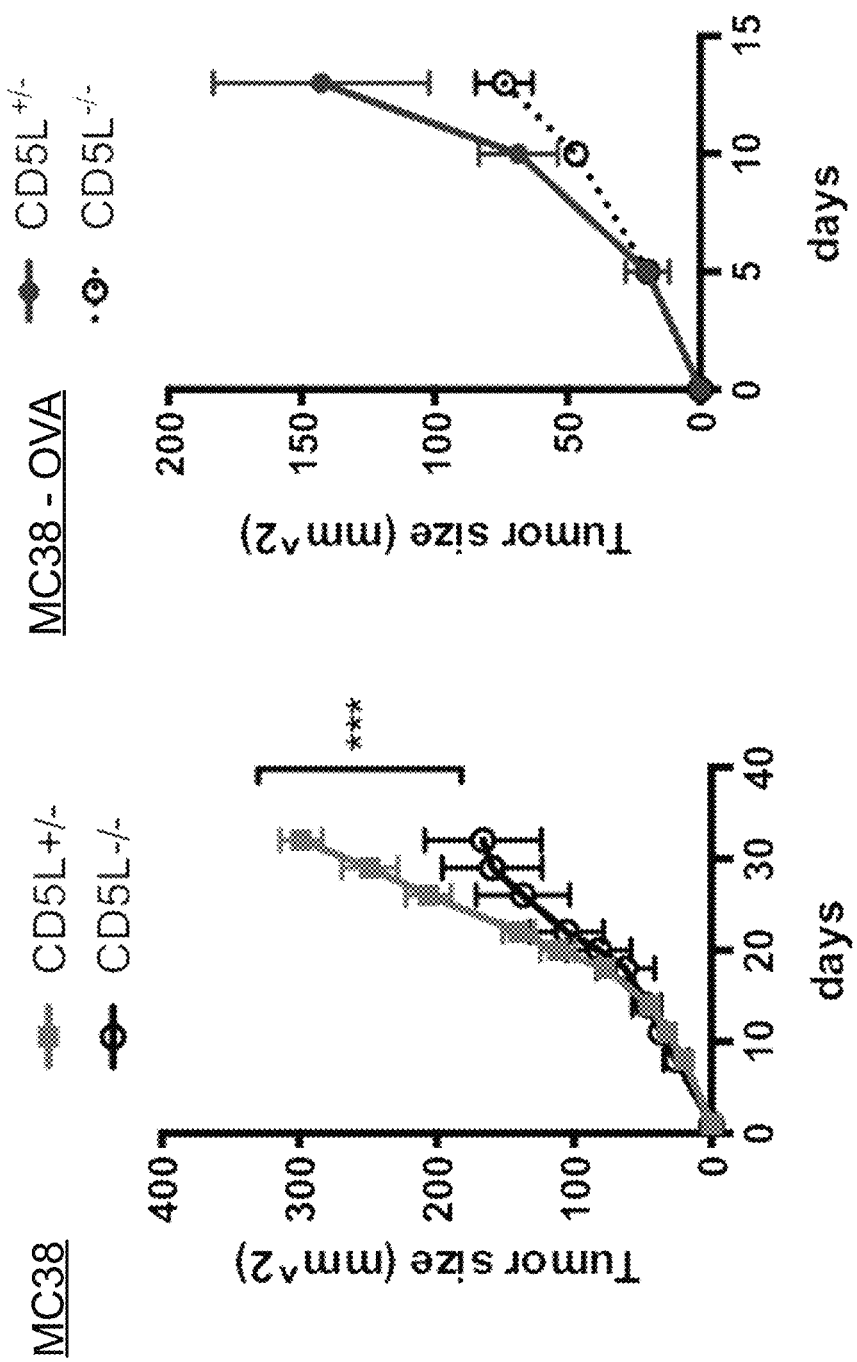
FIGS. 18A-D.
Figure 18C:
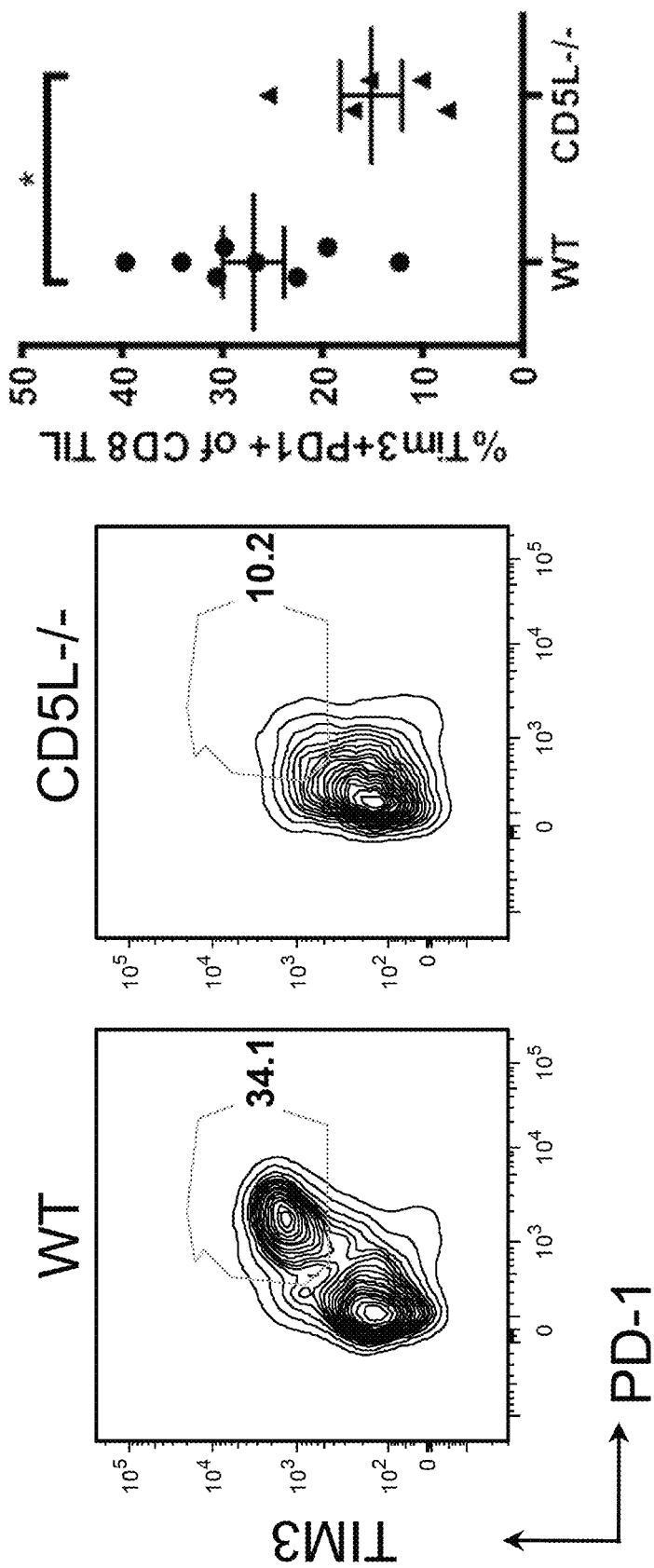
Figure 18D:
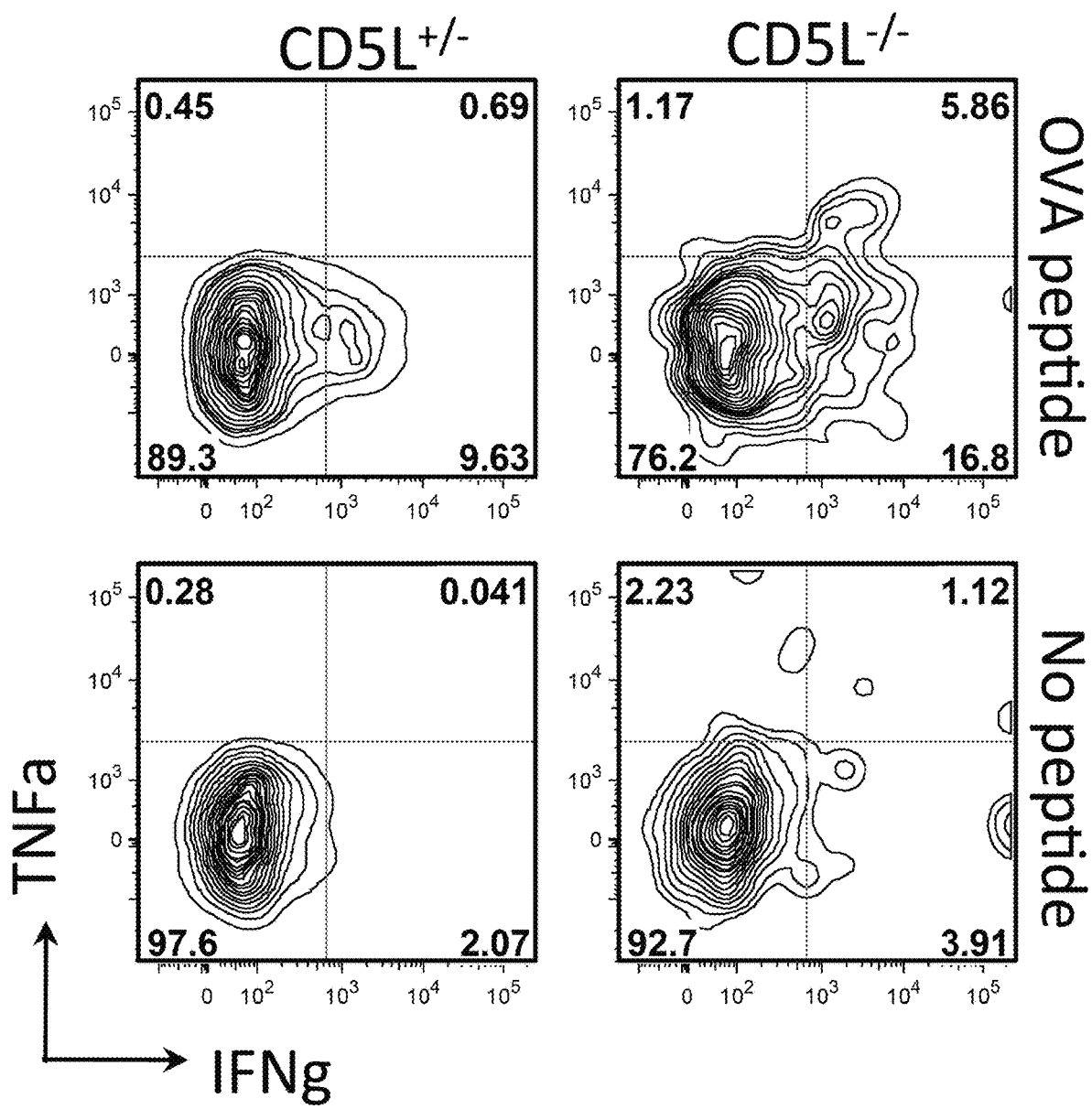
Figure 18D:
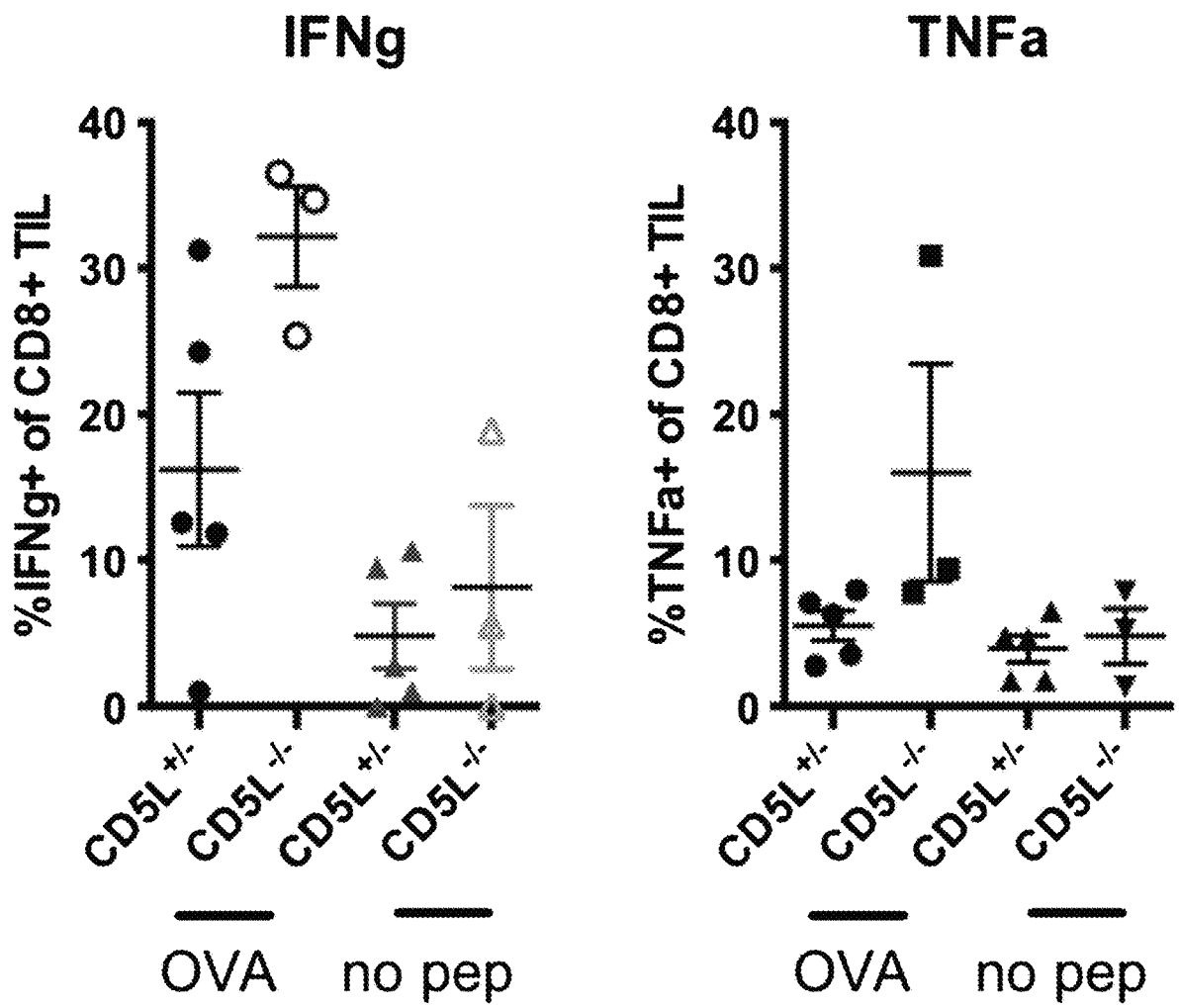

Example 16. CD5L Plays a Critical Role in Tumor Immunity, Regulating T Cell Exhaustion Littermate controls of $CD5L^{+/-}$ and $CD5L^{-/-}$ mice were grafted with $1\times10^6$ MC38 or MC38-OVA colon carcinoma subcutaneously on the right flank, and then tumor progression was followed. Tumor size progression for MC38 and MC38-OVA experiments are shown FIGS. 18A and B, respectively. Tumor infiltrating lymphocytes were isolated from MC38 on day 30 and analyzed, and the results are shown in FIG. 19C. Tumor infiltrating lymphocytes were isolated from MC38-OVA on day 14 and inculcated with OVA peptide or no peptide (control) for 20 hours. Brefeldin A and monensin was added in the last 4 hours and cytokines were measured intracellularly by flow cytometry (see FIG. 19D). These results demonstrate that CD5L deficiency inhibits T cell dysfunction and promotes tumor suppression.

Example 17: Link Between CD5L:p40 Heterodimer and Tumor Progression

Figure 19A:
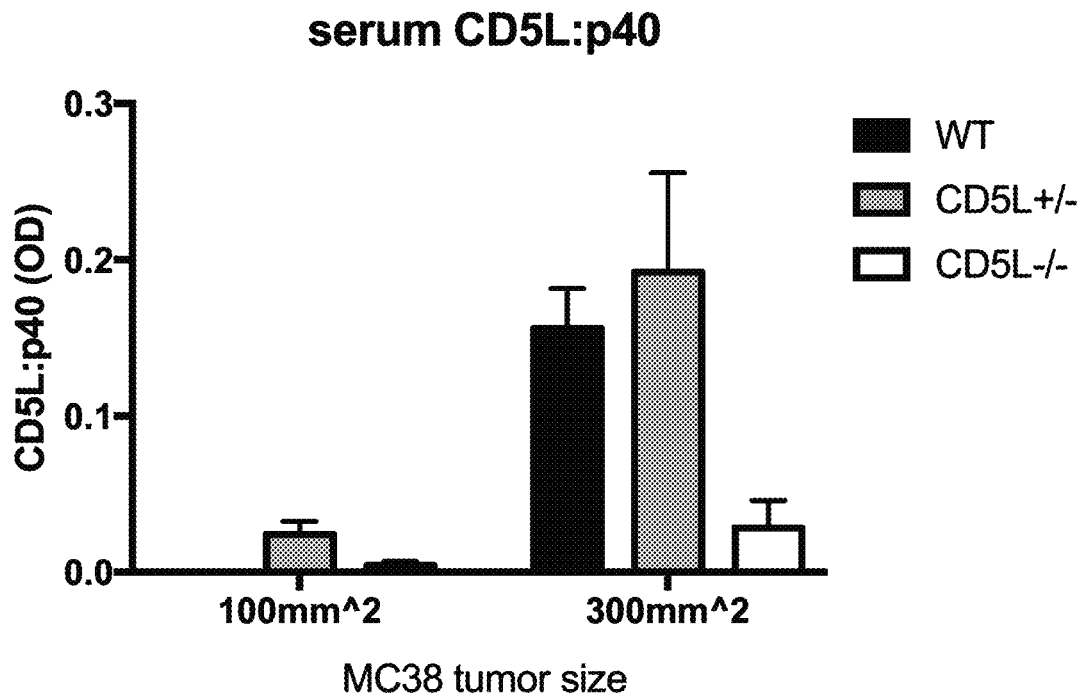
FIGS. 19A-B.
Figure 19B:
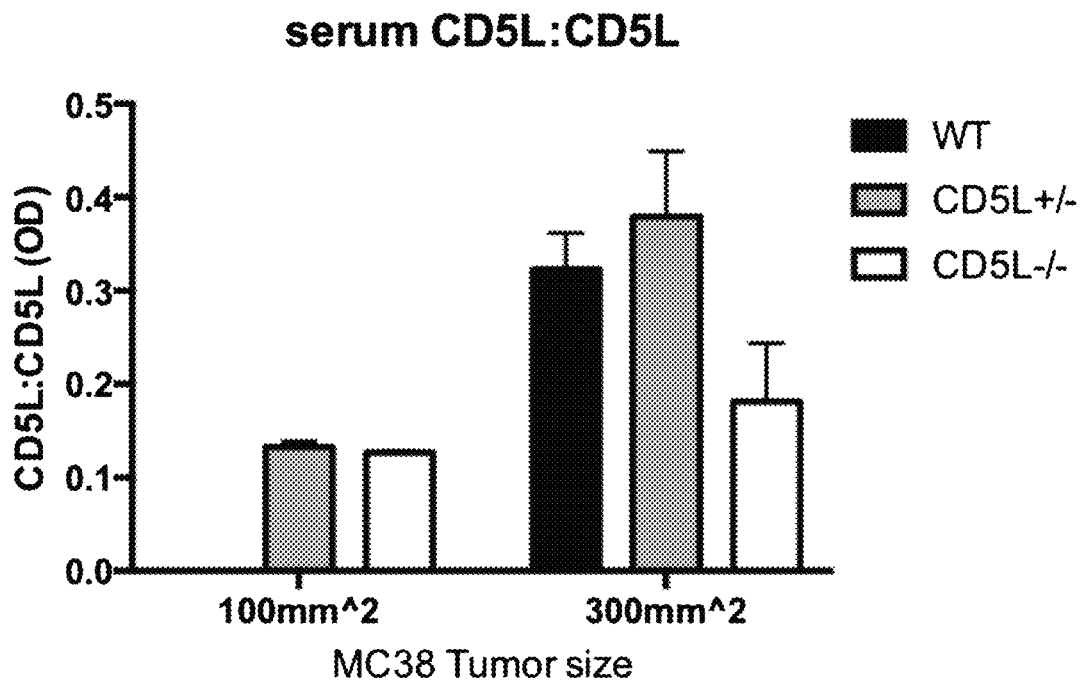

Litter mate controls of wildtype, CD5L$^{+/+}$ and CD5L$^{-/-}$ mice were injected with 1×10$^6$ MC38 colon carcinoma subcutaneously on the right flank, and CD5L:CD5L and CD5L:p40 were measured in serum during tumor progression. Serum was obtained and measured for (a) CD5L:p40 heterodimer using sandwich ELISA captured by anti-IL-12p40 antibody and detected with biotinylated anti-CD5L antibody and (b) CD5L:CD5L homodimer using sandwich ELISA captured and detected by anti-CD5L antibodies. Results are shown in FIGS. 19A-B.

Example 18: CD5L Suppresses Pathogenic T Cell Signatures

Figure 20:
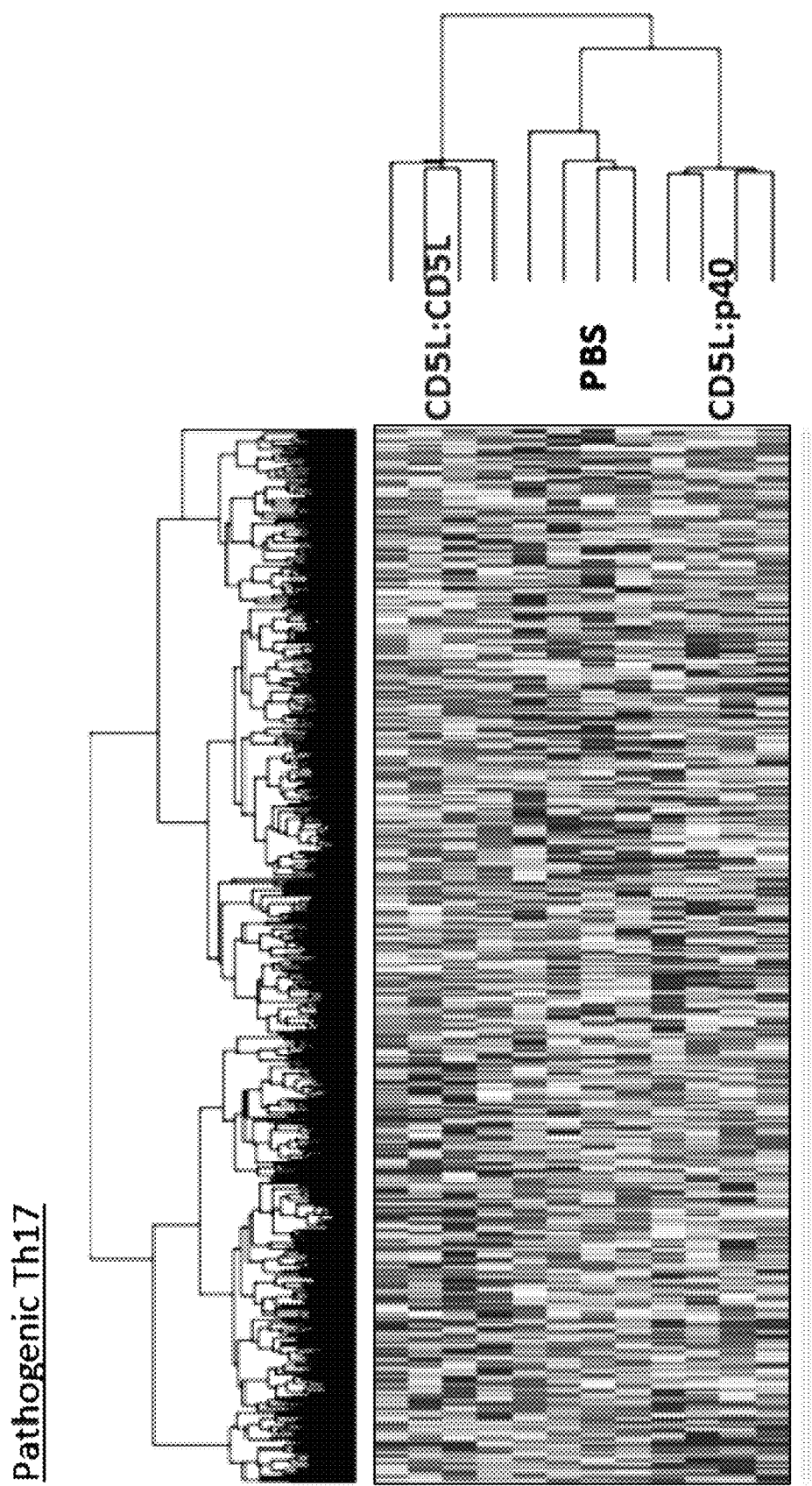
FIG. 20 sets forth a heat map showing differentially expressed genes in CD5L:CD5L and CD5L:p40 experiments as compared to the control (differentially expressed genes are defined by p<0.5 as compared to control).

Pathogenic Th17 cells and Th1 cells were differentiated from naïve CD4 T cells (CD44$^{low}$CD62L$^+$CD25-CD4$^+$) from wildtype mice with IL-1b, IL-6 and IL-23 (Th17) in the presence of control, CD5L homodimer, or CD5L:p40 heterodimer for 48 hours. RNA were extracted and subjected to RNAseq using NextSeq. A heat map prepared from this data (FIG. 20; four replicates from each condition is shown; spearman coefficient was used for clustering) shows that the presence of CD5L:CD5L results in expression of different signature genes than does the presence of CD5L:p40. The heat map shows differentially expressed genes in the CD5L:CD5L and CD5L:p40 experiments as compared to the control (differentially expressed genes are defined by p<0.5 as compared to control). This data demonstrates that both CD5L:CD5L and CD5L:p40 can suppress pathogenic T cell signatures, but that the suppression via CD5L:CD5L and CD5L:p40 is associated with expression of distinct cell signatures.

Example 19: In Vivo Effect of CD5L:p40

Figure 21A:
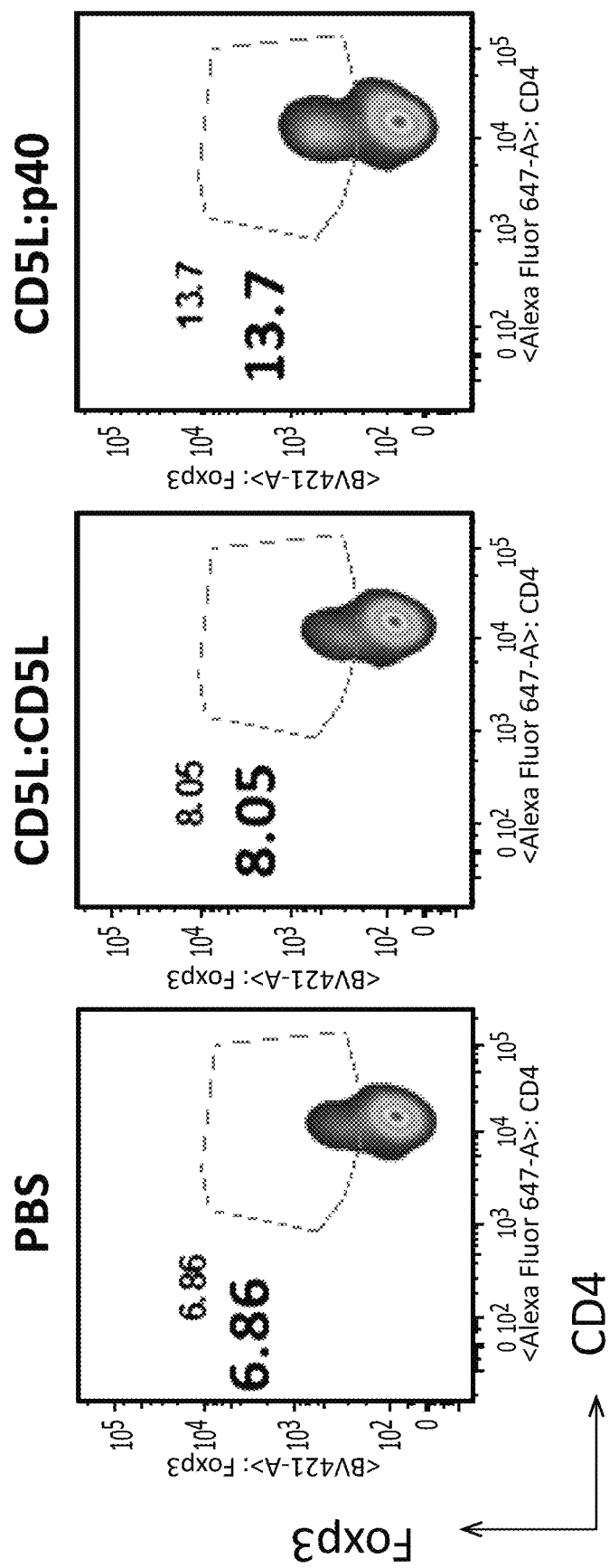
FIGS. 21A-B.
Figure 21A:
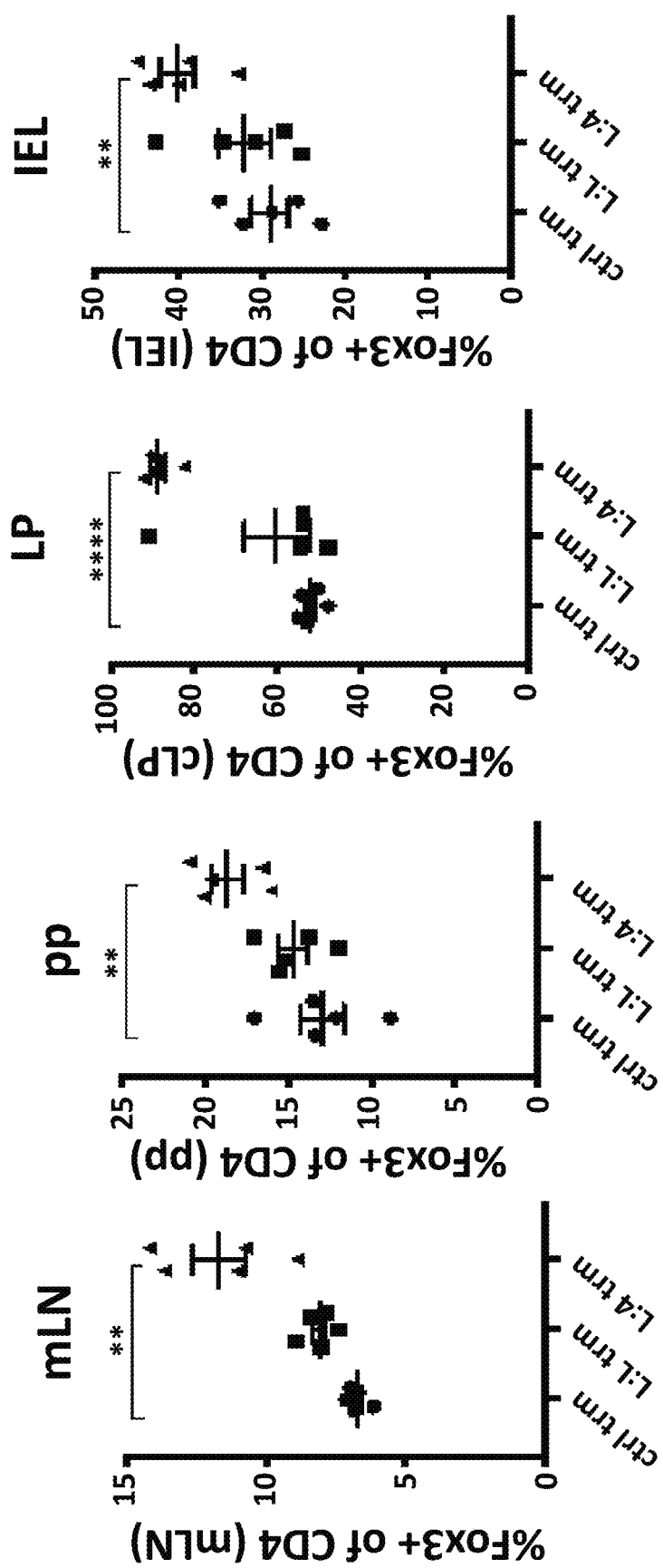
Figure 21B:
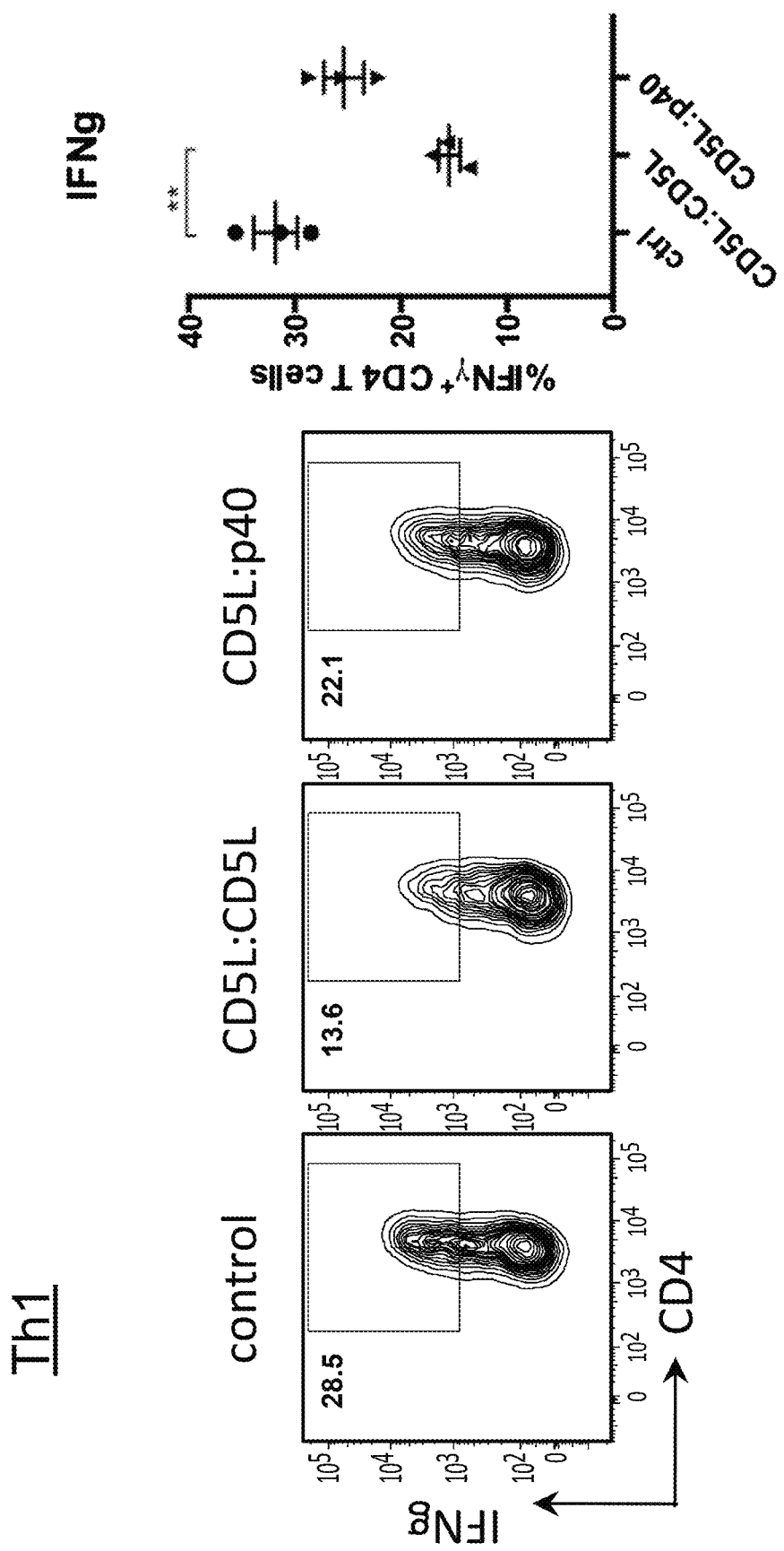

To assess in vivo efficacy of CD5L dimers, wildtype mice were treated with 2% DSS in drinking water for 5 days, followed by normal water for 6 days. Mice were injected with PBS, recombinant CD5L:CD5L, or recombinant CD5L:p40 intraperitoneally on days 4, 6, and 8. Cells from mesenteric lymph nodes (mLN), peyer's patches (pp), *Lamina propria* of colon (LP), and intraepithelial lymphocytes (IEL) were isolated, stained, and analyzed directly with flow cytometry on day 11. The frequency of Foxp3+ CD4 T cells in various cell types is shown in FIG. 21A. The frequency of ILC3 as defined by CD45+Lineage-Thy1.2+CD127+Rorγt is shown in FIG. 21B. This data demonstrates that CD5L:p40 increased Tregs in vivo in DSS-induced colitis.

Figure 22A:
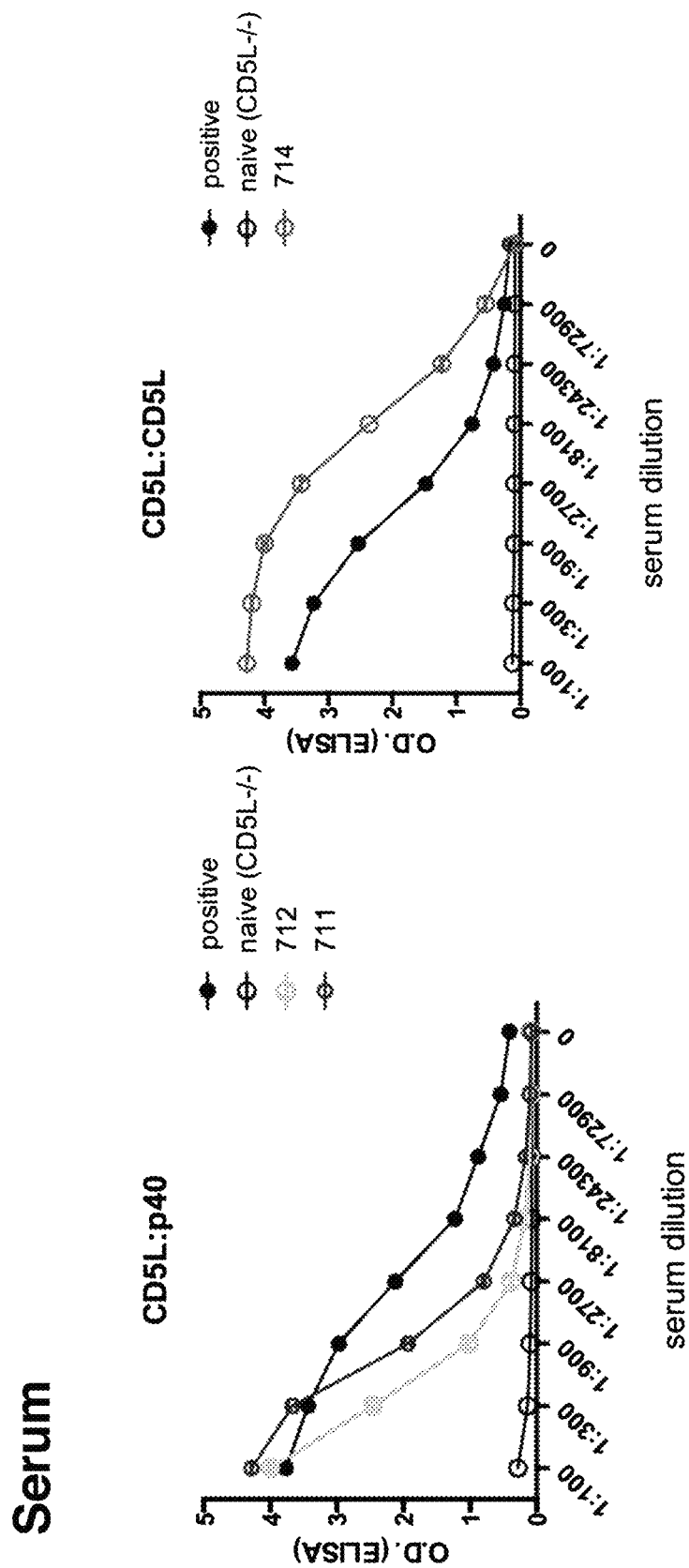
FIGS. 22A-B.
Figure 22B:
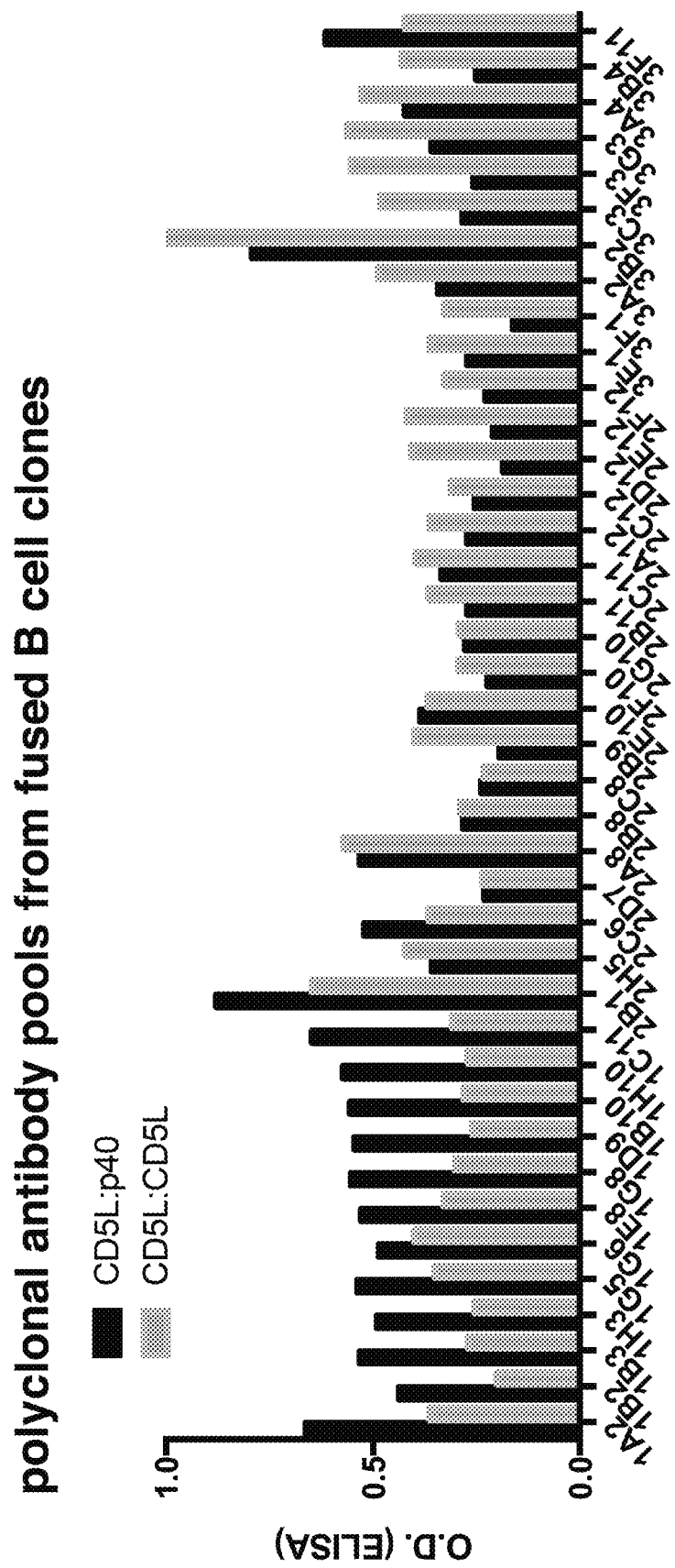

Example 20: Generation of Anti-CD5L:CD5L Homodimer and Anti-CD5L:p40 Heterodimer Antibodies CD5L-/- mice were immunized with either recombinant CD5L:CD5L (labeled "714" in FIG. 22A) or recombinant CD5L:p40 ("711", "712") for antibody generation. Serum samples were taken from each mouse before spleen infusion and tested for their ability to bind to either CD5L:p40 or CD5L:CD5L in a sandwich ELISA assay (FIG. 20A). B cells from the spleen of immunized mice were fused to generate pools of clones that were allowed to expand. Serum from the pools were tested in the same ELISA assay. Polyclonal antibody pools that have preferential specificity to either CD5L:p40 or CD5L:CD5L were observed (FIG. 22B).

It is contemplated that human antibodies CD5L:CD5L and CD5L:p40 can be prepared based on the degree of homology between mouse and human CD5L and p40 (FIGS. 23A and C). Also shown are homology between mouse and human protein sequences in p19 and p35 (FIGS. 23B and D), which can form a dimer with p40.

REFERENCES

Abdi et al., (2014). Free IL-12p40 monomer is a polyfunctional adaptor for generating novel IL-12-like heterodimers extracellularly. Journal of immunology 192, 6028-6036.

Burkett et al., (2015). Pouring fuel on the fire: Th17 cells, the environment, and autoimmunity. J Clin Invest 125, 2211-2219.

Cho et al., (2015). Heterogeneity of autoimmune diseases: pathophysiologic insights from genetics and implications for new therapies. Nature medicine 21, 730-738.

Didonna, A. and J. R. Oksenberg, (2015) Genetic determinants of risk and progression in multiple sclerosis. Clin Chim Acta, 449: p. 16-22.

Floss, D. M., et al. (2015) Insights into IL-23 biology: From structure to function. Cytokine Growth Factor Rev. 26(5): p. 569-78.

Gaublomme, J. T., et al., Single-Cell Genomics Unveils Critical Regulators of Th17 Cell Pathogenicity. Cell, 2015. 163(6): p. 1400-12.

Hill et al., (2008). Retinoic acid enhances Foxp3 induction indirectly by relieving inhibition from CD4+CD44hi Cells. Immunity 29, 758-770.

Jeoung, N. H. and R. A. Harris (2008) Pyruvate dehydrogenase kinase-4 deficiency lowers blood glucose and improves glucose tolerance in diet-induced obese mice. Am J Physiol Endocrinol Metab. 295(1): p. E46-54.

Kurokawa et al., (2010). Macrophage-derived AIM is endocytosed into adipocytes and decreases lipid droplets via inhibition of fatty acid synthase activity. Cell metabolism 11, 479-492.

Langrish, C. L., et al. (2005) IL-23 drives a pathogenic T cell population that induces autoimmune inflammation. J Exp Med. 201(2): p. 233-40.

Lee, Y., et al. (2012) Induction and molecular signature of pathogenic TH17 cells. Nat Immunol. 13(10): p. 991-9.

Lock, C., et al. (2002) Gene-microarray analysis of multiple sclerosis lesions yields new targets validated in autoimmune encephalomyelitis. Nat Med. 8(5): p. 500-8.

Mascanfroni, I. D., et al. (2013) IL-27 acts on DCs to suppress the T cell response and autoimmunity by inducing expression of the immunoregulatory molecule CD39. Nat Immunol. 14(10): p. 1054-63.

Miyazaki et al., (1999). Increased susceptibility of thymocytes to apoptosis in mice lacking AIM, a novel murine macrophage-derived soluble factor belonging to the scavenger receptor cysteine-rich domain superfamily. The Journal of experimental medicine 189, 413-422.

Parnas, O., et al. (2015) A Genome-wide CRISPR Screen in Primary Immune Cells to Dissect Regulatory Networks. Cell. 162(3): p. 675-86.

Sanjurjo et al., (2015). The human CD5L/AIM-CD36 axis: A novel autophagy inducer in macrophages that modulates inflammatory responses. Autophagy 11, 487-502.

Stumhofer, J. S. et al. (2007) Interleukins 27 and 6 induce STAT3-mediated T cell production of interleukin 10. Nat Immunol. 8(12): p. 1363-71.

Teng et al., (2015). IL-12 and IL-23 cytokines: from discovery to targeted therapies for immune-mediated inflammatory diseases. Nature medicine 21, 719-729.

Wang, C., et al. (2015) CD5L/AIM Regulates Lipid Biosynthesis and Restrains Th17 Cell Pathogenicity. Cell. 163(6): p. 1413-27.

Wang and Karin, (2015). The IL-23 to IL-17 cascade inflammation-related cancers. Clin Exp Rheumatol 33, 87-90.

Yosef, N., et al. (2013) Dynamic regulatory network controlling TH17 cell differentiation. Nature. 496(7446): p. 461-8.

Yoshida, H. and C. A. Hunter (2015) The immunobiology of interleukin-27. Annu Rev Immunol. 33: p. 417-43.

Zhu, C., et al. (2015) An IL-27/NFIL3 signalling axis drives Tim-3 and IL-10 expression and T-cell dysfunction. Nat Commun. 6: p. 6072.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of suppressing an immune response in a subject, the method comprising administering to the subject a therapeutically effective amount of
    a recombinant soluble CD5L:p40 heterodimer, wherein the subject has an autoimmune disease.

2. The method of claim 1, wherein the autoimmune disease is Multiple Sclerosis (MS), Irritable Bowel Disease (IBD), Crohn's disease, spondyloarthritides, Systemic Lupus Erythematosus (SLE), Vitiligo, rheumatoid arthritis, psoriasis, Sjögren's syndrome, or diabetes.

* * * * *

UNITED STATES PATENT AND TRADEMARK OFFICE
CERTIFICATE OF CORRECTION

PATENT NO. : 11,884,717 B2
APPLICATION NO. : 17/226506
DATED : January 30, 2024
INVENTOR(S) : Vijay K. Kuchroo et al.

It is certified that error appears in the above-identified patent and that said Letters Patent is hereby corrected as shown below:

In the Specification

In Column 4, Line 46, delete "$CD5L^{flox/flox}Lymx^{cre+}$" and insert -- $CD5L^{flox/flox}Lymz^{cre+}$ --.

In Column 24, Line 49, delete "CD28+." and insert -- CD28+, --.

In Column 24, Line 50, delete "CD451RO+" and insert -- CD45RO+ --.

In Column 24, Lines 53-54, delete "DSC BEADS®" and insert -- DYNABEADS® --.

In Column 25, Line 14, delete "CD 11b," and insert -- CD11b, --.

In Column 26, Line 14, delete "$CD4^+$" and insert -- CD4+ --.

In Column 26, Line 16, delete "cells" and insert -- T cells --.

In Column 27, Line 15, delete "LSI" and insert -- LSR --.

In Column 53, Line 2, delete "310E/3111;" and insert -- 310E/311I; --.

In Column 54, Line 51, delete "Fokl." and insert -- Fok1. --.

In Column 65, Line 40, delete "CD11c'" and insert -- $CD11c^+$ --.

In Column 68, Line 29, delete "$CD5L^{flox/flox}Lymx^{cre+}$" and insert -- $CD5L^{flox/flox}Lymz^{cre+}$ --.

Signed and Sealed this
Eleventh Day of June, 2024

Katherine Kelly Vidal
*Director of the United States Patent and Trademark Office*

SEQUENCE LISTING

```
<160> NUMBER OF SEQ ID NOS: 43

<210> SEQ ID NO 1
<211> LENGTH: 328
<212> TYPE: PRT
<213> ORGANISM: Homo sapiens

<400> SEQUENCE: 1

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
```

-continued

```
                    245                 250                 255
Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 2
<211> LENGTH: 347
<212> TYPE: PRT
<213> ORGANISM: Homo sapiens

<400> SEQUENCE: 2

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
            20                  25                  30

Cys Glu Gly Arg Val Glu Val Glu Gln Lys Gly Gln Trp Gly Thr Val
        35                  40                  45

Cys Asp Asp Gly Trp Asp Ile Lys Asp Val Ala Val Leu Cys Arg Glu
    50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140

Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285
```

```
Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Gly
            340                 345

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Gly Ser
1

<210> SEQ ID NO 4
<211> LENGTH: 12
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Gly Gly Ser Gly Gly Gly Ser Gly Gly Gly Ser
1               5                   10

<210> SEQ ID NO 5
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Ala Glu Ala Ala Ala Lys Ala
1               5

<210> SEQ ID NO 6
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Gly Gly Gly Ser Gly Gly Gly Gly Ser Gly Gly Gly Gly Ser
1               5                   10                  15

<210> SEQ ID NO 7
<211> LENGTH: 30
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 7

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 8
<211> LENGTH: 45
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 8

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser
        35                  40                  45

<210> SEQ ID NO 9
<211> LENGTH: 60
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 9

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser Gly Gly Gly Gly Ser Gly Gly Gly
        35                  40                  45

Gly Ser Gly Gly Gly Gly Ser Gly Gly Gly Gly Ser
    50                  55                  60

<210> SEQ ID NO 10
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Gly Gly Gly Gly Ser
1               5

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
```

```
                               Synthetic peptide"

<400> SEQUENCE: 11

Gly Gly Gly Gly Ser Gly Gly Gly Gly Ser
1               5                   10

<210> SEQ ID NO 12
<211> LENGTH: 20
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Gly Gly Gly Gly Ser Gly Gly Gly Gly Ser Gly Gly Gly Gly Ser Gly
1               5                   10                  15

Gly Gly Gly Ser
            20

<210> SEQ ID NO 13
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 14
<211> LENGTH: 35
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 15
<211> LENGTH: 40
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 15

Gly Gly Gly Gly Ser Gly Gly Gly Gly Ser Gly Gly Gly Gly Ser Gly
1               5                   10                  15
```

-continued

Gly Gly Gly Ser Gly Gly Gly Gly Ser Gly Gly
            20                  25                  30

Gly Gly Ser Gly Gly Gly Ser
        35                  40

<210> SEQ ID NO 16
<211> LENGTH: 50
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 16

Gly Gly Gly Gly Ser Gly Gly Gly Ser Gly Gly Gly Gly Ser Gly
1               5                   10                  15

Gly Gly Gly Ser Gly Gly Gly Gly Ser Gly Gly Gly Gly Ser Gly
            20                  25                  30

Gly Gly Ser Gly Gly Gly Gly Ser Gly Gly Gly Ser Gly Gly Gly
        35                  40                  45

Gly Ser
    50

<210> SEQ ID NO 17
<211> LENGTH: 55
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 17

Gly Gly Gly Gly Ser Gly Gly Gly Ser Gly Gly Gly Ser Gly
1               5                   10                  15

Gly Gly Gly Ser Gly Gly Gly Gly Ser Gly Gly Gly Ser Gly Gly
            20                  25                  30

Gly Gly Ser Gly Gly Gly Gly Ser Gly Gly Gly Ser Gly Gly Gly
        35                  40                  45

Gly Ser Gly Gly Gly Gly Ser
    50                  55

<210> SEQ ID NO 18
<211> LENGTH: 7
<212> TYPE: PRT
<213> ORGANISM: Simian virus 40

<400> SEQUENCE: 18

Pro Lys Lys Lys Arg Lys Val
1               5

<210> SEQ ID NO 19
<211> LENGTH: 16
<212> TYPE: PRT
<213> ORGANISM: Unknown
<220> FEATURE:
<221> NAME/KEY: source
<223> OTHER INFORMATION: /note="Description of Unknown:
      Nucleoplasmin bipartite NLS sequence"

<400> SEQUENCE: 19

Lys Arg Pro Ala Ala Thr Lys Lys Ala Gly Gln Ala Lys Lys Lys Lys
1               5                   10                  15

<210> SEQ ID NO 20
<211> LENGTH: 9
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 20

Pro Ala Ala Lys Arg Val Lys Leu Asp
1               5

<210> SEQ ID NO 21
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      C-myc NLS sequence"

<400> SEQUENCE: 21

Arg Gln Arg Arg Asn Glu Leu Lys Arg Ser Pro
1               5                   10

<210> SEQ ID NO 22
<211> LENGTH: 38
<212> TYPE: PRT
<213> ORGANISM: Homo sapiens

<400> SEQUENCE: 22

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
        35

<210> SEQ ID NO 23
<211> LENGTH: 42
<212> TYPE: PRT
<213> ORGANISM: Unknown
<220> FEATURE:
<221> NAME/KEY: source
<223> OTHER INFORMATION: /note="Description of Unknown:
      IBB domain from importin-alpha sequence"

<400> SEQUENCE: 23

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
        35                  40

<210> SEQ ID NO 24
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

```
<400> SEQUENCE: 24

Val Ser Arg Lys Arg Pro Arg Pro
1               5

<210> SEQ ID NO 25
<211> LENGTH: 8
<212> TYPE: PRT
<213> ORGANISM: Unknown
<220> FEATURE:
<221> NAME/KEY: source
<223> OTHER INFORMATION: /note="Description of Unknown:
      Myoma T protein sequence"

<400> SEQUENCE: 25

Pro Pro Lys Lys Ala Arg Glu Asp
1               5

<210> SEQ ID NO 26
<211> LENGTH: 8
<212> TYPE: PRT
<213> ORGANISM: Homo sapiens

<400> SEQUENCE: 26

Pro Gln Pro Lys Lys Lys Pro Leu
1               5

<210> SEQ ID NO 27
<211> LENGTH: 12
<212> TYPE: PRT
<213> ORGANISM: Mus musculus

<400> SEQUENCE: 27

Ser Ala Leu Ile Lys Lys Lys Lys Lys Met Ala Pro
1               5                   10

<210> SEQ ID NO 28
<211> LENGTH: 5
<212> TYPE: PRT
<213> ORGANISM: Influenza virus

<400> SEQUENCE: 28

Asp Arg Leu Arg Arg
1               5

<210> SEQ ID NO 29
<211> LENGTH: 7
<212> TYPE: PRT
<213> ORGANISM: Influenza virus

<400> SEQUENCE: 29

Pro Lys Gln Lys Lys Arg Lys
1               5

<210> SEQ ID NO 30
<211> LENGTH: 10
<212> TYPE: PRT
<213> ORGANISM: Hepatitis delta virus

<400> SEQUENCE: 30

Arg Lys Leu Lys Lys Lys Ile Lys Lys Leu
1               5                   10

<210> SEQ ID NO 31
<211> LENGTH: 10
<212> TYPE: PRT
```

```
<213> ORGANISM: Mus musculus

<400> SEQUENCE: 31

Arg Glu Lys Lys Lys Phe Leu Lys Arg Arg
1               5                   10

<210> SEQ ID NO 32
<211> LENGTH: 20
<212> TYPE: PRT
<213> ORGANISM: Homo sapiens

<400> SEQUENCE: 32

Lys Arg Lys Gly Asp Glu Val Asp Gly Val Asp Glu Val Ala Lys Lys
1               5                   10                  15

Lys Ser Lys Lys
            20

<210> SEQ ID NO 33
<211> LENGTH: 17
<212> TYPE: PRT
<213> ORGANISM: Homo sapiens

<400> SEQUENCE: 33

Arg Lys Cys Leu Gln Ala Gly Met Asn Leu Glu Ala Arg Lys Thr Lys
1               5                   10                  15

Lys

<210> SEQ ID NO 34
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Ser Gly Gly Gly
1

<210> SEQ ID NO 35
<211> LENGTH: 352
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: MISC_FEATURE
<222> LOCATION: (1)..(21)
<223> OTHER INFORMATION: /note="This region may or may not be absent in
      its entirety"

<400> SEQUENCE: 35

Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
                20                  25                  30

Ala His Arg Cys Glu Gly Arg Val Glu Val Glu His Asn Gly Gln Trp
            35                  40                  45

Gly Thr Val Cys Asp Asp Gly Trp Asp Arg Arg Asp Val Ala Val Val
        50                  55                  60

Cys Arg Glu Leu Asn Cys Gly Ala Val Ile Gln Thr Pro Arg Gly Ala
```

```
                65                  70                  75                  80
Ser Tyr Gln Pro Pro Ala Ser Glu Gln Arg Val Leu Ile Gln Gly Val
                    85                  90                  95

Asp Cys Asn Gly Thr Glu Asp Thr Leu Ala Gln Cys Glu Leu Asn Tyr
                    100                 105                 110

Asp Val Phe Asp Cys Ser His Glu Asp Ala Gly Ala Gln Cys Glu
                    115                 120                 125

Asn Pro Asp Ser Asp Leu Leu Phe Ile Pro Glu Asp Val Arg Leu Val
            130                 135                 140

Asp Gly Pro Gly His Cys Gln Gly Arg Val Glu Val Leu His Gln Ser
145                 150                 155                 160

Gln Trp Ser Thr Val Cys Lys Ala Gly Trp Asn Leu Gln Val Ser Lys
                    165                 170                 175

Val Val Cys Arg Gln Leu Gly Cys Gly Arg Ala Leu Leu Thr Tyr Gly
                    180                 185                 190

Ser Cys Asn Lys Ser Thr Gln Gly Lys Gly Pro Ile Trp Met Gly Lys
                    195                 200                 205

Met Ser Cys Ser Gly Gln Glu Ala Asn Leu Arg Ser Cys Leu Leu Ser
            210                 215                 220

Arg Leu Glu Asn Asn Cys Thr His Gly Glu Asp Thr Trp Met Glu Cys
225                 230                 235                 240

Glu Asp Pro Phe Glu Leu Lys Leu Val Gly Gly Asp Thr Pro Cys Ser
                    245                 250                 255

Gly Arg Leu Glu Val Leu His Lys Gly Ser Trp Gly Ser Val Cys Asp
                    260                 265                 270

Asp Asn Trp Gly Glu Lys Glu Asp Gln Val Val Cys Lys Gln Leu Gly
            275                 280                 285

Cys Gly Lys Ser Leu His Pro Ser Pro Lys Thr Arg Lys Ile Tyr Gly
            290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                    325                 330                 335

Cys Thr His Lys Glu Asp Val Glu Val Ile Cys Thr Asp Phe Asp Val
                    340                 345                 350

<210> SEQ ID NO 36
<211> LENGTH: 335
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                    20                  25                  30

Val Glu Val Asp Trp Thr Pro Asp Ala Pro Gly Glu Thr Val Asn Leu
                35                  40                  45

Thr Cys Asp Thr Pro Glu Glu Asp Asp Ile Thr Trp Thr Ser Asp Gln
            50                  55                  60

Arg His Gly Val Ile Gly Ser Gly Lys Thr Leu Thr Ile Thr Val Lys
65                  70                  75                  80
```

Glu Phe Leu Asp Ala Gly Gln Tyr Thr Cys His Lys Gly Glu Thr
              85                  90                  95

Leu Ser His Ser His Leu Leu His Lys Lys Glu Asn Gly Ile Trp
            100                 105                 110

Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
        130                 135                 140

Arg Asn Met Asp Leu Lys Phe Asn Ile Lys Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
                180                 185                 190

Glu Asp Val Thr Cys Pro Thr Ala Glu Glu Thr Leu Pro Ile Glu Leu
            195                 200                 205

Ala Leu Glu Ala Arg Gln Gln Asn Lys Tyr Glu Asn Tyr Ser Thr Ser
        210                 215                 220

Phe Phe Ile Arg Asp Ile Ile Lys Pro Asp Pro Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
                260                 265                 270

Arg Ile Gln Arg Lys Lys Glu Lys Met Lys Glu Thr Glu Glu Gly Cys
            275                 280                 285

Asn Gln Lys Gly Ala Phe Leu Val Glu Lys Thr Ser Thr Glu Val Gln
        290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 37
<211> LENGTH: 352
<212> TYPE: PRT
<213> ORGANISM: Mus musculus

<400> SEQUENCE: 37

Met Ala Pro Leu Phe Asn Leu Met Leu Ala Ile Leu Ser Ile Phe Val
1               5                   10                  15

Gly Ser Cys Phe Ser Glu Ser Pro Thr Lys Val Gln Leu Val Gly Gly
            20                  25                  30

Ala His Arg Cys Glu Gly Arg Val Glu Val Glu His Asn Gly Gln Trp
        35                  40                  45

Gly Thr Val Cys Asp Asp Gly Trp Asp Arg Arg Asp Val Ala Val Val
    50                  55                  60

Cys Arg Glu Leu Asn Cys Gly Ala Val Ile Gln Thr Pro Arg Gly Ala
65                  70                  75                  80

Ser Tyr Gln Pro Pro Ala Ser Glu Gln Arg Val Leu Ile Gln Gly Val
                85                  90                  95

Asp Cys Asn Gly Thr Glu Asp Thr Leu Ala Gln Cys Glu Leu Asn Tyr
            100                 105                 110

Asp Val Phe Asp Cys Ser His Glu Glu Asp Ala Gly Ala Gln Cys Glu

```
            115                 120                 125
Asn Pro Asp Ser Asp Leu Leu Phe Ile Pro Glu Asp Val Arg Leu Val
    130                 135                 140

Asp Gly Pro Gly His Cys Gln Gly Arg Val Glu Val Leu His Gln Ser
145                 150                 155                 160

Gln Trp Ser Thr Val Cys Lys Ala Gly Trp Asn Leu Gln Val Ser Lys
                165                 170                 175

Val Val Cys Arg Gln Leu Gly Cys Gly Arg Ala Leu Leu Thr Tyr Gly
            180                 185                 190

Ser Cys Asn Lys Ser Thr Gln Gly Lys Gly Pro Ile Trp Met Gly Lys
        195                 200                 205

Met Ser Cys Ser Gly Gln Glu Ala Asn Leu Arg Ser Cys Leu Leu Ser
    210                 215                 220

Arg Leu Glu Asn Asn Cys Thr His Gly Asp Thr Trp Met Glu Cys
225                 230                 235                 240

Glu Asp Pro Phe Glu Leu Lys Leu Val Gly Gly Asp Thr Pro Cys Ser
                245                 250                 255

Gly Arg Leu Glu Val Leu His Lys Gly Ser Trp Gly Ser Val Cys Asp
            260                 265                 270

Asp Asn Trp Gly Glu Lys Glu Asp Gln Val Val Cys Lys Gln Leu Gly
        275                 280                 285

Cys Gly Lys Ser Leu His Pro Ser Pro Lys Thr Arg Lys Ile Tyr Gly
    290                 295                 300

Pro Gly Ala Gly Arg Ile Trp Leu Asp Asp Val Asn Cys Ser Gly Lys
305                 310                 315                 320

Glu Gln Ser Leu Glu Phe Cys Arg His Arg Leu Trp Gly Tyr His Asp
                325                 330                 335

Cys Thr His Lys Glu Asp Val Glu Val Ile Cys Thr Asp Phe Asp Val
            340                 345                 350

<210> SEQ ID NO 38
<211> LENGTH: 347
<212> TYPE: PRT
<213> ORGANISM: Homo sapiens

<400> SEQUENCE: 38

Met Ala Leu Leu Phe Ser Leu Ile Leu Ala Ile Cys Thr Arg Pro Gly
1               5                   10                  15

Phe Leu Ala Ser Pro Ser Gly Val Arg Leu Val Gly Gly Leu His Arg
                20                  25                  30

Cys Glu Gly Arg Val Glu Val Glu Gln Lys Gly Gln Trp Gly Thr Val
            35                  40                  45

Cys Asp Asp Gly Trp Asp Ile Lys Asp Val Ala Val Leu Cys Arg Glu
50                  55                  60

Leu Gly Cys Gly Ala Ala Ser Gly Thr Pro Ser Gly Ile Leu Tyr Glu
65                  70                  75                  80

Pro Pro Ala Glu Lys Glu Gln Lys Val Leu Ile Gln Ser Val Ser Cys
                85                  90                  95

Thr Gly Thr Glu Asp Thr Leu Ala Gln Cys Glu Gln Glu Glu Val Tyr
            100                 105                 110

Asp Cys Ser His Asp Glu Asp Ala Gly Ala Ser Cys Glu Asn Pro Glu
        115                 120                 125

Ser Ser Phe Ser Pro Val Pro Glu Gly Val Arg Leu Ala Asp Gly Pro
    130                 135                 140
```

```
Gly His Cys Lys Gly Arg Val Glu Val Lys His Gln Asn Gln Trp Tyr
145                 150                 155                 160

Thr Val Cys Gln Thr Gly Trp Ser Leu Arg Ala Ala Lys Val Val Cys
                165                 170                 175

Arg Gln Leu Gly Cys Gly Arg Ala Val Leu Thr Gln Lys Arg Cys Asn
            180                 185                 190

Lys His Ala Tyr Gly Arg Lys Pro Ile Trp Leu Ser Gln Met Ser Cys
        195                 200                 205

Ser Gly Arg Glu Ala Thr Leu Gln Asp Cys Pro Ser Gly Pro Trp Gly
    210                 215                 220

Lys Asn Thr Cys Asn His Asp Glu Asp Thr Trp Val Glu Cys Glu Asp
225                 230                 235                 240

Pro Phe Asp Leu Arg Leu Val Gly Gly Asp Asn Leu Cys Ser Gly Arg
                245                 250                 255

Leu Glu Val Leu His Lys Gly Val Trp Gly Ser Val Cys Asp Asp Asn
            260                 265                 270

Trp Gly Glu Lys Glu Asp Gln Val Val Cys Lys Gln Leu Gly Cys Gly
        275                 280                 285

Lys Ser Leu Ser Pro Ser Phe Arg Asp Arg Lys Cys Tyr Gly Pro Gly
    290                 295                 300

Val Gly Arg Ile Trp Leu Asp Asn Val Arg Cys Ser Gly Glu Glu Gln
305                 310                 315                 320

Ser Leu Glu Gln Cys Gln His Arg Phe Trp Gly Phe His Asp Cys Thr
                325                 330                 335

His Gln Glu Asp Val Ala Val Ile Cys Ser Val
            340                 345

<210> SEQ ID NO 39
<211> LENGTH: 196
<212> TYPE: PRT
<213> ORGANISM: Mus musculus

<400> SEQUENCE: 39

Met Leu Asp Cys Arg Ala Val Ile Met Leu Trp Leu Pro Trp Val
1               5                   10                  15

Thr Gln Gly Leu Ala Val Pro Arg Ser Ser Pro Asp Trp Ala Gln
                20                  25                  30

Cys Gln Gln Leu Ser Arg Asn Leu Cys Met Leu Ala Trp Asn Ala His
            35                  40                  45

Ala Pro Ala Gly His Met Asn Leu Leu Arg Glu Glu Asp Glu Glu
    50                  55                  60

Thr Lys Asn Asn Val Pro Arg Ile Gln Cys Glu Asp Gly Cys Asp Pro
65                  70                  75                  80

Gln Gly Leu Lys Asp Asn Ser Gln Phe Cys Leu Gln Arg Ile Arg Gln
                85                  90                  95

Gly Leu Ala Phe Tyr Lys His Leu Leu Asp Ser Asp Ile Phe Lys Gly
            100                 105                 110

Glu Pro Ala Leu Leu Pro Asp Ser Pro Met Glu Gln Leu His Thr Ser
        115                 120                 125

Leu Leu Gly Leu Ser Gln Leu Leu Gln Pro Glu Asp His Pro Arg Glu
    130                 135                 140

Thr Gln Gln Met Pro Ser Leu Ser Ser Gln Gln Trp Gln Arg Pro
145                 150                 155                 160

Leu Leu Arg Ser Lys Ile Leu Arg Ser Leu Gln Ala Phe Leu Ala Ile
                165                 170                 175
```

```
Ala Ala Arg Val Phe Ala His Gly Ala Ala Thr Leu Thr Glu Pro Leu
            180                 185                 190

Val Pro Thr Ala
        195

<210> SEQ ID NO 40
<211> LENGTH: 189
<212> TYPE: PRT
<213> ORGANISM: Homo sapiens

<400> SEQUENCE: 40

Met Leu Gly Ser Arg Ala Val Met Leu Leu Leu Leu Pro Trp Thr
1               5                   10                  15

Ala Gln Gly Arg Ala Val Pro Gly Gly Ser Ser Pro Ala Trp Thr Gln
                20                  25                  30

Cys Gln Gln Leu Ser Gln Lys Leu Cys Thr Leu Ala Trp Ser Ala His
            35                  40                  45

Pro Leu Val Gly His Met Asp Leu Arg Glu Glu Gly Asp Glu Glu Thr
        50                  55                  60

Thr Asn Asp Val Pro His Ile Gln Cys Gly Asp Gly Cys Asp Pro Gln
65                  70                  75                  80

Gly Leu Arg Asp Asn Ser Gln Phe Cys Leu Gln Arg Ile His Gln Gly
                85                  90                  95

Leu Ile Phe Tyr Glu Lys Leu Leu Gly Ser Asp Ile Phe Thr Gly Glu
            100                 105                 110

Pro Ser Leu Leu Pro Asp Ser Pro Val Gly Gln Leu His Ala Ser Leu
        115                 120                 125

Leu Gly Leu Ser Gln Leu Leu Gln Pro Glu Gly His His Trp Glu Thr
    130                 135                 140

Gln Gln Ile Pro Ser Leu Ser Pro Ser Gln Pro Trp Gln Arg Leu Leu
145                 150                 155                 160

Leu Arg Phe Lys Ile Leu Arg Ser Leu Gln Ala Phe Val Ala Val Ala
                165                 170                 175

Ala Arg Val Phe Ala His Gly Ala Ala Thr Leu Ser Pro
            180                 185

<210> SEQ ID NO 41
<211> LENGTH: 335
<212> TYPE: PRT
<213> ORGANISM: Mus musculus

<400> SEQUENCE: 41

Met Cys Pro Gln Lys Leu Thr Ile Ser Trp Phe Ala Ile Val Leu Leu
1               5                   10                  15

Val Ser Pro Leu Met Ala Met Trp Glu Leu Glu Lys Asp Val Tyr Val
                20                  25                  30

Val Glu Val Asp Trp Thr Pro Asp Ala Pro Gly Glu Thr Val Asn Leu
            35                  40                  45

Thr Cys Asp Thr Pro Glu Glu Asp Ile Thr Trp Thr Ser Asp Gln
        50                  55                  60

Arg His Gly Val Ile Gly Ser Gly Lys Thr Leu Thr Ile Thr Val Lys
65                  70                  75                  80

Glu Phe Leu Asp Ala Gly Gln Tyr Thr Cys His Lys Gly Gly Glu Thr
                85                  90                  95

Leu Ser His Ser His Leu Leu Leu His Lys Lys Glu Asn Gly Ile Trp
            100                 105                 110
```

```
Ser Thr Glu Ile Leu Lys Asn Phe Lys Asn Lys Thr Phe Leu Lys Cys
            115                 120                 125

Glu Ala Pro Asn Tyr Ser Gly Arg Phe Thr Cys Ser Trp Leu Val Gln
        130                 135                 140

Arg Asn Met Asp Leu Lys Phe Asn Ile Lys Ser Ser Ser Ser Ser Pro
145                 150                 155                 160

Asp Ser Arg Ala Val Thr Cys Gly Met Ala Ser Leu Ser Ala Glu Lys
                165                 170                 175

Val Thr Leu Asp Gln Arg Asp Tyr Glu Lys Tyr Ser Val Ser Cys Gln
            180                 185                 190

Glu Asp Val Thr Cys Pro Thr Ala Glu Glu Thr Leu Pro Ile Glu Leu
        195                 200                 205

Ala Leu Glu Ala Arg Gln Gln Asn Lys Tyr Glu Asn Tyr Ser Thr Ser
    210                 215                 220

Phe Phe Ile Arg Asp Ile Ile Lys Pro Asp Pro Lys Asn Leu Gln
225                 230                 235                 240

Met Lys Pro Leu Lys Asn Ser Gln Val Glu Val Ser Trp Glu Tyr Pro
                245                 250                 255

Asp Ser Trp Ser Thr Pro His Ser Tyr Phe Ser Leu Lys Phe Phe Val
            260                 265                 270

Arg Ile Gln Arg Lys Lys Glu Lys Met Lys Glu Thr Glu Glu Gly Cys
        275                 280                 285

Asn Gln Lys Gly Ala Phe Leu Val Glu Lys Thr Ser Thr Glu Val Gln
    290                 295                 300

Cys Lys Gly Gly Asn Val Cys Val Gln Ala Gln Asp Arg Tyr Tyr Asn
305                 310                 315                 320

Ser Ser Cys Ser Lys Trp Ala Cys Val Pro Cys Arg Val Arg Ser
                325                 330                 335

<210> SEQ ID NO 42
<211> LENGTH: 215
<212> TYPE: PRT
<213> ORGANISM: Mus musculus

<400> SEQUENCE: 42

Met Cys Gln Ser Arg Tyr Leu Leu Phe Leu Ala Thr Leu Val Leu Leu
1               5                   10                  15

Asn His Leu Thr Ser Ala Arg Val Ile Pro Val Ser Gly Pro Ala Lys
            20                  25                  30

Cys Leu Asn Gln Ser Gln Asn Leu Leu Lys Thr Thr Asp Asp Met Val
        35                  40                  45

Arg Thr Ala Arg Glu Lys Leu Lys His Tyr Ser Cys Thr Ala Gly Asp
    50                  55                  60

Ile Asp His Glu Asp Ile Thr Arg Asp Lys Thr Ser Thr Leu Glu Ala
65                  70                  75                  80

Cys Leu Pro Leu Glu Leu His Lys Asn Glu Ser Cys Leu Ala Thr Lys
                85                  90                  95

Glu Thr Ser Ser Ile Ile Arg Gly Ser Cys Leu Pro Pro Gln Lys Thr
            100                 105                 110

Ser Leu Met Met Thr Leu Cys Leu Gly Ser Ile Tyr Glu Asp Leu Lys
        115                 120                 125

Met Tyr Gln Ser Glu Phe Gln Ala Ile Asn Ala Ala Leu Gln Ser His
    130                 135                 140

Asn His Gln Gln Ile Thr Leu Asp Arg Asn Met Leu Met Ala Ile Asp
```

```
                145                 150                 155                 160
        Glu Leu Met Arg Ser Leu Asn His Ser Gly Glu Thr Leu His Gln Lys
                            165                 170                 175

Ala Pro Met Gly Glu Ala Asp Pro Tyr Arg Val Lys Met Lys Leu Cys
                            180                 185                 190

Ile Leu Leu His Ala Phe Ser Thr Arg Val Met Thr Ile Asn Arg Val
                        195                 200                 205

Met Asn Tyr Leu Ser Ser Ser
                210                 215

<210> SEQ ID NO 43
<211> LENGTH: 253
<212> TYPE: PRT
<213> ORGANISM: Homo sapiens

<400> SEQUENCE: 43

Met Trp Pro Pro Gly Ser Ala Ser Gln Pro Pro Pro Ser Pro Ala Ala
1               5                   10                  15

Ala Thr Gly Leu His Pro Ala Ala Arg Pro Val Ser Leu Gln Cys Arg
            20                  25                  30

Leu Ser Met Cys Pro Ala Arg Ser Leu Leu Leu Val Ala Thr Leu Val
        35                  40                  45

Leu Leu Asp His Leu Ser Leu Ala Arg Asn Leu Pro Val Ala Thr Pro
    50                  55                  60

Asp Pro Gly Met Phe Pro Cys Leu His His Ser Gln Asn Leu Leu Arg
65                  70                  75                  80

Ala Val Ser Asn Met Leu Gln Lys Ala Arg Gln Thr Leu Glu Phe Tyr
                85                  90                  95

Pro Cys Thr Ser Glu Glu Ile Asp His Glu Asp Ile Thr Lys Asp Lys
            100                 105                 110

Thr Ser Thr Val Glu Ala Cys Leu Pro Leu Glu Leu Thr Lys Asn Glu
        115                 120                 125

Ser Cys Leu Asn Ser Arg Glu Thr Ser Phe Ile Thr Asn Gly Ser Cys
    130                 135                 140

Leu Ala Ser Arg Lys Thr Ser Phe Met Met Ala Leu Cys Leu Ser Ser
145                 150                 155                 160

Ile Tyr Glu Asp Leu Lys Met Tyr Gln Val Glu Phe Lys Thr Met Asn
                165                 170                 175

Ala Lys Leu Leu Met Asp Pro Lys Arg Gln Ile Phe Leu Asp Gln Asn
            180                 185                 190

Met Leu Ala Val Ile Asp Glu Leu Met Gln Ala Leu Asn Phe Asn Ser
        195                 200                 205

Glu Thr Val Pro Gln Lys Ser Ser Leu Glu Glu Pro Asp Phe Tyr Lys
    210                 215                 220

Thr Lys Ile Lys Leu Cys Ile Leu Leu His Ala Phe Arg Ile Arg Ala
225                 230                 235                 240

Val Thr Ile Asp Arg Val Met Ser Tyr Leu Asn Ala Ser
                245                 250
```